(12) United States Patent
Curtin et al.

(10) Patent No.: US 7,129,260 B2
(45) Date of Patent: Oct. 31, 2006

(54) ISOINDOLINONE KINASE INHIBITORS

(75) Inventors: Michael L. Curtin, Pleasant Prairie, WI (US); Steven K. Davidsen, Libertyville, IL (US); Robin R. Frey, Libertyville, IL (US); Howard R. Heyman, Deerfield, IL (US); James H. Holms, Gurnee, IL (US); Michael Michaelides, Libertyville, IL (US); Douglas H. Steinman, Morton Grove, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/858,934

(22) Filed: Jun. 2, 2004

(65) Prior Publication Data

US 2005/0026976 A1     Feb. 3, 2005

Related U.S. Application Data

(60) Provisional application No. 60/475,110, filed on Jun. 2, 2003.

(51) Int. Cl.
*A61K 31/40* (2006.01)
*C07D 207/00* (2006.01)

(52) U.S. Cl. ........................ 514/408; 548/400
(58) Field of Classification Search ................ 514/408; 548/400
See application file for complete search history.

(56) References Cited

U.S. PATENT DOCUMENTS 6,277,847 B1 * 8/2001 Theodoridis et al. ....... 504/242

FOREIGN PATENT DOCUMENTS

WO     01/19828     3/2001
WO     03/051366     6/2003

OTHER PUBLICATIONS

Noguchi, M. Cycloaddition reaction of 2-pyrone-6-carboxamides. Bulletin of the Chemical Society of Japan, vol. 59, Issue 5, pp. 1355-1362, 1986.*
Adams et al., "A strategy for the design of multiplex inhibitors for kinase-mediated signaling in angiogenesis," Current Opinion in Chemical Biology 6(4):486-492(2002).
Rupert et al., "Suzuki couplings with phthalimidines-an efficient route to staurosporinone analogs," Heterocycles 45(11):2217-2221 (1997).

* cited by examiner

*Primary Examiner*—Kamal A. Saeed
*Assistant Examiner*—Susannah L. Chung
(74) *Attorney, Agent, or Firm*—B. Gregory Donner

(57) ABSTRACT

Compounds having the formula

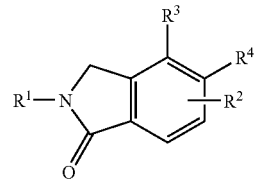

are useful for inhibiting protein tyrosine kinases. The present invention also discloses methods of making the compounds, compositions containing the compounds, and methods of treatment using the compounds.

15 Claims, No Drawings

ISOINDOLINONE KINASE INHIBITORS

This application claims priority to U.S. Provisional Patent Application Ser. No. 60/475,110, filed Jun. 2, 2003.

TECHNICAL FIELD

The present invention relates to compounds which are useful for inhibiting protein tyrosine kinases, methods of making the compounds, compositions containing the compounds, and methods of treatment using the compounds.

BACKGROUND OF THE INVENTION

Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation, or differentiation. Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

In its principle embodiment, the present invention provides a compound of formula (I)

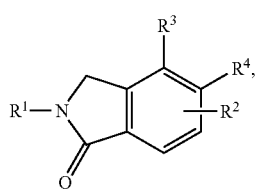

(I)

or a therapeutically acceptable salt thereof, wherein
$R^1$ is selected from the group consisting of hydrogen and alkyl;
$R^2$ is selected from the group consisting of hydrogen, alkoxy, alkoxyalkoxy, alkyl, carboxyalkoxy, carboxyalkyl, halo, haloalkyl, heterocyclylalkoxy, hydroxy, nitro, and —$NR^cR^d$; and
one of $R^3$ and $R^4$ is A-X-$R^5$ and the other is hydrogen; wherein A-X-$R^5$ is drawn with its left end attached to the parent molecular moiety;
$R^5$ is selected from the group consisting of aryl, heteroaryl, and heterocyclyl;
A is selected from the group consisting of aryl and heteroaryl, wherein the aryl and the heteroaryl are optionally substituted with one or two substituents independently selected from the group consisting of alkyl, halo, haloalkoxy, and haloalkyl; and
X is selected from the group consisting of O, $NR^a$, $N(R^a)C(S)N(R^b)$, $(CH_2)_mN(R^a)C(O)N(R^b)(CH_2)_n$, $CH_2C(O)N(R^a)$, and $N(R^a)C(O)$, wherein $R^a$ and $R^b$ are independently selected from the group consisting of hydrogen and alkyl, m and n are independently 0 or 1, and wherein each group is drawn with its left end attached to A and its right end attached to $R^5$.

In a preferred embodiment, the present invention discloses a compound of formula (I) where $R^1$ is hydrogen.

In a preferred embodiment, the present invention discloses a compound of formula (I) where $R^3$ is A-X-$R^5$ and $R^4$ is hydrogen.

In another preferred embodiment, the present invention discloses a compound of formula (I) where $R^3$ is A-X-$R^5$, $R^4$ is hydrogen, and X is selected from the group consisting of O, $NR^a$, $N(R^a)C(S)N(R^b)$, $CH_2C(O)N(R^a)$, and $N(R^a)C(O)$.

In another preferred embodiment, the present invention discloses a compound of formula (I) where $R^3$ is A-X-$R^5$, $R^4$ is hydrogen, and X is $(CH_2)_mN(R^a)C(O)N(R^b)(CH_2)_n$.

In another preferred embodiment, the present invention discloses a compound of formula (I) where $R^3$ is A-X-$R^5$, $R^4$ is hydrogen, X is $(CH_2)_mN(R^a)C(O)N(R^b)(CH_2)_n$, $R^a$ and $R^b$ are hydrogen, and m and n are 0.

In another preferred embodiment, the present invention discloses a compound of formula (I) where $R^3$ is A-X-$R^5$, $R^4$ is hydrogen, X is $(CH_2)_mN(R^a)C(O)N(R^b)(CH_2)_n$, and $R^2$ is other than hydrogen.

In another preferred embodiment, the present invention discloses a compound of formula (I) where $R^3$ is A-X-$R^5$, $R^4$ is hydrogen, X is $(CH_2)_mN(R^a)C(O)N(R^b)(CH_2)_n$, $R^2$ is hydrogen, and $R^5$ is selected from the group consisting of aryl and heteroaryl, wherein the aryl and the heteroaryl are unsubstituted.

In another preferred embodiment, the present invention discloses a compound of formula (I) where $R^3$ is A-X-$R^5$, $R^4$ is hydrogen, X is $(CH_2)_mN(R^a)C(O)N(R^b)(CH_2)_n$, $R^2$ is hydrogen, and $R^5$ is selected from the group consisting of aryl and heteroaryl, wherein the aryl and the heteroaryl are monosubstituted.

In another preferred embodiment, the present invention discloses a compound of formula (I) where $R^3$ is A-X-$R^5$, $R^4$ is hydrogen, X is $(CH_2)_mN(R^a)C(O)N(R^b)(CH_2)_n$, $R^2$ is hydrogen, $R^5$ is selected from the group consisting of aryl and heteroaryl, wherein the aryl and the heteroaryl are monosubstituted, and A is selected from the group consisting of aryl and heteroaryl, wherein the aryl and the heteroaryl are unsubstituted.

In another preferred embodiment, the present invention discloses a compound of formula (I) where $R^3$ is A-X-$R^5$, $R^4$ is hydrogen, X is $(CH_2)_mN(R^a)C(O)N(R^b)(CH_2)_n$, $R^2$ is hydrogen, $R^5$ is selected from the group consisting of aryl and heteroaryl, wherein the aryl and the heteroaryl are monosubstituted, and A is selected from the group consisting of aryl and heteroaryl, wherein the aryl and the heteroaryl are monosubstituted.

In another preferred embodiment, the present invention discloses a compound of formula (I) where $R^3$ is A-X-$R^5$, $R^4$ is hydrogen, X is $(CH_2)_mN(R^a)C(O)N(R^b)(CH_2)_n$, $R^2$ is hydrogen, and $R^5$ is selected from the group consisting of aryl and heteroaryl, wherein the aryl and the heteroaryl are disubstituted.

In another preferred embodiment, the present invention discloses a compound of formula (I) where $R^3$ is A-X-$R^5$, $R^4$ is hydrogen, X is $(CH_2)_mN(R^a)C(O)N(R^b)(CH_2)_n$, $R^2$ is hydrogen, $R^5$ is selected from the group consisting of aryl and heteroaryl, wherein the aryl and the heteroaryl are disubstituted, and A is selected from the group consisting of aryl and heteroaryl, wherein the aryl and the heteroaryl are unsubstituted.

In another preferred embodiment, the present invention discloses a compound of formula (I) where $R^3$ is A-X-$R^5$, $R^4$ is hydrogen, X is $(CH_2)_mN(R^a)C(O)N(R^b)(CH_2)_n$, $R^2$ is hydrogen, $R^5$ is selected from the group consisting of aryl and heteroaryl, wherein the aryl and the heteroaryl are disubstituted, and A is selected from the group consisting of aryl and heteroaryl, wherein the aryl and the heteroaryl are monosubstituted.

In another embodiment, the present invention provides a pharmaceutical composition comprising a compound of formula (I) or a therapeutically acceptable salt thereof, in combination with a therapeutically acceptable carrier.

In another embodiment, the present invention provides a method for inhibiting protein kinase in a patient in recognized need of such treatment comprising administering to the patient a therapeutically acceptable amount of a compound of formula (I), or a therapeutically acceptable salt thereof.

In another embodiment, the present invention provides a method for treating cancer in a patient in recognized need of such treatment comprising administering to the patient a therapeutically acceptable amount of a compound of formula (I), or a therapeutically acceptable salt thereof.

DETAILED DESCRIPTION OF THE INVENTION

All publications, issued patents, and patent applications cited herein are hereby incorporated by reference.

As used in the present specification the following terms have the meanings indicated:

The term "alkoxy," as used herein, refers to an alkyl group attached to the parent molecular moiety through an oxygen atom.

The term "alkoxyalkoxy," as used herein, refers to an alkoxy group attached to the parent molecular moiety through another alkoxy group.

The term "alkoxyalkoxyalkyl," as used herein, refers to an alkoxyalkoxy group attached to the parent molecular moiety through an alkyl group.

The term "alkoxyalkoxyalkylcarbonyl," as used herein, refers to an alkoxyalkoxyalkyl group attached to the parent molecular moiety through a carbonyl group.

The term "alkoxyalkyl," as used herein, refers to an alkoxy group attached to the parent molecular moiety through an alkyl group.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "aryl," as used herein, refers to a phenyl group, or a bicyclic or tricyclic fused ring system wherein one or more of the fused rings is a phenyl group. Bicyclic fused ring systems are exemplified by a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Representative examples of aryl include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkoxy, alkoxycarbonyl, alkyl, alkylcarbonyl, alkylsulfanyl, a second aryl group, arylalkoxy, arylalkyl, aryloxy, arylsulfanyl, carboxy, cyano, cyanoalkyl, halo, haloalkoxy, haloalkyl, heteroaryl, heteroarylalkyl, heterocyclyl, heterocyclylalkyl, hydroxy, nitro, oxo, and $-NR^cR^d$, wherein the second aryl group, the aryl part of the arylalkoxy, the arylalkyl, the aryloxy, and the arylsulfanyl, the heteroaryl, the heteroaryl part of the heteroarylalkyl, the heterocyclyl, and the heterocyclyl part of the heterocyclylalkyl can be further optionally substituted with one, two, three, four, or five substituents independently selected from the group consisting of alkoxy, alkoxycarbonyl, alkyl, alkylcarbonyl, carboxy, cyano, halo, haloalkoxy, haloalkyl, hydroxy, and nitro.

The term "arylalkoxy," as used herein, refers to an aryl group attached to the parent molecular moiety through an alkoxy group.

The term "arylalkoxycarbonyl," as used herein, refers to an arylalkoxy group attached to the parent molecular moiety through a carbonyl group.

The term "arylalkyl," as used herein, refers to an aryl group attached to the parent molecular moiety through an alkyl group.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "arylsulfanyl," as used herein, refers to an aryl group attached to the parent molecular moiety through a sulfur atom.

The term "carbonyl," as used herein, refers to —C(O)—.

The term "carboxy," as used herein, refers to —CO$_2$H.

The term "carboxyalkoxy," as used herein, refers to a carboxy group attached to the parent molecular moiety through an alkoxy group.

The term "carboxyalkyl," as used herein, refers to a carboxy group attached to the parent molecular moiety through an alkyl group.

The term "cyano," as used herein, refers to —CN.

The term "cyanoalkyl," as used herein, refers to a cyano group attached to the parent molecular moiety through an alkyl group.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to twelve carbon atoms. Examples of cycloalkyl groups include, but are not limited to, cyclopropyl, cyclopentyl, bicyclo[3.1.1]heptyl, and adamantyl.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "heteroaryl," as used herein, refers to an aromatic five- or six-membered ring where at least one atom is selected from the group consisting of N, O, and S, and the remaining atoms are carbon. The five-membered rings have two double bonds, and the six-membered rings have three double bonds. The heteroaryl groups are connected to the parent molecular group through a substitutable carbon or nitrogen atom in the ring. The term "heteroaryl" also includes bicyclic systems where a heteroaryl ring is fused to a phenyl group, a monocyclic cycloalkenyl group, as defined herein, a monocyclic cycloalkyl group, as defined herein, a heterocyclyl group, as defined herein, or an additional heteroaryl group; and tricyclic systems where a bicyclic system is fused to a phenyl group, a monocyclic cycloalkyl group, as defined herein, a heterocyclyl group, as defined herein, or an additional heteroaryl group. Heteroaryls are exemplified by benzothienyl, benzoxadiazolyl, cinnolinyl, dibenzofuranyl, furanyl, imidazolyl, indazolyl, indolyl, isoxazolyl, isoquinolinyl, isothiazolyl, naphthyridinyl, oxadiazolyl, oxadiazolyl, oxazolyl, thiazolyl, thienopyridinyl, thienyl, triazolyl, thiadiazolyl, pyridinyl, pyridazinyl, pyrimidinyl, pyrazinyl, pyrazolyl, pyrrolyl, quinolinyl, triazinyl, and the like. The heteroaryl groups of the present invention can be optionally substituted with one, two, three, four, or five substituents independently selected from the group consisting of alkoxy, alkoxycarbonyl, alkyl, alkylcarbonyl, alkylsulfanyl, aryl, arylalkoxy, arylalkyl, aryloxy, arylsulfanyl, carboxy, cyano, cyanoalkyl, halo, haloalkoxy, haloalkyl, a second heteroaryl, heteroarylalkyl, heterocyclyl, heterocyclylalkyl, hydroxy, nitro, oxo, and —NR$^c$R$^d$, wherein the aryl, the aryl part of the arylalkoxy, the arylalkyl, the aryloxy, and the arylsulfanyl, the second heteroaryl group, the heteroaryl part of the heteroarylalkyl, the heterocyclyl, and the heterocyclyl part of the heterocyclylalkyl can be further optionally substituted with one, two, three, four, or five substituents independently selected from the group consisting of alkoxy, alkoxycarbonyl, alkyl, alkylcarbonyl, carboxy, cyano, halo, haloalkoxy, haloalkyl, hydroxy, and nitro.

The term "heteroarylalkyl," as used herein, refers to a heteroaryl group attached to the parent molecular moiety through an alkyl group.

The term "heteroarylcarbonyl," as used herein, refers to a heteroaryl group attached to the parent molecular moiety through a carbonyl group.

The term "heterocyclyl," as used herein, refers to cyclic, non-aromatic, five-, six-, or seven-membered rings containing at least one atom selected from the group consisting of oxygen, nitrogen, and sulfur. The five-membered rings have zero or one double bonds and the six- and seven-membered rings have zero, one, or two double bonds. The heterocyclyl groups of the invention are connected to the parent molecular group through a substitutable carbon or nitrogen atom in the ring. The term "heterocyclyl" also includes bicyclic systems where a heterocyclyl ring is fused to a phenyl group, a monocyclic cycloalkenyl group, as defined herein, a monocyclic cycloalkyl group, as defined herein, or an additional monocyclic heterocyclyl group; and tricyclic systems where a bicyclic system is fused to a phenyl group, a monocyclic cycloalkenyl group, as defined herein, a monocyclic cycloalkyl group, as defined herein, or an additional monocyclic heterocyclyl group. Examples of heterocyclyl groups include, but are not limited to, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, and thiomorpholinyl. The heterocyclyl groups of the present invention can be optionally substituted with one, two, three, four, or five substituents independently selected from the group consisting of alkoxy, alkoxycarbonyl, alkyl, alkylcarbonyl, alkylsulfanyl, aryl, arylalkoxy, arylalkyl, aryloxy, arylsulfanyl, carboxy, cyano, cyanoalkyl, halo, haloalkoxy, haloalkyl, heteroaryl, heteroarylalkyl, a second heterocyclyl group, heterocyclylalkyl, hydroxy, nitro, oxo, and —NR$^c$R$^d$, wherein the aryl, the aryl part of the arylalkoxy, the arylalkyl, the aryloxy, and the arylsulfanyl, the heteroaryl, the heteroaryl part of the heteroarylalkyl, the second heterocyclyl group, and the heterocyclyl part of the heterocyclylalkyl can be further optionally substituted with one, two, three, four, or five substituents independently selected from the group consisting of alkoxy, alkoxycarbonyl, alkyl, alkylcarbonyl, carboxy, cyano, halo, haloalkoxy, haloalkyl, hydroxy, and nitro.

The term "heterocyclylalkoxy," as used herein, refers to a heterocyclyl group attached to the parent molecular moiety through an alkoxy group.

The term "heterocyclylalkyl," as used herein, refers to a heterocyclyl group attached to the parent molecular moiety through an alkyl group.

The term "heterocyclylcarbonyl," as used herein, refers to a heterocyclyl group attached to the parent molecular moiety through a carbonyl group.

The term "hydroxy," as used herein, refers to —OH.

The term "nitro," as used herein, refers to —NO$_2$.

The term "oxo," as used herein, refers to =O.

The term "—NR$^c$R$^d$," as used herein, refers to two groups, R$^c$ and R$^d$, which are appended to the parent molecular moiety through a nitrogen atom. R$^c$ and R$^d$ are each independently selected from the group consisting of hydrogen, alkoxyalkyl, alkoxyalkoxyalkylcarbonyl, alkoxyalkylcarbonyl, alkoxycarbonyl, alkylcarbonyl, aryl, arylalkoxycarbonyl, arylalkyl, arylalkylcarbonyl, arylcarbonyl, heteroaryl, heteroarylalkyl, heteroarylcarbonyl, heterocyclyl, heterocyclylalkyl, heterocyclylcarbonyl, and —C(O)(CH$_2$)$_n$NR$^e$R$^f$, wherein n is 0, 1, or 2 and R$^e$ and R$^f$ are independently selected from the group consisting of hydrogen and alkyl, and wherein the aryl, the aryl part of the arylalkoxycarbonyl, the arylalkyl, the arylalkylcarbonyl, and the arylcarbonyl, the heteroaryl, the heteroaryl part of the heteroarylalkyl and the heteroarylcarbonyl, the heterocyclyl, and the heterocyclyl part of the heterocyclylcarbonyl can be optionally substituted with one, two, three, four, or five substituents independently selected from the group consisting of alkoxy, alkoxycarbonyl, alkyl, alkylcarbonyl, carboxy, cyano, halo, haloalkoxy, haloalkyl, and nitro.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate,trifluoroacetate, phosphate, glutamate, bicarbonate, para-toluenesulfonate, and undecanoate. Also, suitable nitrogen atoms in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

In accordance with methods of treatment and pharmaceutical compositions of the invention, the compounds can be administered alone or in combination with other anticancer agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The anticancer effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Preferred compounds of the present invention are compounds of formula (I) where $R^1$ is hydrogen, X is $N(R^a)C(O)N(R^b)$, and $R^a$ and $R^b$ are hydrogen.

Determination of Biological Activity

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., Nature. 373:536–539) by a test compound relative to control.

KDR Tyrosine Kinase Production Using Baculovirus System:

The coding sequence for the human KDR intra-cellular domain (aa789–1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/mL, and were infected at 0.5 plaque forming units per cell (MOI). Cells were harvested at 48 hours post infection.

Purification of KDR

SF-9 cells expressing $(His)_6$KDR(aa789–1354) were lysed by adding 50 ml of Triton X-100 lysis buffer (20 mM Tris, pH 8.0, 137 mM NaCl, 10% glycerol, 1% Triton X-100, 1 mM PMSF, 10 μg/ml aprotinin, 1 μg/ml leupeptin) to the cell pellet from 1 L of cell culture. The lysate was centrifuged at 19,000 rpm in a Sorval SS-34 rotor for 30 min at 4 EC. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80 EC.

Compounds of the present invention inhibited KDR at IC50's between about 0.007 μM and about 50 μM. Preferred compounds inhibited KDR at IC50's between about 0.007 μM and about 0.5 μM. Most preferred compounds inhibited KDR at IC50's of between about 0.007 μM and about 0.1 μM.

Human Tie-2 Kinase Production and Purification

The coding sequence for the human Tie-2 intra-cellular domain (aa775–1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786–1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat # E-3641; 500 units/50 μl) and the EGF ligand was acquired from Oncogene Research Products/Calbiochem (Cat # PF011-100).

Protein Kinase Source

Lck, Fyn, Src, Blk, Csk, and Lyn, and truncated forms thereof may be commercially obtained (e.g., from Upstate Biotechnology Inc. (Saranac Lake, N.Y.) and Santa Cruz Biotechnology Inc. (Santa Cruz, Calif.)) or purified from known natural or recombinant sources using conventional methods.

Enzyme Linked Immunosorbent Assay (ELISA) for PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked lmmunosorbent Assay," In: Manual of Clinical Immunology, 2d ed., edited by Rose and Friedman, pp 359–371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly($Glu_4$ Tyr), 20,000–50,000 MW) was employed together with ATP (typically 5 μM) at concentrations approximately twice the apparent Km in the assay.

The following procedure was used to assay the inhibitory effect of compounds of this invention on KDR, Flt-1, Flt-4, Tie-1, Tie-2, EGFR, FGFR, PDGFR, IGF-1-R, c-Met, Lck, hck, Blk, Csk, Src, Lyn, fgr, Fyn and ZAP70 tyrosine kinase activity:

Buffers and Solutions:

PGTPoly (Glu,Tyr) 4:1

Store powder at $-20°$ C. Dissolve powder in phosphate buffered saline (PBS) for 50 mg/ml solution. Store 1 ml aliquots at $-20°$ C. When making plates dilute to 250 µg/ml in Gibco PBS. Reaction Buffer: 100 mM Hepes, 20 mM $MgCl_2$, 4 mM $MnCl_2$, 5 mM DTT, 0.02% BSA, 200 µM $NaVO_4$, pH 7.10

ATP: Store aliquots of 100 mM at $-20°$ C. Dilute to 20 µM in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1 M Phosphoric Acid Procedure 1. Plate Preparation:

Dilute PGT stock (50 mg/ml, frozen) in PBS to a 250 µg/ml. Add 125 µl per well of Corning modified flat bottom high affinity ELISA plates (Corning #25805-96). Add 125 µl PBS to blank wells. Cover with sealing tape and incubate overnight 37° C. Wash 1× with 250 µl washing buffer and dry for about 2 hrs in 37° C. dry incubator. Store coated plates in sealed bag at 4° C. until used.

2. Tyrosine Kinase Reaction:

Prepare inhibitor solutions at a 4× concentration in 20% DMSO in water.

Prepare reaction buffer

Prepare enzyme solution so that desired units are in 50 µl, e.g. for KDR make to 1 ng/µl for a total of 50 ng per well in the reactions. Store on ice.

Make 4× ATP solution to 20 µM from 100 mM stock in water. Store on ice

Add 50 µl of the enzyme solution per well (typically 5–50 ng enzyme/well depending on the specific activity of the kinase)

Add 25 µl 4× inhibitor

Add 25 µl 4× ATP for inhibitor assay

Incubate for 10 minutes at room temperature

Stop reaction by adding 50 µl 0.05N HCl per well

Wash plate

Final Concentrations for Reaction: 5 µM ATP, 5% DMSO

3. Antibody Binding

Dilute 1 mg/ml aliquot of PY20-HRP (Pierce) antibody(a phosphotyrosine antibody)to 50 ng/ml in 0.1% BSA in PBS by a 2 step dilution (100×, then 200×)

Add 100 µl Ab per well. Incubate 1 hr at room temp. Incubate 1 hr at 4 C.

Wash 4× plate

4. Color Reaction

Prepare TMB substrate and add 100 µl per well

Monitor OD at 650 nm until 0.6 is reached

Stop with 1M Phosphoric acid. Shake on plate reader.

Read OD immediately at 450 nm

Optimal incubation times and enzyme reaction conditions vary slightly with enzyme preparations and are determined empirically for each lot.

For Lck, the Reaction Buffer utilized was 100 mM MOPSO, pH 6.5, 4 mM $MnCl_2$, 20 mM $MgCl_2$, 5 mM DTT, 0.2% BSA, 200 mM $NaVO_4$ under the analogous assay conditions.

Compounds of the invention may have therapeutic utility in the treatment of diseases involving both identified, including those not mentioned herein, and as yet unidentified protein tyrosine kinases.

Cdc2 Source

The human recombinant enzyme and assay buffer may be obtained commercially (New England Biolabs, Beverly, Mass. USA) or purified from known natural or recombinant sources using conventional methods.

Cdc2 Assay

A protocol that can be used is that provided with the purchased reagents with minor modifications. In brief, the reaction is carried out in a buffer consisting of 50 mM Tris pH 7.5, 100 mM NaCl, 1 mM EGTA, 2 mM DTT, 0.01% Brij, 5% DMSO and 10 mM $MgCl_2$ (commercial buffer) supplemented with fresh 300 µM ATP (31 µCi/ml) and 30 µg/ml histone type IIIss final concentrations. A reaction volume of 80 µL, containing units of enzyme, is run for 20 minutes at 25 degrees C. in the presence or absence of inhibitor. The reaction is terminated by the addition of 120 µL of 10% acetic acid. The substrate is separated from unincorporated label by spotting the mixture on phosphocellulose paper, followed by 3 washes of 5 minutes each with 75 mM phosphoric acid. Counts are measured by a betacounter in the presence of liquid scintillant.

PKC Kinase Source

The catalytic subunit of PKC may be obtained commercially (Calbiochem).

PKC Kinase Assay

A radioactive kinase assay is employed following a published procedure (Yasuda, I., Kirshimoto, A., Tanaka, S., Tominaga, M., Sakurai, A., Nishizuka, Y. *Biochemical and Biophysical Research Communication* 3:166, 1220–1227 (1990)). Briefly, all reactions are performed in a kinase buffer consisting of 50 mM Tris-HCl pH7.5, 10 mM $MgCl_2$, 2 mM DTT, 1 mM EGTA, 100 µM ATP, 8 µM peptide, 5% DMSO and $^{33}P$ ATP (8 Ci/mM). Compound and enzyme are mixed in the reaction vessel and the reaction is initiated by addition of the ATP and substrate mixture. Following termination of the reaction by the addition of 10 µL stop buffer (5 mM ATP in 75 mM phosphoric acid), a portion of the mixture is spotted on phosphocellulose filters. The spotted samples are washed 3 times in 75 mM phosphoric acid at room temperature for 5 to 15 minutes. Incorporation of radiolabel is quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction is carried out in a buffer consisting of 50 mM Tris pH 7.5, 1 nM EGTA, 2 mM DTT, 0.01% Brij, 5% DMSO and 10 mM $MgCl_2$ (commercial buffer) supplemented with fresh 100 µM ATP (31 µCi/ml) and 30 µM myelin basic protein under conditions recommended by the supplier. Reaction volumes and method of assaying incorporated radioactivity are as described for the PKC assay (vide supra).

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) can be purchased from Clonetics (San Diego, Calif.) and cultured according to the manufacturer directions. Only early passages (3–8) are used for this assay. Cells are cultured in 100 mm dishes (Falcon for tissue culture; Becton Dickinson; Plymouth, England) using complete EBM media (Clonetics).

2. For evaluating a compound's inhibitory activity, cells are trypsinized and seeded at $0.5$–$1.0 \times 10^5$ cells/well in each well of 6-well cluster plates (Costar; Cambridge, Mass.).

3. 3–4 days after seeding, plates are typically 90–100% confluent. Medium is removed from all the wells, cells are rinsed with 5–10 ml of PBS and incubated 18–24 h with 5 ml of EBM base media with no supplements added (i.e., serum starvation).

4. Serial dilutions of inhibitors are added in 1 ml of EBM media (25 μM, 5 μM, or 1 μM final concentration to cells and incubated for one hour at 37° C. Human recombinant $VEGF_{165}$ (R & D Systems) is then added to all the wells in 2 ml of EBM medium at a final concentration of 50 ng/ml and incubated at 37° C. for 10 minutes. Control cells untreated or treated with VEGF only are used to assess background phosphorylation and phosphorylation induction by VEGF.

All wells are then rinsed with 5–10 ml of cold PBS containing 1 mM Sodium Orthovanadate (Sigma) and cells are lysed and scraped in 200 μl of RIPA buffer (50 mM Tris-HCl) pH7, 150 mM NaCl, 1% NP-40, 0.25% sodium deoxycholate, 1 mM EDTA) containing protease inhibitors (PMSF 1 mM, aprotinin 1 μg/ml, pepstatin 1 μg/ml, leupeptin 1 μg/ml, Na vanadate 1 mM, Na fluoride 1 mM) and 1 μg/ml of Dnase (all chemicals from Sigma Chemical Company, St Louis, Mo.). The lysate is spun at 14,000 rpm for 30 min, to eliminate nuclei.

Equal amounts of proteins are then precipitated by addition of cold (−20 C) Ethanol (2 volumes) for a minimum of 1 hour or a maximum of overnight. Pellets are reconstituted in Laemli sample buffer containing 5% -mercaptoethanol (BioRad; Hercules, Calif.) and boiled for 5 min. The proteins are resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins are probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4 C. After washing and incubating for 1 hour with HRP-conjugated $F(ab)_2$ of goat anti-rabbit or goat-anti-mouse IgG the bands are visualized using the emission chemiluminescience (ECL) system (Amersham Life Sciences, Arlington Heights, Ill.).

In Vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829–837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones can be purchased from Sigma (St. Louis, Mo.) or Cal Biochem (La Jolla, Calif.) as lyophilized powders and prepared according to supplier instructions. Vehicle components (DMSO, Cremaphor EL) can be purchased from Sigma (St. Louis, Mo.). Mice (Balb/c, 8–12 weeks old) can be purchased from Taconic (Germantown, N.Y.) and housed in a pathogen-free animal facility in accordance with institutional Animal Care and Use Committee Guidelines.

Method:

Day 1: Balb/c mice are given an intraperitoneal (i.p.) injection of 12.5 units of pregnant mare's serum gonadotropin (PMSG).

Day 3: Mice receive 15 units of human chorionic gonadotropin (hCG) i.p.

Day 4: Mice are randomized and divided into groups of 5–10. Test compounds are administered by i.p., i.v. or p.o. routes depending on solubility and vehicle at doses ranging from 1–100 mg/kg. Vehicle control group receive vehicle only and two groups are left untreated.

Thirty minutes later, experimental, vehicle and 1 of the untreated groups are given an i.p. injection of 17-estradiol (500 mg/kg). After 2–3 hours, the animals are sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri are blotted to remove fluid by pressing between two sheets of filter paper with a one liter glass bottle filled with water. Uteri are weighed following blotting (blotted weight). The difference between wet and blotted weights is taken as the fluid content of the uterus. Mean fluid content of treated groups is compared to untreated or vehicle treated groups. Significance is determined by Student's test. Non-stimulated control group is used to monitor estradiol response.

Certain compounds of this invention which are inhibitors of angiogenic receptor tyrosine kinases can also be shown active in a Matrigel implant model of neovascularization. The Matrigel neovascularization model involves the formation of new blood vessels within a clear marble of extracellular matrix implanted subcutaneously which is induced by the presence of proangiogenic factor producing tumor cells (for examples see: Passaniti, A., et al, Lab. Investig. (1992), 67(4), 519–528; Anat. Rec. (1997), 249(1), 63–73; Int. J. Cancer (1995), 63(5), 694–701; Vasc. Biol. (1995), 15(11), 1857-6). The model preferably runs over 3–4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

The compounds of the present invention may be used in the treatment of protein kinase-mediated conditions, such as benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (e.g,. kidney rejection, graft versus host disease), benign and neoplastic proliferative diseases, human cancers such as lung, breast, stomach, bladder, colon, pancreatic, ovarian, prostate and rectal cancer and hematopoietic malignancies (leukemia and lymphoma), glioblastoma, infantile hemangioma, and diseases involving inappropriate vascularization (for example diabetic retinopathy, retinopathy of prematurity, choroidal neovascularization due to age-related macular degeneration, and infantile hemangiomas in human beings). Such inhibitors may be useful in the treatment of disorders involving VEGF mediated edema, ascites, effusions, and exudates, including for example macular edema, cerebral edema, acute lung injury and adult respiratory distress syndrome (ARDS). In addition, the compounds of the invention may be useful in the treatment of pulmonary hypertension, particularly in patients with thromboembolic disease (*J. Thorac. Cardiovasc. Surg.* 2001, 122 (1), 65–73).

Synthetic Methods

Abbreviations which have been used in the descriptions of the scheme and the examples that follow are: $PPh_3$ for triphenylphosphine, dba for dibenzylideneacetone, EDCI for 1-(3-dimethylaminopropyl)-3-ethylcarbodiimide, DCC for 1,3-dicyclohexylcarbodiimide, HOBT for 1-hydroxybenzotriazole, NBS for N-bromosuccinimide, THF for tetrahydrofuran, DME for 1,2-dimethoxyethane, DMSO for dimethylsulfoxide, DMF for N,N-dimethylformamide, TFA for trifluroacetic acid, and DEAD for diethyl azodicarboxylate.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups A, X, $R^1$, $R^2$, $R^3$, $R^4$, and $R^5$ are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Scheme 1

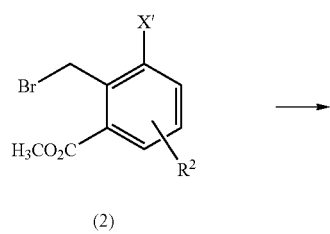

(2)

-continued

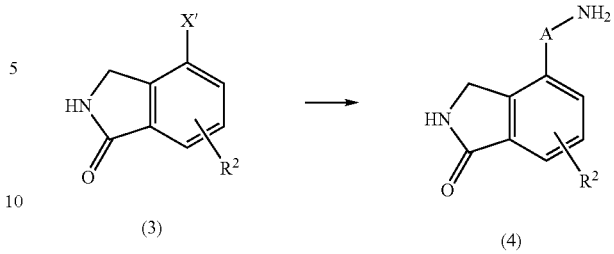

As shown in Scheme 1, compounds of formula (2) (where X' is Br or I) can be treated with ammonium hydroxide to provide compounds of formula (3). Compounds of formula (3) can be converted to compounds of formula (4) by treatment with an organometallic coupling partner (M-A-$NH_2$, where M is a metal such as a boronic acid, boronic ester, or alkyl stannane) in the presence of a palladium catalyst and optional base. Examples of palladium catalysts include $Pd(PPh_3)_4$, $PdCl_2(PPh_3)_2$, and $Pd_2(dba)_3$ with a ligand such as $PPh_3$. Representative bases include sodium carbonate, potassium carbonate, and cesium carbonate.

Compounds of formula (3) where $R^2$ is hydrogen can be converted to compounds of formula (3) where $R^2$ is nitro by treatment with nitric acid in the presence of sulfuric acid. Compounds of formula (3) where $R^2$ is nitro can be converted to compounds of formula (4) where $R^2$ is nitro by the methods described above.

Scheme 2

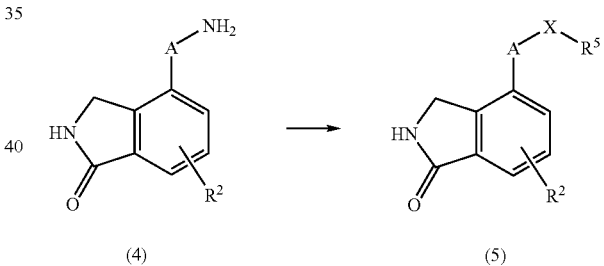

Scheme 2 shows the synthesis of compounds of formula (5). Compounds of formula (4) can be treated with an isocyanate or thioisocyanate in the presence of a base such as N-methylmorpholine or triethylamine to provide compounds of formula (5) where X is $N(R^a)C(S)N(R^b)$ or $N(R^a)C(O)N(R^b)$.

Alternatively, compounds of formula (4) can be coupled to an appropriately substituted carboxylic acid under standard coupling conditions to provide compounds of formula (5) where X is $N(R^a)C(O)$. Standard coupling conditions include a coupling agent such as EDCI or DCC, a base such as N-methylmorpholine or triethylamine, and optionally HOBT.

Compounds of formula (5) where $R^2$ is nitro can be converted to compounds of formula (5) where $R^2$ is $NH_2$ by reduction under conditions known to those of ordinary skill in the art (e.g., treatment with 10% Pd/C). Compounds of formula (5) where $R^2$ is $NH_2$ can be further functionalized through reaction with an alkylating or acylating agent in the presence of a base.

Scheme 3

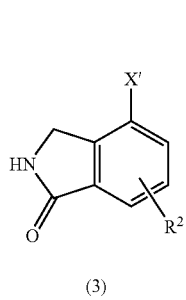

As shown in Scheme 3, compounds of formula (3) where X' is Br or I can be coupled with an appropriately substituted organometallic coupling partner (M-A-X-$R^5$, where M is a metal such as a boronic acid, a boronic ester, or an alkylstannane) under the conditions described in Scheme 1 to provide compounds of formula (5).

Scheme 4

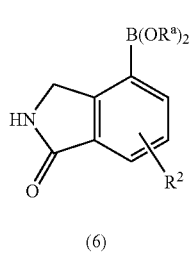

The synthesis of compounds of formula (5) is shown in Scheme 4. Compounds of formula (6) ($R^a$ is an alkyl group) can be converted to compounds of formula (5) by treatment with an appropriately substituted halide (X'-A-X-$R^5$, where X' is Br or I) under the conditions described in Scheme 1.

Scheme 5

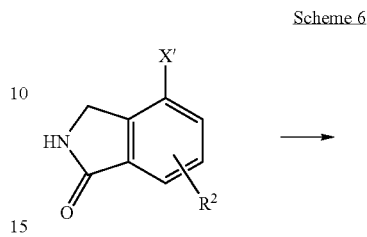

An alternative synthesis of compounds of formula (5) is shown in Scheme 5. Compounds of formula (6) can be coupled to an appropriately substituted halide (X'-A-$NH_2$, where X' is Br or I) using the conditions described in Scheme 1 to provide compounds of formula (7) which can be converted to compounds of formula (5) using the conditions described in Scheme 2.

Scheme 6

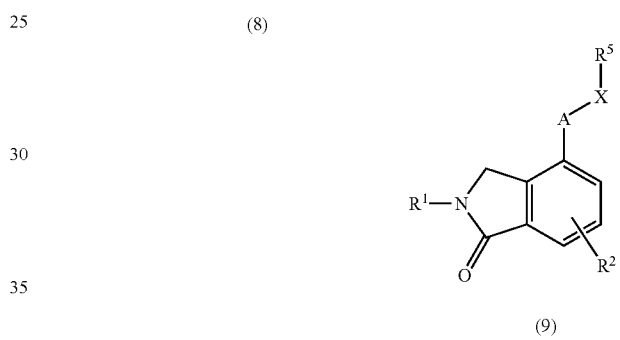

As shown in Scheme 6, compounds of formula (3) can be converted to compounds of formula (8), where $R^1$ is an alkyl group, by treatment with an alkylating agent in the presence of a base such as triethylamine or diisopropylethylamine. Compounds of formula (8) can be converted to compounds of formula (9) (where $R^1$ is alkyl) by the methods previously described.

The methods described above can also be used to prepared compounds of formula (I) where $R^3$ is hydrogen and $R^4$ is A-X-$R^5$ by substituting the appropriate starting materials.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada).

EXAMPLE 1

N-(3-methylphenyl)-N'-[4-(1-oxo-2,3-dihydro-1H-isoindol-4-yl)phenyl]urea

EXAMPLE 1A

Methyl 3-bromo-2-methylbenzoate

A suspension of 3-bromo-2-methylbenzoic acid (9.9 g, 46 mmol) in thionyl chloride (20 mL) was heated to 60° C. for 1 hour, cooled to room temperature, and concentrated. The residue was suspended in 50 mL of methanol, cooled to 0° C., treated slowly with triethylamine (12.7 µL, 92 mmol), warmed to room temperature, and concentrated. The residue was partitioned between ethyl acetate and water and the organic phase was washed with saturated $NaHCO_3$ and brine, dried ($MgSO_4$), filtered, and concentrated to give 7.39 g of the desired product. $R_f$=0.5 (10% ethyl acetate/hexanes).

EXAMPLE 1B

Methyl 3-bromo-2-(bromomethyl)benzoate

A suspension of Example 1A (7.4 g, 32.3 mmol), NBS (6.9 g, 38.8 mmol), and benzoyl peroxide (0.782 g, 3.2 mmol) in benzene (100 mL) was stirred at reflux for 5 hours, cooled to 0° C., and filtered. The solid was washed with diethyl ether and the filtrate was washed sequentially with 10% $Na_2S_2O_3$ (2×20 mL), and brine, dried ($MgSO_4$), filtered, and concentrated. The residue was purified by silica gel chromatography with 5 to 10% ethyl acetate/hexanes to give 9.32 g of the desired product. $R_f$=0.2 (5% ethyl acetate/hexanes).

EXAMPLE 1C 4-bromo-1-isoindolinone

A solution of Example 1B (8.3 g, 26.9 mmol) in THF (100 mL) was treated dropwise with concentrated $NH_4OH$ (9 mL, 135 mmol) stirred at room temperature for 2 days, diluted with 30 mL water, cooled to 0° C., and filtered. The filter cake was washed with water and ethyl acetate and dried to give 3.34 g of the desired product. MS (ESI(+)) m/e 212 $(M+H)^+$.

EXAMPLE 1D 4-(4-aminophenyl)-1-isoindolinone

A suspension of Example 1C (2 g, 9.43 mmol), 4-(4,4,5,5-tetramethyl-1,3,2-dioxa-borolan-2-yl)aniline (2.5 g, 11.3 mmol), and $Na_2CO_3$ (2.2 g, 20.8 mmol) in DME (68 mL) and water (17 mL) was purged with nitrogen, treated with $Pd(PPh_3)_4$ (1 g, 0.9 mmol), and stirred at 90° C. for 19 hours. The reaction mixture was cooled to room temperature, concentrated to one-third its original volume, diluted with ethyl acetate (30 mL) and water (20 mL), and filtered. The filter cake was washed with water and ethyl acetate and dried to give 1.25 g of the desired product. MS (ESI(+)) m/e 225 $(M+H)^+$.

EXAMPLE 1E

N-(3-methylphenyl)-N'-[4-(1-oxo-2,3-dihydro-1H-isoindol-4-yl)phenyl]urea

An 0° C. suspension of Example 1D (1.94 g, 8.68 mmol) in THF (44 mL) was sequentially treated dropwise with N-methylmorpholine (0.95 mL, 8.68 mmol) and 3-methylphenyl isocyanate (1.12 mL, 8.68 mmol). The mixture was stirred for 1 hour, diluted with THF (20 mL), stirred at room temperature for 3 hours, and quenched with water (20 mL). The organic phase was washed with brine, dried ($MgSO_4$), filtered, and concentrated. The residue was suspended in 5% methanol/dichloromethane and filtered. The filter cake was washed with dichloromethane and dried to provide 2.94 g of the desired product. 1H NMR (300 MHz, DMSO-$d_6$) δ 2.29 (s, 3H), 4.52 (s, 2H), 6.80 (d, J=7.5 Hz, 1H), 7.17 (t, J=7.6 Hz, 1H), 7.23–7.27 (m, 1H), 7.31 (s, 1H), 7.53–7.60 (m, 5H), 7.64–7.67 (m, 2H), 8.63 (s, 1H), 8.65 (s, 1H), 8.80 (s, 1H); MS (ESI(+)) m/e 358.1 $(M+H)^+$.

EXAMPLE 2

N-(3-methylphenyl)-N'-[4-(7-nitro-1-oxo-2,3-dihydro-1H-isoindol-4-yl)phenyl]urea

EXAMPLE 2A 4-bromo-7-nitro-1-isoindolinone

A 0° C. solution of Example 1C (5 g, 23.6 mmol) in 10 mL sulfuric acid was treated with a solution of concentrated nitric acid (1.55 mL, 24.7 mmol) in 10 mL sulfuric acid via addition funnel. The resulting mixture was stirred at 0° C. for 1 hour, warmed to room temperature, stirred overnight, poured over ice, and filtered. The filter cake was washed with water and diethyl ether and then dried to give 5.39 g of the desired product. $^1$H NMR (300 MHz, DMSO-$d_6$) δ 4.39 (s, 2H); 7.88 (d, J=8.1 Hz, 1H); 8.05 (d, J=8.5 Hz, 1H); 9.17 (s, 1H).

EXAMPLE 2B

N-(3-methylphenyl)-N'-[4-(7-nitro-1-oxo-2,3-dihydro-1H-isoindol-4-yl)phenyl]urea The desired product was prepared by substituting Example 2A for Example 1C and N-(3-methylphenyl)-N'-[4-(4,4,5,5-tetramethyl-1,3,2-dioxaborolan-2-yl)phenyl] urea for 4-(4,4,5,5-tetramethyl-1,3,2-dioxaborolan-2-yl) aniline in Example 1D. $^1$H NMR (300 MHz, DMSO-$d_6$) δ 2.29 (s, 3H); 4.59 (s, 2H); 6.81 (d, J=7.5 Hz, 1H); 7.17 (t, J=7.6 Hz, 1H); 7.25 (d, J=8.8 Hz, 1H); 7.31 (br s, 1H); 7.61 (apparent s, 4H); 7.80 (d, J=8.1 Hz, 1H); 7.94 (d, J=8.1 Hz, 1H); 8.67 (s, 1H); 8.89 (s, 1H); 9.05 (s, 1H); MS (ESI(+)) m/e 403 $(M+H)^+$.

EXAMPLE 3

N-[4-(7-amino-1-oxo-2,3-dihydro-1H-isoindol-4-yl) phenyl]-N'-(3-methylphenyl)urea A mixture of Example 2 (1.29 g, 3.21 mmol) and 10% Pd on carbon (100 mg) in DMF (10 mL) under a hydrogen atmosphere was stirred at room temperature overnight. The mixture was filtered through diatomaceous earth (Celite®) and the pad was washed with methanol. The filtrate was concentrated, diluted with water, cooled to 0° C., and filtered. The filter cake was washed with water and diethyl ether then dried to give 0.88 g of the desired product. $^1$H NMR (300 MHz, DMSO-$d_6$) δ 2.28 (s, 3H); 4.40 (s, 2H); 6.17 (s, 2H); 6.66 (d, J=8.5 Hz, 1H); 6.79 (d, J=7.1 Hz, 1H); 7.16 (t, J=7.6 Hz, 1H); 7.24 (d, J=8.5 Hz, 1H); 7.30–7.35 (m, 2H); 7.39 (d, J=8.8 Hz, 2H); 7.44 (d, J=8.8 Hz, 2H); 8.25 (s, 1H); 8.58 (s, 1H); 8.68 (s, 1H); MS (ESI(−)) m/e 371 (M−H)$^−$.

EXAMPLE 4

N-{7-[4-({[(3-methylphenyl)amino]carbonyl}amino) phenyl]-3-oxo-2,3-dihydro-1H-isoindol-4-yl}acetamide A suspension of Example 3 (0.088 g, 0.24 mmol) in THF (2 mL) was treated dropwise via syringe with acetyl chloride (0.017 mL, 0.24 mmol), stirred at room temperature overnight, quenched with water, cooled to 0° C., and filtered. The filter cake was dried to give 77 mg of the desired product. $^1$H NMR (300 MHz, DMSO-$d_6$) δ 2.17 (s, 3H); 2.28 (s, 3H); 4.55 (s, 2H); 6.80 (d, J=7.1 Hz, 1H); 7.16 (t, J=7.8 Hz, 1H); 7.24 (d, J=8.1 Hz, 1H); 7.31 (br s, 1H); 7.50 (d, J=8.8 Hz, 2H); 7.56 (d, J=8.8 Hz, 2H); 7.61 (d, J=8.5 Hz, 1H); 8.38 (d, J=8.1 Hz, 1H); 8.62 (s, 1H); 8.78 (s, 1H); 8.96 (s, 1H); 10.58 (s, 1H); MS (ESI(+)) m/e 415 (M+H)$^+$.

EXAMPLE 5

N-(2-methylphenyl)-N'-[4-(1-oxo-2,3-dihydro-1H-isoindol-4-yl)phenyl]urea

The desired product was prepared by substituting 2-methylphenyl isocyanate for 3-methylphenyl isocyanate in Example 1E. $^1$H NMR (500 MHz, DMSO-$d_6$) δ 2.26 (s, 3H); 4.51 (s, 2H); 6.97 (t, J=7.5 Hz, 1H); 7.1–7.2 (m, 2H); 7.5–7.7 (m, 7H); 7.83 (d, J=7.5 Hz, 1H); 7.96 (s, 1H); 8.63 (s, 1H); 9.15 (s, 1H); MS (ESI(+)) m/e 358 (M+H)$^+$.

EXAMPLE 6

N-(4-methylphenyl)-N'-[4-(1-oxo-2,3-dihydro-1H-isoindol-4-yl)phenyl]urea

The desired product was prepared by substituting 4-methylphenyl isocyanate for 3-methylphenyl isocyanate in Example 1E. $^1$H NMR (500 MHz, DMSO-$d_6$) δ 2.25 (s, 3H); 4.51 (s, 2H); 7.09 (d, J=8.4 Hz, 1H); 7.35 (d, J=8.4 Hz, 2H); 7.5–7.7 (m, 7H); 8.58 (s, 1H); 8.63 (s, 1H); 8.76 (s, 1H); MS (ESI(+)) m/e 358 (M+H)$^+$.

EXAMPLE 7

N-(2-methoxyphenyl)-N'-[4-(1-oxo-2,3-dihydro-1H-isoindol-4-yl)phenyl]urea

The desired product was prepared by substituting 2-methoxyphenyl isocyanate for 3-methylphenyl isocyanate in Example 1E. $^1$H NMR (500 MHz, DMSO-$d_6$) δ 3.89 (s, 3H); 4.51 (s, 2H); 6.91 (td, J=7.6, 1.3 Hz, 1H); 6.96 (td, J=7.6, 1.7 Hz, 1H); 7.03 (dd, J=8.1, 1.3 Hz, 1H); 7.5–7.7 (m, 7H); 8.15 (dd, J=8.0, 1.7 Hz, 1H); 8.26 (s, 1H); 8.63 (s, 1H); 9.45 (s, 1H); MS (ESI(+)) m/e 374 (M+H)$^+$.

EXAMPLE 8

N-(3-methoxyphenyl)-N'-[4-(1-oxo-2,3-dihydro-1H-isoindol-4-yl)phenyl]urea

The desired product was prepared by substituting 3-methoxyphenyl isocyanate for 3-methylphenyl isocyanate in Example 1E. $^1$H NMR (500 MHz, DMSO-$d_6$) δ 3.74 (s, 3H); 4.51 (s, 2H); 6.57 (dd, J=8.1, 1.9 Hz, 1H); 6.95 (d, J=8.1 Hz, 1H); 7.15–7.20 (m, 2H); 7.5–7.7 (m, 7H); 8.63 (s, 1H); 8.71 (s, 1H); 8.79 (s, 1H); MS (ESI(+)) m/e 374 (M+H)$^+$.

EXAMPLE 9

N-(4-methoxyphenyl)-N'-[4-(1-oxo-2,3-dihydro-1H-isoindol-4-yl)phenyl]urea

The desired product was prepared by substituting 4-methoxyphenyl isocyanate for 3-methylphenyl isocyanate in Example 1E. $^1$H NMR (500 MHz, DMSO-$d_6$) δ 3.72 (s, 3H); 4.51 (s, 2H); 6.88 (d, J=8.7 Hz, 2H); 7.37 (d, J=8.7 Hz, 2H); 7.5–7.7 (m, 7H); 8.50 (s, 1H); 8.62 (s, 1H); 8.72 (s, 1H); MS (ESI(+)) m/e 374 (M+H)$^+$.

EXAMPLE 10

N-(2-fluorophenyl)-N'-[4-(1-oxo-2,3-dihydro-1H-isoindol-4-yl)phenyl]urea

The desired product was prepared by substituting 2-fluorophenyl isocyanate for 3-methylphenyl isocyanate in Example 1E. $^1$H NMR (500 MHz, DMSO-$d_6$) δ 4.52 (m, 2H); 7.95–7.05 (m, 1H); 7.15 (t, J=7.6 Hz, 1H); 7.1–7.2 (m, 1H); 7.5–7.7 (m, 7H); 8.16 (d, J=8.4 Hz, 1H); 8.58 (m, 1H); 8.63 (s, 1H); 9.21 (s, 1H); MS (ESI(+)) m/e 362 (M+H)$^+$.

EXAMPLE 11

N-(3-fluorophenyl)-N'-[4-(1-oxo-2,3-dihydro-1H-isoindol-4-yl)phenyl]urea

The desired product was prepared by substituting 3-fluorophenyl isocyanate for 3-methylphenyl isocyanate in Example 1E. $^1$H NMR (500 MHz, DMSO-$d_6$) δ 4.51 (s, 2H); 6.79 (td, J=8.5, 2.0 Hz, 1H); 7.14 (dd, J=8.1, 2.0 Hz, 1H); 7.31 (apparent q, J=8.1 Hz, 1H); 7.50 (dt, J=11.9, 2.2 Hz, 1H); 7.55–7.60 (m, 5H); 7.6–7.7 (m, 2H); 8.63 (s, 1H); 8.88 (s, 1H); 8.94 (s, 1H); MS (ESI(+)) m/e 362 (M+H)$^+$.

EXAMPLE 12

N-(4-fluorophenyl)-N'-[4-(1-oxo-2,3-dihydro-1H-isoindol-4-yl)phenyl]urea

The desired product was prepared by substituting 4-fluorophenyl isocyanate for 3-methylphenyl isocyanate in Example 1E. $^1$H NMR (500 MHz, DMSO-$d_6$) δ 4.51 (s, 2H); 7.13 (t, J=8.9 Hz, 2H); 7.45–7.65 (m, 9H); 8.63 (s, 1H); 8.74 (s, 1H); 8.81 (s, 1H); MS (ESI(+)) m/e 362 (M+H)$^+$.

EXAMPLE 13

N-(2-chlorophenyl)-N'-[4-(1-oxo-2,3-dihydro-1H-isoindol-4-yl)phenyl]urea

The desired product was prepared by substituting 2-chlorophenyl isocyanate for 3-methylphenyl isocyanate in Example 1E. ¹H NMR (500 MHz, DMSO-d₆) δ 4.52 (s, 2H); 7.05 (d, J=8.7 Hz, 1H); 7.32 (d, J=8.7 Hz, 1H); 7.47 (dd, J=8.1, 1.6 Hz, 1H); 7.5–7.7 (m, 7H); 8.18 (dd, J=8.3, 1.4 Hz, 1H); 8.34 (s, 1H); 8.63 (s, 1H); 9.55 (s, 1H); MS (ESI(+)) m/e 378 (M+H)⁺.

EXAMPLE 14

N-(3-chlorophenyl)-N'-[4-(1-oxo-2,3-dihydro-1H-isoindol-4-yl)phenyl]urea

The desired product was prepared by substituting 3-chlorophenyl isocyanate for 3-methylphenyl isocyanate in Example 1E. ¹H NMR (300 MHz, DMSO-d₆) δ 4.52 (s, 2H); 7.0–7.1 (m, 1H); 7.25–7.35 (m, 2H); 7.5–7.8 (m, 8H); 8.66 (s, 1H); 8.91 (s, 1H); 8.94 (s, 1H); MS (ESI(+)) m/e 378 (M+H)⁺.

EXAMPLE 15

N-(4-chlorophenyl)-N'-[4-(1-oxo-2,3-dihydro-1H-isoindol-4-yl)phenyl]urea

The desired product was prepared by substituting 4-chlorophenyl isocyanate for 3-methylphenyl isocyanate in Example 1E. ¹H NMR (500 MHz, DMSO-d₆) δ 4.51 (s, 2H); 7.30–7.35 (m, 2H); 7.48–7.53 (m, 2H); 7.53–7.60 (m, 5H); 7.63–7.68 (m, 2H); 8.63 (s, 1H); 8.85 (s, 2H); MS (ESI(+)) m/e 378 (M+H)⁺.

EXAMPLE 16

N-(2-bromophenyl)-N'-[4-(1-oxo-2,3-dihydro-1H-isoindol-4-yl)phenyl]urea

The desired product was prepared by substituting 2-bromophenyl isocyanate for 3-methylphenyl isocyanate in Example 1E. ¹H NMR (500 MHz, DMSO-d₆) δ 4.52 (s, 2H); 6.99 (d, J=7.5 Hz, 1H); 7.35 (d, J=8.4 Hz, 1H); 7.5–7.7 (m, 8H); 8.08 (dd, J=8.3, 1.4 Hz, 1H); 8.17 (s, 1H); 8.63 (s, 1H); 9.60 (s, 1H); MS (ESI(+)) m/e 422, 424 (M+H)⁺.

EXAMPLE 17

N-(3-bromophenyl)-N'-[4-(1-oxo-2,3-dihydro-1H-isoindol-4-yl)phenyl]urea

The desired product was prepared by substituting 3-bromophenyl isocyanate for 3-methylphenyl isocyanate in Example 1E. ¹H NMR (300 MHz, DMSO-d₆) δ 4.52 (s, 2H); 7.1–7.2 (m, 1H); 7.25 (t, J=8.0 Hz, 1H); 7.3–7.4 (m, 1H); 7.5–7.7 (m, 7H); 7.87 (t, J=1.9 Hz, 1H); 8.66 (s, 1H); 8.91 (s, 1H); 8.92 (s, 1H); MS (ESI(+)) m/e 422, 424 (M+H)⁺.

EXAMPLE 18

N-(4-bromophenyl)-N'-[4-(1-oxo-2,3-dihydro-1H-isoindol-4-yl)phenyl]urea

The desired product was prepared by substituting 4-bromophenyl isocyanate for 3-methylphenyl isocyanate in Example 1E. ¹H NMR (500 MHz, DMSO-d₆) δ 4.51 (s, 2H); 7.46 (apparent s, 4H); 7.3–7.6 (m, 5H); 7.63–7.67 (m, 2H); 8.63 (s, 1H); 8.86 (s, 2H); MS (ESI(+)) m/e 422, 424 (M+H)⁺.

EXAMPLE 19

N-[4-(1-oxo-2,3-dihydro-1H-isoindol-4-yl)phenyl]-N'-[4-(trifluoromethoxy)phenyl]urea The desired product was prepared by substituting 4-trifluoromethoxyphenyl isocyanate for 3-methylphenyl isocyanate in Example 1E. ¹H NMR (500 MHz, DMSO-d₆) δ 4.51 (s, 2H); 7.30 (d, J=8.7 Hz, 2H); 7.5–7.6 (m, 7H); 7.6–7.7 (m, 2H); 8.63 (s, 1H); 8.87 (s, 1H); 8.92 (s, 1H); MS (ESI(+)) m/e 428 (M+H)⁺.

EXAMPLE 20

N-[4-(1-oxo-2,3-dihydro-1H-isoindol-4-yl)phenyl]-N'-(3-phenoxyphenyl)urea

The desired product was prepared by substituting 3-phenoxyphenyl isocyanate for 3-methylphenyl isocyanate in Example 1E. ¹H NMR (500 MHz, DMSO-d₆) δ 4.50 (s, 2H); 6.62 (dd, J=8.1, 1.6 Hz, 1H); 7.04 (d, J=7.5 Hz, 2H); 7.16 (t, J=7.5 Hz, 2H); 7.25–7.30 (m, 2H); 7.41 (d, J=7.5 Hz, 1H); 7.5–7.6 (m, 5H); 7.64 (t, J=7.0 Hz, 2H); 8.62 (s, 1H); 8.78 (s, 1H); 8.83 (s, 1H); MS (ESI(+)) m/e 436 (M+H)⁺.

EXAMPLE 21

N-[4-(1-oxo-2,3-dihydro-1H-isoindol-4-yl)phenyl]-N'-[4-(trifluoromethyl)phenyl]urea The desired product was prepared by substituting 4-trifluoromethylphenyl isocyanate for 3-methylphenyl isocyanate in Example 1E. ¹H NMR (300 MHz, DMSO-d₆) δ 4.52 (s, 2H); 7.5–7.7 (m, 11H); 8.66 (s, 1H); 8.96 (s, 1H); 9.16 (s, 1H); MS (ESI(+)) m/e 412 (M+H)⁺.

EXAMPLE 22

N-[4-(1-oxo-2,3-dihydro-1H-isoindol-4-yl)phenyl]-N'-(4-phenoxyphenyl)urea

The desired product was prepared by substituting 4-phenoxyphenyl isocyanate for 3-methylphenyl isocyanate in Example 1E. ¹H NMR (500 MHz, DMSO-d₆) δ 4.51 (s, 2H); 6.95–7.05 (m, 4H); 7.09 (t, J=7.3 Hz, 1H); 7.36 (t, J=8.7 Hz, 2H); 7.45–7.50 (m, 2H); 7.52–7.60 (m, 5H); 7.62–7.70 (m, 2H); 8.63 (s, 1H); 8.72 (s, 1H); 8.80 (s, 1H); MS (ESI(+)) m/e 436 (M+H)⁺.

EXAMPLE 23

N-[3-(benzyloxy)phenyl]-N'-[4-(1-oxo-2,3-dihydro-1H-isoindol-4-yl)phenyl]urea The desired product was prepared by substituting 3-benzyloxyphenyl isocyanate for 3-methylphenyl isocyanate in Example 1E. ¹H NMR (500 MHz, DMSO-d₆) δ 4.51 (s, 2H); 5.09 (s, 2H); 6.65 (dd, J=8.1, 1.9 Hz, 1H); 6.97 (dd, J=7.8, 1.3 Hz, 1H); 7.19 (t, J=8.1 Hz, 1H); 7.27 (t, J=2.2 Hz, 1H); 7.33 (t, J=7.2 Hz, 1H); 7.40 (t, J=7.3 Hz, 2H); 7.46 (d, J=7.2 Hz, 2H); 7.5–7.6 (m, 5H); 7.6–7.7 (m, 2H); 8.63 (s, 1H); 8.71 (s, 1H); 8.80 (s, 1H); MS (ESI(+)) m/e 450 (M+H)⁺.

EXAMPLE 24

N-(2,3-dimethylphenyl)-N'-[4-(1-oxo-2,3-dihydro-1H-isoindol-4-yl)phenyl]urea

The desired product was prepared by substituting 2,3-dimethylphenyl isocyanate for 3-methylphenyl isocyanate in Example 1E. $^1$H NMR (500 MHz, DMSO-$d_6$) δ 2.15 (s, 3H); 2.26 (s, 3H); 4.51 (s, 2H); 6.91 (d, J=7.5 Hz, 1H); 7.04 (t, J=7.8 Hz, 1H); 7.52–7.60 (m, 6H); 7.63–7.70 (m, 2H); 7.98 (s, 1H); 8.62 (s, 1H); 9.05 (s, 1H); MS (ESI(+)) m/e 372 (M+H)$^+$.

EXAMPLE 25

N-(2,4-dimethylphenyl)-N'-[4-(1-oxo-2,3-dihydro-1H-isoindol-4-yl)phenyl]urea

The desired product was prepared by substituting 2,4-dimethylphenyl isocyanate for 3-methylphenyl isocyanate in Example 1E. $^1$H NMR (500 MHz, DMSO-$d_6$) δ 2.22 (s, 3H); 2.24 (s, 3H); 4.51 (s, 2H); 6.9–7.0 (m, 2H); 7.5–7.7 (m, 8H); 7.88 (s, 1H); 8.62 (s, 1H); 9.06 (s, 1H); MS (ESI(+)) m/e 372 (M+H)$^+$.

EXAMPLE 26

N-(2,5-dimethylphenyl)-N'-[4-(1-oxo-2,3-dihydro-1H-isoindol-4-yl)phenyl]urea

The desired product was prepared by substituting 2,5-dimethylphenyl isocyanate for 3-methylphenyl isocyanate in Example 1E. $^1$H NMR (500 MHz, DMSO-$d_6$) δ 2.21 (s, 3H); 2.26 (s, 3H); 4.51 (s, 2H); 6.78 (d, J=7.5 Hz, 1H); 7.06 (d, J=7.5 Hz, 1H); 7.5–7.6 (m, 5H); 7.6–7.7 (m, 3H); 7.90 (s, 1H); 8.63 (s, 1H); 9.13 (s, 1H); MS (ESI(+)) m/e 372 (M+H)$^+$.

EXAMPLE 27

N-(3,4-dimethylphenyl)-N'-[4-(1-oxo-2,3-dihydro-1H-isoindol-4-yl)phenyl]urea

The desired product was prepared by substituting 3,4-dimethylphenyl isocyanate for 3-methylphenyl isocyanate in Example 1E. $^1$H NMR (300 MHz, DMSO-$d_6$) δ 2.16 (s, 3H); 2.20 (s, 3H); 4.52 (s, 2H); 7.03 (d, J=8.1 Hz, 1H); 7.1–7.3 (m, 2H); 7.5–7.7 (m, 7H); 8.52 (s, 1H); 8.65 (s, 1H); 8.75 (s, 1H); MS (ESI(+)) m/e 372 (M+H)$^+$.

EXAMPLE 28

N-(2,3-dimethoxyphenyl)-N'-[4-(1-oxo-2,3-dihydro-1H-isoindol-4-yl)phenyl]urea

The desired product was prepared by substituting 2,3-dimethoxyphenyl isocyanate for 3-methylphenyl isocyanate in Example 1E. $^1$H NMR (500 MHz, DMSO-$d_6$) δ 3.78 (s, 3H); 3.81 (s, 3H); 4.51 (s, 2H); 6.69 (dd, J=8.4, 1.3 Hz, 1H); 6.99 (t, J=8.3 Hz, 1H); 7.5–7.6 (m, 5H); 7.63–7.67 (m, 2H); 7.82 (dd, J=8.4, 1.3 Hz, 1H) 8.39 (s, 1H); 8.63 (s, 1H); 9.47 (s, 1H); MS (ESI(+)) m/e 404 (M+H)$^+$.

EXAMPLE 29

N-(2,4-dimethoxyphenyl)-N'-[4-(1-oxo-2,3-dihydro-1H-isoindol-4-yl)phenyl]urea

The desired product was prepared by substituting 2,4-dimethoxyphenyl isocyanate for 3-methylphenyl isocyanate in Example 1E. $^1$H NMR (500 MHz, DMSO-$d_6$) δ 3.74 (s, 3H); 3.87 (s, 3H); 4.51 (s, 2H); 6.49 (dd, J=8.7, 2.8 Hz, 1H); 6.63 (d, J=2.5 Hz, 1H); 7.52–7.59 (m, 5H); 7.62–7.70 (m, 2H); 7.95 (d, J=8.7 Hz, 1H); 8.02 (s, 1H); 8.62 (s, 1H); 9.29 (s, 1H); MS (ESI(+)) m/e 404 (M+H)$^+$.

EXAMPLE 30

N-(2,5-dimethoxyphenyl)-N'-[4-(1-oxo-2,3-dihydro-1H-isoindol-4-yl)phenyl]urea

The desired product was prepared by substituting 2,5-dimethoxyphenyl isocyanate for 3-methylphenyl isocyanate in Example 1E. $^1$H NMR (500 MHz, DMSO-$d_6$) δ 3.70 (s, 3H); 3.84 (s, 3H); 4.51 (s, 2H); 6.51 (dd, J=8.7, 3.1 Hz, 1H); 6.94 (d, J=8.7 Hz, 1H); 7.53–7.60 (m, 5H); 7.63–7.67 (m, 2H); 7.87 (d, J=2.8 Hz, 1H); 8.28 (s, 1H); 8.63 (s, 1H); 9.49 (s, 1H); MS (ESI(+)) m/e 404 (M+H)$^+$.

EXAMPLE 31

N-(3,4-dimethoxyphenyl)-N'-[4-(1-oxo-2,3-dihydro-1H-isoindol-4-yl)phenyl]urea

The desired product was prepared by substituting 3,4-dimethoxyphenyl isocyanate for 3-methylphenyl isocyanate in Example 1E. $^1$H NMR (500 MHz, DMSO-$d_6$) δ 3.72 (s, 3H); 3.75 (s, 3H); 4.51 (s, 2H); 6.85–6.95 (m, 2H); 7.22 (d, J=1.9 Hz, 1H); 7.5–7.6 (m, 5H); 7.62–7.66 (m, 2H); 8.54 (s, 1H); 8.63 (s, 1H); 8.72 (s, 1H); MS (ESI(+)) m/e 404 (M+H)$^+$.

EXAMPLE 32

N-(3,5-dimethoxyphenyl)-N'-[4-(1-oxo-2,3-dihydro-1H-isoindol-4-yl)phenyl]urea

The desired product was prepared by substituting 3,5-dimethoxyphenyl isocyanate for 3-methylphenyl isocyanate in Example 1E. $^1$H NMR (500 MHz, DMSO-$d_6$) δ 4.51 (s, 2H); 6.15 (s, 1H); 6.70 (d, J=2.5 Hz, 2H); 7.53–7.60 (m, 5H); 7.63–7.66 (m, 2H); 8.63 (s, 1H); 8.70 (s, 1H); 8.77 (s, 1H); MS (ESI(+)) m/e 404 (M+H)$^+$.

EXAMPLE 33

N-2,3-dihydro-1H-inden-5-yl-N'-[4-(1-oxo-2,3-dihydro-1H-isoindol-4-yl)phenyl]urea The desired product was prepared by substituting 5-isocyanatoindane for 3-methylphenyl isocyanate in Example 1E. $^1$H NMR (300 MHz, DMSO-$d_6$) δ 1.9–2.1 (m, 2H); 2.7–2.9 (m, 4H); 4.52 (s, 2H); 7.1–7.2 (m, 2H); 7.40 (s, 1H); 7.5–7.7 (m, 7H); 8.58 (s, 1H); 8.67 (s, 1H); 8.77 (s, 1H); MS (ESI(+)) m/e 384 (M+H)$^+$.

EXAMPLE 34

N-1,3-benzodioxol-5-yl-N'-[4-(1-oxo-2,3-dihydro-1H-isoindol-4-yl)phenyl]urea

The desired product was prepared by substituting 5-isocyanato-1,3-benzodioxole for 3-methylphenyl isocyanate in Example 1E. $^1$H NMR (300 MHz, DMSO-d$_6$) δ 4.52 (s, 2H); 5.98 (s, 2H); 6.75–6.90 (m, 2H); 7.22 (d, J=2.0 Hz, 1H); 7.5–7.7 (m, 7H); 8.61 (s, 1H); 8.67 (s, 1H); 8.77 (s, 1H); MS (ESI(+)) m/e 388 (M+H)$^+$.

EXAMPLE 35

N-(2,3-dichlorophenyl)-N'-[4-(1-oxo-2,3-dihydro-1H-isoindol-4-yl)phenyl]urea

The desired product was prepared by substituting 2,3-dichlorophenyl isocyanate for 3-methylphenyl isocyanate in Example 1E. $^1$H NMR (500 MHz, DMSO-d$_6$) δ 4.51 (s, 2H); 7.28–7.36 (m, 2H); 7.55–7.62 (m, 5H); 7.64–7.67 (m, 2H); 8.18 (dd, J=8.27, 1.40 Hz, 1H); 8.51 (s, 1H); 8.63 (s, 1H); 9.61 (s, 1H); MS (ESI(+)) m/e 412 (M+H)$^+$.

EXAMPLE 36

N-(2,5-dichlorophenyl)-N'-[4-(1-oxo-2,3-dihydro-1H-isoindol-4-yl)phenyl]urea

The desired product was prepared by substituting 2,5-dichlorophenyl isocyanate for 3-methylphenyl isocyanate in Example 1E. $^1$H NMR (500 MHz, DMSO-d$_6$) δ 4.52 (s, 2H); 7.11 (dd, J=8.7, 2.5 Hz, 1H); 7.51 (d, J=8.7 Hz, 1H); 7.55–7.62 (m, 5H); 7.63–7.68 (m, 2H); 8.34 (d, J=2.5 Hz, 1H); 8.50 (s, 1H); 8.63 (s, 1H); 9.66 (s, 1H); MS (ESI(+)) m/e 412 (M+H)$^+$.

EXAMPLE 37

N-(3,4-dichlorophenyl)-N'-[4-(1-oxo-2,3-dihydro-1H-isoindol-4-yl)phenyl]urea

The desired product was prepared by substituting 3,4-dichlorophenyl isocyanate for 3-methylphenyl isocyanate in Example 1E. $^1$H NMR (500 MHz, DMSO-d$_6$) δ 4.51 (s, 2H); 7.36 (dd, J=8.7, 2.5 Hz, 1H); 7.5–7.6 (m, 6H); 7.63–7.68 (m, 2H); 7.89 (d, J=2.5 Hz, 1H); 8.63 (s, 1H); 8.95 (s, 1H); 9.04 (s, 1H); MS (ESI(+)) m/e 412 (M+H)$^+$.

EXAMPLE 38

N-(3,5-dichlorophenyl)-N'-[4-(1-oxo-2,3-dihydro-1H-isoindol-4-yl)phenyl]urea

The desired product was prepared by substituting 3,5-dichlorophenyl isocyanate for 3-methylphenyl isocyanate in Example 1E. $^1$H NMR (500 MHz, DMSO-d$_6$) δ 4.51 (s, 2H); 7.17 (s, 1H); 7.55–7.60 (m, 7H); 7.63–7.70 (m, 2H); 8.63 (s, 1H); 9.03 (s, 1H); 9.10 (s, 1H); MS (ESI(+)) m/e 412 (M+H)$^+$.

EXAMPLE 39

N-[4-chloro-3-(trifluoromethyl)phenyl]-N'-[4-(1-oxo-2,3-dihydro-1H-isoindol-4-yl)phenyl]urea The desired product was prepared by substituting 4-chloro-3-trifluoromethylphenyl isocyanate for 3-methylphenyl isocyanate in Example 1E. $^1$H NMR (300 MHz, DMSO-d$_6$) δ 4.52 (s, 2H); 7.5–7.7 (m, 9H); 8.13 (d, J=2.0 Hz, 1H); 8.68 (s, 1H); 9.02 (s, 1H); 9.23 (s, 1H); (ESI(−)) m/e 444 (M−H)$^-$.

EXAMPLE 40

N-(3-chloro-4-methoxyphenyl)-N'-[4-(1-oxo-2,3-dihydro-1H-isoindol-4-yl)phenyl]urea The desired product was prepared by substituting 3-chloro-4-methoxyphenyl isocyanate for 3-methylphenyl isocyanate in Example 1E. $^1$H NMR (300 MHz, DMSO-d$_6$) δ 3.79 (s, 3H); 4.50 (s, 2H); 7.08 (d, J=9.2 Hz, 1H); 7.27 (dd, J=9.0, 3.0 Hz, 1H); 7.59 (m, 8H); 8.64 (s, 1H); 8.67 (s, 1H); 8.81 (s, 1H); MS (ESI(+)) m/e 408 (M+H)$^+$.

EXAMPLE 41

N-(4-bromo-3-methylphenyl)-N'-[4-(1-oxo-2,3-dihydro-1H-isoindol-4-yl)phenyl]urea The desired product was prepared by substituting 4-bromo-3-methylphenyl isocyanate for 3-methylphenyl isocyanate in Example 1E. $^1$H NMR (300 MHz, DMSO-d$_6$) δ 2.32 (s, 3H); 4.52 (s, 2H); 7.27 (dd, J=8.82, 2.71 Hz, 1H); 7.4–7.7 (m, 9H); 8.67 (s, 1H); 8.80 (s, 1H); 8.87 (s, 1H); MS (ESI(+)) m/e 436 (M+H)$^+$.

EXAMPLE 42

N-(3-chloro-4-fluorophenyl)-N'-[4-(1-oxo-2,3-dihydro-1H-isoindol-4-yl)phenyl]urea The desired product was prepared by substituting 3-chloro-4-fluorophenyl isocyanate for 3-methylphenyl isocyanate in Example 1E. $^1$H NMR (300 MHz, DMSO-d$_6$) δ 4.52 (s, 2H); 7.3–7.4 (m, 2H); 7.5–7.7 (m, 7H); 7.8–7.9 (m, 1H); 8.66 (s, 1H); 8.92 (s, 1H); 8.93 (s, 1H); MS (ESI(+)) m/e 396 (M+H)$^+$.

EXAMPLE 43

N-(3-chloro-4-methylphenyl)-N'-[4-(1-oxo-2,3-dihydro-1H-isoindol-4-yl)phenyl]urea The desired product was prepared by substituting 3-chloro-4-methylphenyl isocyanate for 3-methylphenyl isocyanate in Example 1E. $^1$H NMR (300 MHz, DMSO-d$_6$) δ 2.27 (s, 3H); 4.52 (s, 2H); 7.2–7.3 (m, 2H); 7.5–7.8 (m, 8H); 8.66 (s, 1H); 8.81 (s, 1H); 8.86 (s, 1H); MS (ESI(+)) m/e 392 (M+H)$^+$.

EXAMPLE 44

N-[4-(1-oxo-2,3-dihydro-1H-isoindol-4-yl)phenyl]-N'-[3-(trifluoromethyl)phenyl]urea The desired product was prepared by substituting 3-trifluoromethylphenyl isocyanate for 3-methylphenyl isocyanate in Example 1E. $^1$H NMR (300 MHz, DMSO-d$_6$) δ 4.52 (s, 1H); 7.33 (d, J=7.5 Hz, 1H); 7.5–7.7 (m, 9H); 8.04 (s, 1H); 8.66 (s, 1H); 8.95 (s, 1H); 9.10 (s, 1H); MS (ESI(+)) m/e 412 (M+H)$^+$.

EXAMPLE 45

N-(3-ethylphenyl)-N'-[4-(1-oxo-2,3-dihydro-1H-isoindol-4-yl)phenyl]urea

The desired product was prepared by substituting 3-ethylphenyl isocyanate for 3-methylphenyl isocyanate in Example 1E. $^1$H NMR (300 MHz, DMSO-d$_6$) δ 1.19 (t, J=7.6 Hz, 3H); 2.58 (q, J=7.57 Hz, 2H); 4.52 (s, 2H); 6.84 (d, J=7.5 Hz, 1H); 7.19 (t, J=7.8 Hz, 1H); 7.27 (d, J=8.5 Hz, 1H); 7.34 (s, 1H); 7.61 (m, 7H); 8.65 (s, 2H); 8.79 (s, 1H); MS (ESI(+)) m/e 372 (M+H)$^+$.

EXAMPLE 46

N-(3-cyanophenyl)-N'-[4-(1-oxo-2,3-dihydro-1H-isoindol-4-yl)phenyl]urea

The desired product was prepared by substituting 3-cyanophenyl isocyanate for 3-methylphenyl isocyanate in Example 1E. $^1$H NMR (300 MHz, DMSO-d$_6$) δ 4.52 (s, 2H); 7.4–7.8 (m, 10H); 7.99 (s, 1H); 8.66 (s, 1H); 9.00 (s, 1H); 9.08 (s, 1H); MS (ESI(+)) m/e 369 (M+H)$^+$.

EXAMPLE 47

Methyl 3-[({[4-(1-oxo-2,3-dihydro-1H-isoindol-4-yl)phenyl]amino}carbonyl)amino]benzoate The desired product was prepared by substituting methyl 3-isocyanatobenzoate for 3-methylphenyl isocyanate in Example 1E. $^1$H NMR (300 MHz, DMSO-d$_6$) δ 3.87 (s, 3H); 4.52 (s, 2H); 7.44 (t, J=7.8 Hz, 1H); 7.5–7.7 (m, 9H); 8.22 (t, J=1.0 Hz, 1H); 8.66 (s, 1H); 8.87 (s, 1H); 9.00 (s, 1H); MS (ESI(+)) m/e 419 (M+H)$^+$.

EXAMPLE 48

N-(3-acetylphenyl)-N'-[4-(1-oxo-2,3-dihydro-1H-isoindol-4-yl)phenyl]urea

The desired product was prepared by substituting 3-acetylphenyl isocyanate for 3-methylphenyl isocyanate in Example 1E. $^1$H NMR (300 MHz, DMSO-d$_6$) δ 2.58 (s, 3H); 4.52 (s, 2H); 7.45 (t, J=7.8 Hz, 1H); 7.5–7.7 (m, 9H); 8.09 (t, J=2.0 Hz, 1H); 8.66 (s, 1H); 8.88 (s, 1H); 8.96 (s, 1H); MS (ESI(+)) m/e 386 (M+H)$^+$.

EXAMPLE 49

N-[2-fluoro-5-(trifluoromethyl)phenyl]-N'-[4-(1-oxo-2,3-dihydro-1H-isoindol-4-yl)phenyl]urea The desired product was prepared by substituting 2-fluoro-5-trifluoromethylphenyl isocyanate for 3-methylphenyl isocyanate in Example 1E. $^1$H NMR (300 MHz, DMSO-d$_6$) δ 4.52 (s, 2H); 7.3–7.7 (m, 9H); 8.6–8.7 (m, 2H); 8.94 (d, J=2.7 Hz, 1H); 9.32 (s, 1H); MS (ESI(+)) m/e 430 (M+H)$^+$.

EXAMPLE 50

N$^2$,N$^2$-dimethyl-N'-{7-[4-({[(3-methylphenyl)amino]carbonyl}amino)phenyl]-3-oxo-2,3-dihydro-1H-isoindol-4-yl}glycinamide The desired product was prepared by substituting N,N-dimethylglycyl chloride for acetyl chloride in Example 4. $^1$H NMR (300 MHz, DMSO-d$_6$) δ 2.28 (s, 3H); 2.87 (br s, 6H); 4.35 (br s, 2H); 4.59 (s, 2H); 6.80 (d, J=6.8 Hz, 1H); 7.16 (t, J=7.8 Hz, 1H); 7.25 (d, J=8.1 Hz, 1H); 7.31 (br s, 1H); 7.53 (d, J=8.8 Hz, 1H); 7.58 (d, J=8.8 Hz, 1H); 7.69 (d, J=8.5 Hz, 1H); 8.31 (d, J=8.5 Hz, 1H); 8.68 (s, 1H); 8.86 (s, 1H); 9.05 (s, 1H); 9.89 (br s, 1H); 10.87 (br s, 1H); MS (ESI(+)) m/e 458 (M+H)$^+$.

EXAMPLE 51

N-{7-[4-({[(3-methylphenyl)amino]carbonyl}amino)phenyl]-3-oxo-2,3-dihydro-1H-isoindol-4-yl}nicotinamide The desired product was prepared by substituting nicotinoyl chloride for acetyl chloride in Example 4. $^1$H NMR (300 MHz, DMSO-d$_6$) δ 2.29 (s, 3H); 4.63 (s, 2H); 6.80 (d, J=7.8 Hz, 1H); 7.17 (t, J=7.6 Hz, 1H); 7.25 (d, J=8.5 Hz, 1H); 7.31 (br s, 1H); 7.5–7.6 (m, 4H); 7.67 (dd, J=7.8, 4.8 Hz, 1H); 7.73 (d, J=8.1 Hz, 1H); 8.32 (dt, J=8.1, 1.7 Hz, 1H); 8.53 (d, J=8.5 Hz, 1H); 8.63 (s, 1H); 8.80 (s, 1H); 8.84 (dd, J=4.8, 1.4 Hz, 1H); 9.1–9.2 (m, 2H); 11.78 (s, 1H); MS (ESI(+)) m/e 478 (M+H)$^+$.

EXAMPLE 52

N-{7-[4-({[(3-methylphenyl)amino]carbonyl}amino)phenyl]-3-oxo-2,3-dihydro-1H-isoindol-4-yl}-2-phenylacetamide The desired product was prepared by substituting phenylacetyl chloride for acetyl chloride in Example 4. $^1$H NMR (300 MHz, DMSO-d$_6$) δ 2.28 (s, 3H); 3.79 (s, 2H); 4.53 (s, 2H); 6.80 (d, J=7.1 Hz, 1H); 7.1–7.6 (m, 15H); 8.37 (d, J=8.5 Hz, 2H); 8.62 (s, 1H); 8.78 (s, 1H); 8.89 (s, 1H); 10.71 (s, 1H); MS (ESI(−)) m/e 489 (M−H)$^-$.

EXAMPLE 53

2-(2-methoxyethoxy)-N-{7-[4-({[(3-methylphenyl)amino]carbonyl}amino)phenyl]-3-oxo-2,3-dihydro-1H-isoindol-4-yl}acetamide The desired product was prepared by substituting (2-methoxyethoxy)acetyl chloride for acetyl chloride in Example 4. $^1$H NMR (300 MHz, DMSO-d$_6$) δ 2.28 (s, 3H); 3.40–3.45 (m, 2H); 3.50–3.55 (m, 2H); 4.15 (s, 2H); 4.56 (s, 2H); 6.80 (d, J=7.5 Hz, 1H); 7.16 (t, J=7.8 Hz, 1H); 7.24 (d, J=8.5 Hz, 1H); 7.31 (br s, 1H); 7.51 (d, J=9.2 Hz, 2H); 7.56 (d, J=9.2 Hz, 1H); 7.63 (d, J=8.5 Hz, 1H); 8.49 (d, J=8.5 Hz, 1H); 8.62 (s, 1H); 8.78 (s, 1H); 8.89 (s, 1H); 11.35 (s, 1H); MS (ESI(+)) m/e 489 (M+H)$^+$.

EXAMPLE 54

N-(3-methylphenyl)-N'-[6-(1-oxo-2,3-dihydro-1H-isoindol-4-yl)-3-pyridinyl]urea

EXAMPLE 54A 4-(4,4,5,5-tetramethyl-1,3,2-dioxaborolan-2-yl)-1-isoindolinone

A suspension of Example 1C (10.6 g, 50 mmol) and 4,4,5,5,4',4',5',5'-octamethyl-[2,2']bi[[1,3,2]dioxaborolanyl] (15.23 g, 60 mmol) in DMF (390 mL) was stirred until a clear yellow solution was obtained. The solution was then treated with potassium acetate (14.72 g, 150 mmol), degassed with nitrogen, treated with [1.1'-bis(diphenylphosphino)-ferrocene]dichloropalladium [II].$CH_2Cl_2$ (7 g, 8.5 mmol) and heated to 90° C. overnight. The reaction was cooled to room temperature and filtered through diatomaceous earth (Celite®), and concentrated. The concentrate was partitioned between water and ethyl acetate and filtered through diatomaceous earth (Celite®). The organic phase was dried ($Na_2SO_4$), filtered, and concentrated. The crude product was purified by silica gel chromatography eluting with 100% ethyl acetate and triturated from hexanes to give 4.56 g (35% yield) of the desired product. m.p.: 189–191° C.

EXAMPLE 54B

N-(3-methylphenyl)-N'-[6-(1-oxo-2,3-dihydro-1H-isoindol-4-yl)-3-pyridinyl]urea

A solution of Example 54A (259 mg, 1 mmol) and N-(6-bromo-3-pyridinyl)-N'-(3-methylphenyl)urea (367 mg, 1.2 mmol) (prepared from 2-amino-4-bromopyridine and m-tolylisocyanate following the procedure of Example 1E) in toluene (6 mL) and ethanol (6 mL) was degassed with $N_2$ then treated sequentially with a solution of $Na_2CO_3$ (509 mg, 4.8 mmol) in water (3 mL) and tetrakis(triphenylphosphine)palladium (0) (208 mg, 0.187 mmol) and stirred at reflux overnight. The resulting suspension was cooled to room temperature, diluted with diethyl ether, and filtered. The filter cake was washed with water, diethyl ether, dichloromethane, ethyl acetate, and methanol. The combined filtrates were concentrated to give 51 mg of the desired product. $^1$H NMR (300 MHz, DMSO-$d_6$) δ 10.35 (s,1H), 9.58 (s,1H), 8.73 (s, 1H), 8.56 (s,1H), 8.06 (d, J=6 Hz, 1H), 7.56–7.81 (m, 4H), 7.3–7.46 (m, 2H), 7.20 (t, J=6 Hz, 1H), 6.85 (d, J=6 Hz, 1H), 4.56 (s, 2H), 2.31 (s,3H); MS (ESI(+)) m/e 359 (M+H)$^+$.

EXAMPLE 55

4-(4-phenoxyphenyl)-1-isoindolinone

EXAMPLE 55A 4-iodo-1-isoindolinone

The desired product was prepared by substituting 3-iodo-2-methylbenzoic acid for 3-bromo-2-methylbenzoic acid in Examples 1A,1B, and 1C. MS (DCI(+)) m/e 277 (M+$NH_4$)$^+$.

EXAMPLE 55B 4-(4-phenoxyphenyl)-1-isoindolinone

A suspension of Example 55A (301 mg, 1.16 mmol), 4-phenoxyphenylboronic acid (271 mg, 1.27 mmol) and $Na_2CO_3$ (403 mg, 4.75 mmol) in DME (10 mL), water (4.8 mL), and ethanol (2.4 mL) was degassed with $N_2$ for 45 minutes, treated with Pd(PPh$_3$)$_4$ (120 mg), and heated to 80° C. overnight. The suspension was cooled to room temperature, poured into water, and extracted with ethyl acetate. The combined extracts were dried ($Na_2SO_4$), filtered, and concentrated. The concentrate was triturated with warm ethanol to give 183 mg of the desired product. $^1$H NMR (300 MHz, DMSO-$d_6$) δ 4.51 (s, 2H); 7.07–7.13 (m, 3H); 7.20 (t, J=7.5 Hz, 1H); 7.33 (t, J=7.1 Hz, 1H); 7.38–7.47 (m, 3H); 7.59 (t, J=7.5 Hz, 1H); 7.62–7.69 (m, 3H); 8.69 (s, 1H); MS (ESI(+)) m/e 302.1 (M+H)$^+$.

EXAMPLE 56

4-{4-[(5,7-dimethyl-1,3-benzoxazol-2-yl)amino]-3-fluorophenyl}-1-isoindolinone

The desired product was prepared by substituting N-[2-fluoro-4-(4,4,5,5-tetramethyl-1,3,2-dioxaborolan-2-yl)phenyl]-5,7-dimethyl-1,3-benzoxazol-2-amine for 4-phenoxyphenylboronic acid in Example 55B. $^1$H NMR (300 MHz, DMSO-$d_6$) δ 2.34 (s, 3H); 2.40 (s, 3H); 4.58 (s, 2H); 6.80 (s, 1H); 7.10 (s, 1H); 7.53 (dd, J=8.5, 1.7 Hz, 1H); 7.58–7.63 (m, 2H); 7.69 (d, J=2.4 Hz, 1H); 7.72 (dd, J=3.4, 1.0 Hz, 1H); 8.43 (t, J=8.5 Hz, 1H); 8.72 (s, 1H); 10.54 (s, 1H); MS (ESI(+)) m/e 388.1 (M+H)$^+$.

EXAMPLE 57

N-[2-fluoro-4-(1-oxo-2,3-dihydro-1H-isoindol-4-yl)phenyl]-N-(3-methylphenyl)urea

EXAMPLE 57A 4-(4-amino-3-fluorophenyl)-1-isoindolinone

The desired product was prepared by substituting Example 54A and 4-bromo-2-fluoroaniline for 4-phenoxyphenylboronic acid and Example 55A, respectively, in Example 55B. MS (ESI(+)) m/e 241 (M+H)$^+$.

EXAMPLE 57B

N-[2-fluoro-4-(1-oxo-2,3-dihydro-1H-isoindol-4-yl)phenyl]-N'-(3-methylphenyl)urea The desired product was prepared by substituting Example 57A for Example 1D in Example 1E. $^1$H NMR (300 MHz, DMSO-$d_6$) δ 2.29 (s, 3H); 4.55 (s, 2H); 6.82 (d, J=7.8 Hz, 1H); 7.18 (t, J=7.6 Hz, 1H); 7.24–7.26 (m, 1H); 7.31 (s, 1H); 7.42 (dd, J=9.0, 1.5 Hz, 1H); 7.54–7.61 (m, 2H); 7.67–7.69 (m, 2H); 8.29 (t, J=8.7 Hz, 1H); 8.68 (m, J=5.1 Hz, 2H); 9.04 (s, 1H); MS (ESI(+)) m/e 376.1 (M+H)$^+$.

EXAMPLE 58

N-(3-chlorophenyl)-N-[2-fluoro-4-(1-oxo-2,3-dihydro-1H-isoindol-4-yl)phenyl]urea The desired product was prepared by substituting Example 57A for Example 1D and 3-chlorophenyl isocyanate for 3-methylphenyl isocyanate in Example 1E. $^1$H NMR (300 MHz, DMSO-$d_6$) δ 4.55 (s, 2H); 7.06 (ddd, J=7.7, 2.0, 1.2 Hz, 1H); 7.26 (m, 1H); 7.33 (t, J=8.0 Hz, 1H); 7.43 (dd, J=8.5, 1.7 Hz, 1H); 7.55–7.61 (m, 2H); 7.70–7.67 (m, 2H); 7.75 (t, J=2.0 Hz, 1H); 8.25 (t, J=8.5 Hz, 1H); 8.68 (s, 1H); 8.75 (d, J=2.4 Hz, 1H); 9.30 (s, 1H); MS (ESI(+)) m/e 396.0 (M+H)$^+$.

EXAMPLE 59

N-[2-fluoro-4-(1-oxo-2,3-dihydro-1H-isoindol-4-yl)phenyl]-N'-[4-fluoro-3-(trifluoromethyl)phenyl]urea The desired product was prepared by substituting Example 57A for Example 1D and 3-trifluoromethyl-4-fluorophenyl isocyanate for 3-methylphenyl isocyanate in Example 1E. $^1$H NMR (300 MHz, DMSO-d$_6$) δ 4.55 (s, 2H); 7.42–7.50 (m, 2H); 7.56–7.67 (m, 3H); 7.68–7.70 (m, 2H); 8.03 (dd, J=6.4, 2.7 Hz, 1H); 8.23 (t, J=8.5 Hz, 1H); 8.69 (s, 1H); 8.77 (d, J=2.0 Hz, 1H); 9.44 (s, 1H); MS (ESI(+)) m/e 448.1 (M+H)$^+$.

EXAMPLE 60

N-(4-chlorophenyl)-N'-[2-fluoro-4-(1-oxo-2,3-dihydro-1H-isoindol-4-yl)phenyl]urea The desired product was prepared by substituting Example 57A for Example 1D and 4-chlorophenyl isocyanate for 3-methylphenyl isocyanate in Example 1E. $^1$H NMR (300 MHz, DMSO-d$_6$) δ 4.55 (s, 2H); 7.36 (d, J=8.8 Hz, 2H); 7.43 (dd, J=8.7, 1.5 Hz, 1H); 7.51 (d, J=8.8 Hz, 2H); 7.55–7.61 (m, 2H); 7.67–7.70 (m, 2H); 8.26 (t, J=8.7 Hz, 1H); 8.68 (s, 1H); 8.71 (d, J=2.4 Hz, 1H); 9.24 (s, 1H); MS (ESI(+)) m/e 396.0 (M+H)$^+$.

EXAMPLE 61

N-(3-bromophenyl)-N'-[2-fluoro-4-(1-oxo-2,3-dihydro-1H-isoindol-4-yl)phenyl]urea The desired product was prepared by substituting Example 57A for Example 1D and 3-bromophenyl isocyanate for 3-methylphenyl isocyanate in Example 1E. $^1$H NMR (300 MHz, DMSO-d$_6$) δ 4.55 (s, 2H); 7.19 (dt, J=7.0, 2.1 Hz, 1H); 7.24–7.30 (m, 2H); 7.43 (dd, J=8.5, 1.7 Hz, 1H); 7.55–7.61 (m, 2H); 7.67–7.70 (m, 2H); 7.89 (s, 1H); 8.25 (t, J=8.5 Hz, 1H); 8.69 (s, 1H); 8.74 (d, J=2.4 Hz, 1H); 9.29 (s, 1H); MS (ESI(+)) m/e 439.9, 441.9 (M+H)$^+$.

EXAMPLE 62

N-(3,4-dimethylphenyl)-N'-[2-fluoro-4-(1-oxo-2,3-dihydro-1H-isoindol-4-yl)phenyl]urea The desired product was prepared by substituting Example 57A for Example 1D and 3,4-dimethylphenyl isocyanate for 3-methylphenyl isocyanate in Example 1E. $^1$H NMR (300 MHz, DMSO-d$_6$) δ 2.17 (s, 3H); 2.20 (s, 3H); 4.55 (s, 2H); 7.05 (d, J=8.1 Hz, 1H); 7.19 (dd, J=8.1, 2.4 Hz, 1H); 7.24 (d, J=2.0 Hz, 1H); 7.41 (dd, J=8.5, 1.4 Hz, 1H); 7.53–7.61 (m, 2H); 7.67–7.69 (m, 2H); 8.29 (t, J=8.6 Hz, 1H); 8.63 (d, J=2.7 Hz, 1H); 8.68 (s, 1H); 8.94 (s, 1H); MS (ESI(+)) m/e 390.1 (M+H)$^+$.

EXAMPLE 63

N-(3-methylphenyl)-N'-[4-(1-oxo-2,3-dihydro-1H-isoindol-4-yl)-2-(trifluoromethoxy)phenyl]urea

EXAMPLE 63A

4-[4-amino-3-(trifluoromethoxy)phenyl]-1-isoindolinone

The desired product was prepared by substituting Example 54A and 2-trifluoromethoxy-4-bromoaniline for 4-phenoxyphenylboronic acid and Example 55A, respectively in Example 55B. MS (ESI(+)) m/e 309 (M+H)$^+$.

EXAMPLE 63B

N-(3-methylphenyl)-N'-[4-(1-oxo-2,3-dihydro-1H-isoindol-4-yl)-2-(trifluoromethoxy)phenyl]urea The desired product was prepared by substituting Example 63A for Example 1D in Example 1E. $^1$H NMR (300 MHz, DMSO-d$_6$) δ 2.30 (s, 3H); 4.54 (s, 2H); 6.84 (d, J=7.1 Hz, 1H); 7.19 (t, J=7.8 Hz, 1H); 7.25–7.28 (m, 1H); 7.33 (s, 1H); 7.58–7.64 (m, 3H); 7.69–7.71 (m, 2H); 8.41 (d, J=8.8 Hz, 1H); 8.59 (s, 1H); 8.68 (s, 1H); 9.26 (s, 1H); MS (ESI(+)) m/e 442.0 (M+H)$^+$.

EXAMPLE 64

N-(3-chlorophenyl)-N'-[4-(1-oxo-2,3-dihydro-1H-isoindol-4-yl)-2-(trifluoromethoxy)phenyl]urea The desired product was prepared by substituting Example 63A for Example 1D and 3-chlorophenyl isocyanate for 3-methylphenyl isocyanate in Example 1E. $^1$H NMR (300 MHz, DMSO-d$_6$) δ 4.54 (s, 2H); 7.07 (ddd, J=7.8, 2.0, 1.0 Hz, 1H); 7.27 (d, J=8.8 Hz, 1H); 7.35 (t, J=8.0 Hz, 1H); 7.58–7.71 (m, 5H); 7.76 (t, J=2.0 Hz, 1H); 8.38 (d, J=9.2 Hz, 1H); 8.66 (s, 1H); 8.68 (s, 1H); 9.51 (s, 1H); MS (ESI(+)) m/e 462.0 (M+H)$^+$.

EXAMPLE 65

N-(3,5-dimethylphenyl)-N'-[4-(1-oxo-2,3-dihydro-1H-isoindol-4-yl)phenyl]urea

The desired product was prepared by substituting 3,5-dimethylphenyl isocyanate for 3-methylphenyl isocyanate in Example 1E. $^1$H NMR (300 MHz, DMSO-d$_6$) δ 2.24 (s, 6H); 4.52 (s, 2H); 6.63 (s, 1H); 7.09 (s, 2H); 7.52–7.59 (m, 5H); 7.64–7.67 (m, 2H); 8.55 (s, 1H); 8.65 (s, 1H); 8.78 (s, 1H); MS (ESI(+)) m/e 372.1 (M+H)$^+$.

EXAMPLE 66

N-[4-(1-oxo-2,3-dihydro-1H-isoindol-4-yl)phenyl]-N'-phenylurea

The desired product was prepared by substituting phenyl isocyanate for 3-methylphenyl isocyanate in Example 1E. $^1$H NMR (300 MHz, DMSO-d$_6$) δ 4.52 (s, 2H); 6.98 (t, J=7.3 Hz, 1H); 7.29 (t, J=8.0 Hz, 2H); 7.47 (d, J=7.8 Hz, 2H); 7.53–7.60 (m, 5H); 7.64–7.67 (m, 2H); 8.65 (s, 1H); 8.71 (s, 1H); 8.82 (s, 1H); MS (ESI(−)) m/e 342.1 (M−H)$^-$.

EXAMPLE 67

N-[4-fluoro-3-(trifluoromethyl)phenyl]-N'-[4-(1-oxo-2,3-dihydro-1H-isoindol-4-yl)phenyl]urea The desired product was prepared by substituting 4-fluoro-3-trifluoromethylphenyl isocyanate for 3-methylphenyl isocyanate in Example 1E. $^1$H NMR (300 MHz, DMSO-d$_6$) δ 4.52 (s, 2H); 7.45 (app t, J=10.2 Hz, 1H); 7.54–7.61 (m, 5H); 7.64–7.69 (m, 3H); 8.02 (dd, J=6.4, 2.7 Hz, 1H); 8.66 (s, 1H); 8.97 (s, 1H); 9.09 (s, 1H); MS (ESI(+)) m/e 430.1 (M+H)$^+$.

EXAMPLE 68

N-[2-methyl-4-(1-oxo-2,3-dihydro-1H-isoindol-4-yl)phenyl]-N'-(3-methylphenyl)urea

EXAMPLE 68A 4-(4-Amino-3-methyl-phenyl-2,3-dihydro-isoindol-1-one

The desired product was prepared by substituting Example 54A and 2-methyl-4-bromoaniline for 4-phenoxyphenylboronic acid and Example 55A, respectively, in Example 55B MS (ESI(+)) m/e 239 (M+H)$^+$.

EXAMPLE 68B

N-[2-methyl-4-(1-oxo-2,3-dihydro-1H-isoindol-4-yl)phenyl]-AP-(3-methylphenyl)urea The desired product was prepared by substituting Example 68A for Example 1D in Example 1E. $^1$H NMR (300 MHz, DMSO-d$_6$) δ 2.29 (s, 3H); 2.32 (s, 3H); 4.53 (s, 2H); 6.80 (d, J=7.1 Hz, 1H); 7.17 (t, J=7.8 Hz, 1H); 7.25 (d, J=8.5 Hz, 1H); 7.33 (s, 1H); 7.42 (dd, J=8.5, 2.4 Hz, 1H); 7.45 (d, J=1.4 Hz, 1H); 7.57 (m, 1H); 7.65 (m, 2H); 8.02 (m, J=8.5 Hz, 2H); 8.67 (s, 1H); 9.03 (s, 1H); MS (ESI(+)) m/e 372.1 (M+H)$^+$.

EXAMPLE 69

N-(3-chlorophenyl)-N'-[2-methyl-4-(1-oxo-2,3-dihydro-1H-isoindol-4-yl)phenyl]urea The desired product was prepared by substituting Example 68A for Example 1D and 3-chlorophenyl isocyanate for 3-methylphenyl isocyanate in Example 1E. $^1$H NMR (300 MHz, DMSO-d$_6$) δ 2.33 (s, 3H); 4.53 (s, 2H); 7.01–7.05 (m, 1H); 7.24–7.27 (m, 1H); 7.32 (t, J=8.0 Hz, 1H); 7.43 (dd, J=8.5, 2.4 Hz, 1H); 7.46 (s, 1H); 7.57 (t, J=7.5 Hz, 1H); 7.63–7.67 (m, 2H); 7.77 (t, J=2.0 Hz, 1H); 7.97 (d, J=8.1 Hz, 1H); 8.11 (s, 1H); 8.68 (s, 1H); 9.30 (s, 1H); MS (ESI(+)) m/e 392.0 (M+H)$^+$.

EXAMPLE 70

N-(3,4-dimethylphenyl)-N'-[2-methyl-4-(1-oxo-2,3-dihydro-1H-isoindol-4-yl)phenyl]urea The desired product was prepared by substituting Example 68A for Example 1D and 3,4-dimethylphenyl isocyanate for 3-methylphenyl isocyanate in Example 1E. $^1$H NMR (300 MHz, DMSO-d$_6$) δ 2.16 (s, 3H); 2.20 (s, 3H); 2.32 (s, 3H); 4.52 (s, 2H); 7.04 (d, J=8.1 Hz, 1H); 7.19 (dd, J=8.1, 1.7 Hz, 1H); 7.25 (d, J=1.7 Hz, 1H); 7.40 (dd, J=8.1, 1.7 Hz, 1H); 7.44 (d, J=1.7 Hz, 1H); 7.54–7.59 (m, 1H); 7.63–7.66 (m, 2H); 7.96 (s, 1H); 8.02 (d, J=8.5 Hz, 1H); 8.65 (s, 1H); 8.92 (s, 1H); MS (ESI(+)) m/e 386.1 (M+H)$^+$.

EXAMPLE 71

N-[4-fluoro-3-(trifluoromethyl)phenyl]-N'-[2-methyl-4-(1-oxo-2,3-dihydro-1H-isoindol-4-yl)phenyl]urea The desired product was prepared by substituting Example 68A for Example 1D and 4-fluoro-3-trifluoromethylphenyl isocyanate for 3-methylphenyl isocyanate in Example 1E. $^1$H NMR (300 MHz, DMSO-d$_6$) δ 2.33 (s, 3H); 4.52 (s, 2H); 7.45 (m, 3H); 7.57 (m, 1H); 7.65 (m, 3H); 7.94 (d, J=8.1 Hz, 1H); 8.04 (dd, J=6.4, 2.7 Hz, 1H); 8.13 (s, 1H); 8.66 (s, 1H); 9.42 (s, 1H); MS (ESI(+)) m/e 444.1 (M+H)$^+$.

EXAMPLE 72

N-(5-methyl-3-pyridinyl)-N'-[4-(1-oxo-2,3-dihydro-1H-isoindol-4-yl)phenyl]urea hydrochloride A −5° C. solution of 5-methylnicotinohydrazide (353 mg, 2.33 mmol) in water (2.3 mL) and concentrated HCl (2.75 mL) was treated dropwise with a solution of NaNO$_2$ (161 mg, 2.3 mmol) in water (2.3 mL), stirred at −5° C. for 30 minutes, adjusted to pH>7 with 10% aqueous K$_2$CO$_3$, and filtered. The filter cake was dried under vacuum at room temperature to provide the acyl azide. A portion of this intermediate (63 mg) in toluene (6 mL) was heated to reflux for 1 hour, cooled, and treated with a suspension of Example 1D (75 mg, 0.33 mmol) in dichloromethane (4 mL). The reaction was stirred at room temperature overnight and filtered. The filter cake was purified by silica gel chromatography with 6% methanol/dichloromethane. The purified product was stirred with saturated NH$_4$Cl and filtered to give 53 mg of the desired product. $^1$H NMR (300 MHz, DMSO-d$_6$) δ 2.41 (s, 3H); 4.52 (s, 2H); 7.55–7.68 (m, 7H); 8.07 (s, 1H); 8.30 (s, 1H); 8.67 (s, 1H); 8.80 (s, 1H); 9.35 (s, 1H); 9.52 (s, 1H); MS (ESI(+)) m/e 359.1 (M+H)$^+$.

EXAMPLE 73

N-(3,4-dimethylphenyl)-N'-[3-methyl-4-(1-oxo-2,3-dihydro-1H-isoindol-4-yl)phenyl]urea

EXAMPLE 73A 4-(4-amino-2-methylphenyl)-1-isoindolinone

The desired product was prepared by substituting Example 54A and 3-methyl-4-bromoaniline for 4-(4,4,5,5-tetramethyl-1,3,2-dioxaborolan-2-yl)aniline and Example 1C, respectively, in Example 1D. MS (ESI(+) m/e 239 (M+H)$^+$.

EXAMPLE 73B

N-(3,4-dimethylphenyl)-N'-[3-methyl-4-(1-oxo-2,3-dihydro-1H-isoindol-4-yl)phenyl]urea The desired product was prepared by substituting Example 73A for Example 1D and 3,4-dimethylphenyl isocyanate for 3-methylphenyl isocyanate in Example 1E. $^1$H NMR (300 MHz, DMSO-d$_6$) δ 2.08 (s, 3H); 2.16 (s, 3H);

2.19 (s, 3H); 4.13 (s, 2H); 7.03 (d, J=8.1 Hz, 1H); 7.17 (d, J=8.1 Hz, 2H); 7.25 (d, J=2.0 Hz, 1H); 7.33 (dd, J=8.1, 2.4 Hz, 1H); 7.41–7.44 (m, 2H); 7.54 (t, J=7.5 Hz, 1H); 7.67 (dd, J=7.5, 1.0 Hz, 1H); 8.49 (s, 1H); 8.56 (s, 1H); 8.63 (s, 1H); MS (ESI(+)) m/e 386.1 (M+H)$^+$.

EXAMPLE 74

N-(3,5-dimethylphenyl)-N'-[3-methyl-4-(1-oxo-2,3-dihydro-1H-isoindol-4-yl)phenyl]urea The desired product was prepared by substituting Example 73A for Example 1D and 3,5-dimethylphenyl isocyanate for 3-methylphenyl isocyanate in Example 1E. $^1$H NMR (300 MHz, DMSO-d$_6$) δ 2.08 (s, 3H); 2.24 (s, 6H); 4.14 (s, 2H); 6.62 (s, 1H); 7.09 (s, 2H); 7.17 (d, J=8.1 Hz, 1H); 7.32 (dd, J=8.1, 2.0 Hz, 1H); 7.41–7.45 (m, 2H); 7.55 (t, J=7.5 Hz, 1H); 7.67 (dd, J=7.5, 1.0 Hz, 1H); 8.53 (s, 1H); 8.57 (s, 1H); 8.67 (s, 1H); MS (ESI(+)) m/e 386.1 (M+H)$^+$.

EXAMPLE 75

N-[3-methyl-4-(1-oxo-2,3-dihydro-1H-isoindol-4-yl)phenyl]-N'-(3-methylphenyl)urea The desired product was prepared by substituting Example 73A for Example 1D in Example 1E. $^1$H NMR (300 MHz, DMSO-d$_6$) δ 2.08 (s, 3H); 2.28 (s, 3H); 4.13 (s, 2H); 6.79 (d, J=7.1 Hz, 1H); 7.16 (t, J=8.5 Hz, 2H); 7.21–7.25 (m, 1H); 7.32–7.35 (m, 2H); 7.41–7.45 (m, 2H); 7.54 (t, J=7.5 Hz, 1H); 7.67 (dd, J=7.5, 1.0 Hz, 1H); 8.56 (s, 1H); 8.61 (s, 1H); 8.68 (s, 1H); MS (ESI(+)) m/e 372.1 (M+H)$^+$.

EXAMPLE 76

N-(3-chlorophenyl)-N'-[3-methyl-4-(1-oxo-2,3-dihydro-1H-isoindol-4-yl)phenyl]urea The desired product was prepared by substituting Example 73A for Example 1D and 3-chlorophenylisocyanate for 3-methylphenyl isocyanate in Example 1E. $^1$H NMR (300 MHz, DMSO-d$_6$) δ 2.09 (s, 3H); 4.13 (s, 2H); 7.02 (dt, J=6.9, 2.2 Hz, 1H); 7.19 (d, J=8.1 Hz, 1H); 7.26–7.36 (m, 3H); 7.41–7.45 (m, 2H); 7.55 (t, J=7.5 Hz, 1H); 7.67 (dd, J=7.5, 1.0 Hz, 1H); 7.73–7.74 (m, 1H); 8.56 (s, 1H); 8.84 (s, 1H); 8.97 (s, 1H); MS (ESI(+) m/e 392.1 (M+H)$^+$.

EXAMPLE 77

N-[3-methyl-4-(1-oxo-2,3-dihydro-1H-isoindol-4-yl)phenyl]-N'-[3-(trifluoromethyl)phenyl]urea The desired product was prepared by substituting Example 73A for Example 1D and 3-trifluoromethylphenyl isocyanate for 3-methylphenyl isocyanate in Example 1E. $^1$H NMR (300 MHz, DMSO-d$_6$) δ 2.09 (s, 3H); 4.14 (s, 2H); 7.20 (d, J=8.1 Hz, 1H); 7.30–7.37 (m, 2H); 7.43 (dd, J=7.5, 1.0 Hz, 1H); 7.47 (d, J=2.0 Hz, 1H); 7.49–7.60 (m, 3H); 7.67 (dd, J=7.5, 1.0 Hz, 1H); 8.04 (s, 1H); 8.56 (s, 1H); 8.83 (s, 1H); 9.08 (s, 1H); MS (ESI(+)) m/e 426.1 (M+H)$^+$.

EXAMPLE 78

N-[4-fluoro-3-(trifluoromethyl)phenyl]-N'-[3-methyl-4-(1-oxo-2,3-dihydro-1H-isoindol-4-yl)phenyl]urea The desired product was prepared by substituting Example 73A for Example 1D and 4-fluoro-3-trifluoromethylphenyl isocyanate for 3-methylphenyl isocyanate in Example 1E. $^1$H NMR (300 MHz, DMSO-d$_6$) δ 2.09 (s, 3H); 4.13 (s, 2H); 7.19 (d, J=8.1 Hz, 1H); 7.35 (dd, J=8.5, 2.0 Hz, 1H); 7.41–7.48 (m, 3H); 7.55 (t, J=7.5 Hz, 1H); 7.63–7.68 (m, 2H); 8.03 (dd, J=6.8, 2.7 Hz, 1H); 8.56 (s, 1H); 8.90 (s, 1H); 9.14 (s, 1H); MS (ESI(+)) m/e 444.1 (M+H)$^+$.

EXAMPLE 79

N-[2-chloro-4-(1-oxo-2,3-dihydro-1H-isoindol-4-yl)phenyl]-N'-(3-methylphenyl)urea

EXAMPLE 79A 4-(4-amino-3-chlorophenyl)-1-isoindolinone

The desired product was prepared by substituting Example 54A and 2-chloro-4-bromoaniline for 4-(4,4,5,5-tetramethyl-1,3,2-dioxaborolan-2-yl)aniline and Example 1C, respectively, in Example 1D. MS (ESI(+) m/e 259,261 (M+H)$^+$.

EXAMPLE 79B

N-[2-chloro-4-(1-oxo-2,3-dihydro-1H-isoindol-4-yl)phenyl]-N'-(3-methylphenyl)urea The desired product was prepared by substituting Example 79A for Example 1D in Example 1E. $^1$H NMR (300 MHz, DMSO-d$_6$) δ 2.30 (s, 3H); 4.54 (s, 2H); 6.83 (d, J=6.8 Hz, 1H); 7.19 (t, J=7.6 Hz, 1H); 7.25–7.27 (m, 1H); 7.33 (s, 1H); 7.56–7.61 (m, 2H); 7.67–7.70 (m, 2H); 7.73 (d, J=2.0 Hz, 1H); 8.31 (d, J=8.8 Hz, 1H); 8.42 (s, 1H); 8.68 (s, 1H); 9.41 (s, 1H); MS (ESI(+)) m/e 392.0 (M+H)$^+$.

EXAMPLE 80

N-[2-chloro-4-(1-oxo-2,3-dihydro-1H-isoindol-4-yl)phenyl]-N'-(3-chlorophenyl)urea The desired product was prepared by substituting Example 79A for Example 1D and 3-chlorophenyl isocyanate for 3-methylphenyl isocyanate in Example 1E. $^1$H NMR (300 MHz, DMSO-d$_6$) δ 4.54 (s, 2H); 7.06 (ddd, J=7.7, 2.1, 1.0 Hz, 1H); 7.26 (ddd, J=8.2, 2.0, 1.0 Hz, 1H); 7.34 (t, J=8.1 Hz, 1H); 7.57–7.61 (m, 2H); 7.67–7.70 (m, 2H); 7.74–7.77 (m, 2H); 8.28 (d, J=8.5 Hz, 1H); 8.49 (s, 1H); 8.68 (s, 1H); 9.67 (s, 1H); MS (ESI(+)) m/e 412.0 (M+H)$^+$.

EXAMPLE 81

N-[2-chloro-4-(1-oxo-2,3-dihydro-1H-isoindol-4-yl)phenyl]-N'-(3,5-dimethylphenyl)urea The desired product was prepared by substituting Example 79A for Example 1D and 3,5-dimethylphenyl isocyanate for 3-methylphenyl isocyanate in Example 1E. $^1$H NMR (300 MHz, DMSO-d$_6$) δ 2.25 (s, 6H); 4.54 (s, 2H); 6.66 (s, 1H); 7.10 (s, 2H); 7.56–7.61 (m, 2H); 7.67–7.70 (m, 2H); 7.73 (d, J=2.0 Hz, 1H); 8.31 (d, J=8.8 Hz, 1H); 8.40 (s, 1H); 8.68 (s, 1H); 9.34 (s, 1H); MS (ESI(+)) m/e 406.1 (M+H)+.

EXAMPLE 82

N-[2-chloro-4-(1-oxo-2,3-dihydro-1H-isoindol-4-yl)phenyl]-N'-phenylurea

The desired product was prepared by substituting Example 79A for Example 1D and phenyl isocyanate for 3-methylphenyl isocyanate in Example 1E. $^1$H NMR (300 MHz, DMSO-d$_6$) δ 4.54 (s, 2H); 7.01 (t, J=7.5 Hz, 1H); 7.32 (t, J=8.0 Hz, 2H); 7.49 (d, J=7.8 Hz, 2H); 7.57–7.62 (m, 2H); 7.68–7.74 (m, 3H); 8.31 (d, J=8.8 Hz, 1H); 8.45 (s, 1H); 8.70 (s, 1H); 9.49 (s, 1H); MS (ESI(+)) m/e 378.0 (M+H)+.

EXAMPLE 83

N-[3-chloro-4-(1-oxo-2,3-dihydro-1H-isoindol-4-yl)phenyl]-N'-(3-methylphenyl)urea

EXAMPLE 83A 4-(4-amino-2-chlorophenyl)-1-isoindolinone

The desired product was prepared by substituting Example 54A and 3-chloro-4-bromoaniline for 4-(4,4,5,5-tetramethyl-1,3,2-dioxaborolan-2-yl)aniline and Example 1C, respectively, in Example 1D. MS (ESI(+) m/e 259, 261 (M+H)+.

EXAMPLE 83B

N-[3-chloro-4-(1-oxo-2,3-dihydro-1H-isoindol-4-yl)phenyl]-N'-(3-methylphenyl)urea The desired product was prepared by substituting Example 83A for Example 1D in Example 1E. $^1$H NMR (300 MHz, DMSO-d$_6$) δ 2.29 (s, 3H); 4.21 (s, 2H); 6.82 (d, J=7.5 Hz, 1H); 7.17 (t, J=7.5 Hz, 1H); 7.24 (dt, J=9.0, 1.4 Hz, 1H); 7.32 (s, 1H); 7.38–7.39 (m, 2H); 7.50 (dd, J=7.5, 1.2 Hz, 1H); 7.58 (t, J=7.5 Hz, 1H); 7.71 (dd, J=7.5, 1.4 Hz, 1H); 7.87 (d, J=2.0 Hz, 1H); 8.60 (s, 1H); 8.73 (s, 1H); 8.98 (s, 1H); MS (ESI(+)) m/e 392.0 (M+H)+.

EXAMPLE 84

N-[3-chloro-4-(1-oxo-2,3-dihydro-1H-isoindol-4-yl)phenyl]-N'-(3-chlorophenyl)urea The desired product was prepared by substituting Example 83A for Example 1D and 3-chlorophenyl isocyanate for 3-methylphenyl isocyanate in Example 1E. $^1$H NMR (300 MHz, DMSO-d$_6$) δ 4.22 (s, 2H); 7.03–7.07 (m, 1H); 7.31–7.33 (m, 2H); 7.41 (s, 2H); 7.50 (dd, J=7.5, 1.4 Hz, 1H); 7.58 (t, J=7.5 Hz, 1H); 7.70–7.73 (m, 2H); 7.86 (s, 1H); 8.60 (s, 1H); 9.04 (s, 1H); 9.10 (s, 1H); MS (ESI(+)) m/e 411.9 (M+H)+.

EXAMPLE 85

N-[3-chloro-4-(1-oxo-2,3-dihydro-1H-isbindol-4-yl)phenyl]-N'-[3-(trifluoromethyl)phenyl]urea The desired product was prepared by substituting Example 83A for Example 1D and 3-trifluoromethylphenyl isocyanate for 3-methylphenyl isocyanate in Example 1E. $^1$H NMR (300 MHz, DMSO-d$_6$) δ 4.22 (s, 2H); 7.33 (d, J=7.5 Hz, 1H); 7.41 (d, J=8.1 Hz, 1H); 7.44 (dd, J=8.5, 1.7 Hz, 1H); 7.51 (dd, J=7.6, 1.4 Hz, 1H); 7.52 (d, J=8.1 Hz, 1H); 7.58 (t, J=7.5 Hz, 1H); 7.63 (d, J=9.1 Hz, 1H); 7.72 (dd, J=7.5, 1.0 Hz, 1H); 7.88 (d, J=1.4 Hz, 1H); 8.03 (s, 1H); 8.60 (s, 1H); 9.43 (s, 1H); 9.49 (s, 1H); MS (ESI(+)) m/e 446.0 (M+H)+.

EXAMPLE 86

N-[3-chloro-4-(1-oxo-2,3-dihydro-1H-isoindol-4-yl)phenyl]-N'-[4-fluoro-3-(trifluoromethyl)phenyl]urea The desired product was prepared by substituting Example 83A for Example 1D and 4-fluoro-3-trifluoromethylphenyl isocyanate for 3-methylphenyl isocyanate in Example 1E. $^1$H NMR (300 MHz, DMSO-d$_6$) δ 4.21 (s, 2H); 7.42–7.46 (m, 3H); 7.50 (dd, J=7.5, 1.0 Hz, 1H); 7.58 (t, J=7.5 Hz, 1H); 7.65–7.70 (m, 1H); 7.71 (dd, J=7.5, 1.4 Hz, 1H); 7.86 (t, J=1.4 Hz, 1H); 8.01 (dd, J=6.3, 2.6 Hz, 1H); 8.60 (s, 1H); 9.16 (s, 1H); 9.20 (s, 1H); MS (ESI(+)) m/e 464.0 (M+H)+.

EXAMPLE 87

N-[3-chloro-4-(1-oxo-2,3-dihydro-1H-isoindol-4-yl)phenyl]-N'-(3,5-dimethylphenyl)urea The desired product was prepared by substituting Example 83A for Example 1D and 3,5-dimethylphenyl isocyanate for 3-methylphenyl isocyanate in Example 1E. $^1$H NMR (300 MHz, DMSO-d$_6$) δ 2.24 (s, 6H); 4.21 (s, 2H); 6.64 (s, 1H); 7.09 (s, 2H); 7.35 (dd, J=8.5, 1.7 Hz, 1H); 7.40 (d, J=8.1 Hz, 1H); 7.50 (dd, J=7.6, 1.2 Hz, 1H); 7.58 (t, J=7.5 Hz, 1H); 7.71 (dd, J=7.5, 1.0 Hz, 1H); 7.88 (d, J=1.7 Hz, 1H); 8.60 (s, 1H); 8.64 (s, 1H); 8.95 (s, 1H); MS (ESI(+)) m/e 406.0 (M+H)+.

EXAMPLE 88

N-(3-chlorophenyl)-N'-[3-fluoro-4-(1-oxo-2,3-dihydro-1H-isoindol-4-yl)phenyl]urea

EXAMPLE 88A 4-(4-amino-2-fluorophenyl)-1-isoindolinone

The desired product was prepared by substituting Example 54A and 3-fluoro-4-bromoaniline for 4-(4,4,5,5-tetramethyl-1,3,2-dioxaborolan-2-yl)aniline and Example 1C, respectively, in Example 1D. MS (ESI(+) m/e 243 (M+H)+.

EXAMPLE 88

N-(3-chlorophenyl)-N'-[3-fluoro-4-(1-oxo-2,3-dihydro-1H-isoindol-4-yl)phenyl]urea The desired product was prepared by substituting Example 88A for Example 1D and 3-chlorophenyl isocyanate for 3-methylphenyl isocyanate in Example 1E. $^1$H NMR (300 MHz, DMSO-d$_6$) δ 4.55 (s, 2H); 7.06 (ddd, J=7.8, 2.0, 1.0 Hz, 1H); 7.26 (ddd, J=8.1, 2.0, 1.0 Hz, 1H); 7.33 (t, J=7.8 Hz, 1H); 7.43 (dd, J=8.7, 1.9 Hz, 1H); 7.58 (m, 2H); 7.68 (m, 2H); 7.75 (t, J=1.9 Hz, 1H); 8.25 (t, J=8.7 Hz, 1H); 8.69 (s, 1H); 8.75 (d, J=2.4 Hz, 1H); 9.31 (s, 1H); MS (ESI(−)) m/e 394.0 (M−H)−.

EXAMPLE 89

N-[3-fluoro-4-(1-oxo-2,3-dihydro-1H-isoindol-4-yl)phenyl]-N'-(3-methylphenyl)urea The desired product was prepared by substituting Example 88A for Example 1D in Example 1E. $^1$H NMR (300 MHz, DMSO-$d_6$) δ 2.29 (s, 3H); 4.55 (s, 2H); 6.82 (d, J=6.8 Hz, 1H); 7.18 (t, J=7.8 Hz, 1H); 7.25 (d, J=8.8 Hz, 1H); 7.31 (s, 1H); 7.42 (dd, J=8.7, 1.9 Hz, 1H); 7.54–7.61 (m, 2H); 7.67–7.70 (m, 2H); 8.29 (t, J=8.7 Hz, 1H); 8.67–8.69 (m, J=5.1 Hz, 2H); 9.04 (s, 1H); MS (ESI(+)) m/e 376.1 (M+H)$^+$.

EXAMPLE 90

N-(3,5-dimethylphenyl)-N'-[3-fluoro-4-(1-oxo-2,3-dihydro-1H-isoindol-4-yl)phenyl]urea The desired product was prepared by substituting Example 88A for Example 1D and 3,5-dimethylphenyl isocyanate for 3-methylphenyl isocyanate in Example 1E. $^1$H NMR (300 MHz, DMSO-$d_6$) δ 2.25 (s, 6H); 4.55 (s, 2H); 6.65 (s, 1H); 7.09 (s, 2H); 7.41 (dd, J=8.5, 1.7 Hz, 1H); 7.56 (dd, J=12.9, 1.7 Hz, 1H); 7.58 (d, J=15.0 Hz, 1H); 7.67–7.70 (m, 2H); 8.29 (t, J=8.7 Hz, 1H); 8.66 (d, J=2.7 Hz, 1H); 8.68 (s, 1H); 8.97 (s, 1H); MS (ESI(+)) m/e 390.1 (M+H)$^+$.

EXAMPLE 91

N-(3-methylphenyl)-N'-[4-(1-oxo-2,3-dihydro-1H-isoindol-4-yl)-2-(trifluoromethyl)phenyl]urea

EXAMPLE 91A

4-[4-amino-3-(trifluoromethyl)phenyl]-1-isoindolinone

The desired product was prepared by substituting Example 54A and 2-trifluoromethyl-4-bromoaniline for 4-(4,4,5,5-tetramethyl-1,3,2-dioxaborolan-2-yl)aniline and Example 1C, respectively, in Example 1D. MS (ESI(+) m/e 293 (M+H)$^+$.

EXAMPLE 91B

N-(3-methylphenyl)-N'-[4-(1-oxo-2,3-dihydro-1H-isoindol-4-yl)-2-(trifluoromethyl)phenyl]urea The desired product was prepared by substituting Example 91A for Example 1D in Example 1E. $^1$H NMR (300 MHz, DMSO-$d_6$) δ 2.29 (s, 3H); 4.54 (s, 2H); 6.83 (d, J=7.7 Hz, 1H); 7.19 (t, J=7.7 Hz, 1H); 7.24–7.27 (m, 1H); 7.32 (s, 1H); 7.62 (t, J=7.7 Hz, 1H); 7.71–7.75 (m, 2H); 7.85 (d, J=2.0 Hz, 1H); 7.92 (dd, J=8.3, 1.9 Hz, 1H); 8.12 (d, J=8.8 Hz, 1H); 8.17 (s, 1H); 8.69 (s, 1H); 9.39 (s, 1H); MS (ESI(+)) m/e 426.1 (M+H)$^+$.

EXAMPLE 92

N-(3-chlorophenyl)-N'-[4-(1-oxo-2,3-dihydro-1H-isoindol-4-yl)-2-(trifluoromethyl)phenyl]urea The desired product was prepared by substituting Example 91A for Example 1D and 3-chlorophenyl isocyanate for 3-methylphenyl isocyanate in Example 1E. $^1$H NMR (300 MHz, DMSO-$d_6$) δ 4.54 (s, 2H); 7.06 (ddd, J=7.7, 2.1, 1.4 Hz, 1H); 7.26 (ddd, J=8.1, 2.0, 1.4 Hz, 1H); 7.34 (t, J=8.1 Hz, 1H); 7.62 (t, J=7.5 Hz, 1H); 7.71–7.76 (m, 3H); 7.86 (d, J=2.0 Hz, 1H); 7.93 (dd, J=8.5, 2.0 Hz, 1H); 8.09 (d, J=8.5 Hz, 1H); 8.25 (s, 1H); 8.69 (s, 1H); 9.63 (s, 1H); MS (ESI(+)) m/e 446.0 (M+H)$^+$.

EXAMPLE 93

N-[4-fluoro-3-(trifluoromethyl)phenyl]-N'-[4-(1-oxo-2,3-dihydro-1H-isoindol-4-yl)-3-(trifluoromethyl)phenyl]urea

EXAMPLE 93A 4-(4-Amino-3-trifluoromethyl-phenyl-2,3-dihydro-isoindol-1-one

The desired product was prepared by substituting Example 54A and 3-trifluoromethyl-4-bromoaniline for 4-(4,4,5,5-tetramethyl-1,3,2-dioxaborolan-2-yl)aniline and Example 1C, respectively, in Example 1D. MS (ESI(+)) m/e 293 (M+H)$^+$.

EXAMPLE 93B

N-[4-fluoro-3-(trifluoromethyl)phenyl]-N'-[4-(1-oxo-2,3-dihydro-1H-isoindol-4-yl)-3-(trifluoromethyl)phenyl]urea The desired product was prepared by substituting Example 93A for Example 1D and 4-fluoro-3-trifluoromethylphenyl isocyanate for 3-methylphenyl isocyanate in Example 1E. $^1$H NMR (300 MHz, DMSO-$d_6$) δ 3.95 (br. s, 1H); 4.22 (br. s, 1H); 7.42–7.46 (m, 3H); 7.55 (t, J=7.5 Hz, 1H); 7.68–7.74 (m, 3H); 8.02 (dd, J=6.4, 2.7 Hz, 1H); 8.12 (d, J=2.0 Hz, 1H); 8.59 (s, 1H); 9.22 (s, 1H); 9.30 (s, 1H); MS (ESI(+)) m/e 498.0 (M+H)$^+$.

EXAMPLE 94

N-(3,5-dimethylphenyl)-N'-[4-(1-oxo-2,3-dihydro-1H-isoindol-4-yl)-2-(trifluoromethyl)phenyl]urea The desired product was prepared by substituting Example 91A for Example 1D and 3,5-dimethylphenyl isocyanate for 3-methylphenyl isocyanate in Example 1E. $^1$H NMR (300 MHz, DMSO-$d_6$) δ 2.25 (s, 6H); 4.54 (s, 2H); 6.66 (s, 1H); 7.10 (s, 2H); 7.62 (t, J=7.5 Hz, 1H); 7.72 (dd, J=4.4, 1.0 Hz, 1H); 7.74 (dd, J=4.0, 1.4 Hz, 1H); 7.85 (d, J=2.0 Hz, 1H); 7.91 (dd, J=8.5, 1.7 Hz, 1H); 8.12 (d, J=8.5 Hz, 1H); 8.16 (s, 1H); 8.71 (s, 1H); 9.33 (s, 1H); MS (ESI(+)) m/e 440.1 (M+H)$^+$.

EXAMPLE 95

N-(3-chlorophenyl)-N-[4-(1-oxo-2,3-dihydro-1H-isoindol-4-yl)-3-(trifluoromethyl)phenyl]urea The desired product was prepared by substituting Example 93A for Example 1D and 3-chlorophenyl isocyanate for 3-methylphenyl isocyanate in Example 1E. $^1$H NMR (300 MHz, DMSO-$d_6$) δ 3.95 (br. s, 1H); 4.22 (br. s, 1H); 7.02–7.09 (m, 1H); 7.29–7.35 (m, 2H); 7.42–7.45 (m, 2H); 7.55 (t, J=7.6 Hz, 1H); 7.68 (dd, J=8.1, 2.0 Hz, 1H); 7.71–7.74 (m, 2H); 8.13 (d, J=2.4 Hz, 1H); 8.59 (s, 1H); 9.13 (s, 1H); 9.31 (s, 1H); MS (ESI(+)) m/e 446.1 (M+H)$^+$.

EXAMPLE 96

N-(3-methylphenyl)-N'-[4-(1-oxo-2,3-dihydro-1H-isoindol-4-yl)-3-(trifluoromethyl)phenyl]urea The desired product was prepared by substituting Example 93A for Example 1D in Example 1E. $^1$H NMR (300 MHz, DMSO-$d_6$) δ 2.29 (s, 3H); 3.95 (br. s, 1H); 4.21 (br. s, 1H); 6.82 (d, J=7.1 Hz, 1H); 7.18 (t, J=7.5 Hz, 1H); 7.25 (d, J=8.5 Hz, 1H); 7.34 (s, 1H); 7.41–7.44 (m, 2H); 7.55 (t, J=7.5 Hz, 1H); 7.65 (dd, J=8.3, 1.9 Hz, 1H); 7.72 (dd, J=7.5, 1.0 Hz, 1H); 8.14 (d, J=2.4 Hz, 1H); 8.59 (s, 1H); 8.77 (s, 1H); 9.14 (s, 1H); MS (ESI(+)) m/e 426.1 (M+H)$^+$.

EXAMPLE 97

N-(3,4-dimethylphenyl)-N'-[4-(1-oxo-2,3-dihydro-1H-isoindol-4-yl)-3-(trifluoromethyl)phenyl]urea The desired product was prepared by substituting Example 93A for Example 1D and 3,4-dimethylphenyl isocyanate for 3-methylphenyl isocyanate in Example 1E. $^1$H NMR (300 MHz, DMSO-$d_6$) δ 2.17 (s, 3H); 2.20 (br. s, 3H); 3.94 (br. s, 1H); 4.21 (br. s, 1H); 7.05 (d, J=8.1 Hz, 1H); 7.19 (dd, J=8.1, 2.4 Hz, 1H); 7.27 (d, J=1.7 Hz, 1H); 7.40–7.44 (m, 2H); 7.55 (t, J=7.5 Hz, 1H); 7.64 (dd, J=8.3, 1.9 Hz, 1H); 7.72 (dd, J=7.5, 1.0 Hz, 1H); 8.13 (d, J=2.4 Hz, 1H); 8.59 (s, 1H); 8.66 (s, 1H); 9.10 (s, 1H); MS (ESI(+)) m/e 440.2 (M+H)$^+$.

EXAMPLE 98

N-(3,5-dimethylphenyl)-N'-[4-(1-oxo-2,3-dihydro-1H-isoindol-4-yl)-3-(trifluoromethyl)phenyl]urea The desired product was prepared by substituting Example 93A for Example 1D and 3,5-dimethylphenyl isocyanate for 3-methylphenyl isocyanate in Example 1E. $^1$H NMR (300 MHz, DMSO-$d_6$) δ 2.25 (s, 6H); 3.95 (br. s, 1H); 4.22 (br. s, 1H); 6.65 (s, 1H); 7.11 (s, 2H); 7.40–7.44 (m, 2H); 7.55 (t, J=7.5 Hz, 1H); 7.63 (dd, J=8.5, 2.0 Hz, 1H); 7.72 (dd, J=7.5, 1.0 Hz, 1H); 8.15 (d, J=2.4 Hz, 1H); 8.59 (s, 1H); 8.67 (s, 1H); 9.11 (s, 1H); MS (ESI(+)) m/e 440.1 (M+H)$^+$.

EXAMPLE 99

N-[2-ethyl-4-(1-oxo-2,3-dihydro-1H-isoindol-4-yl)phenyl]-N'-(3-methylphenyl)urea

EXAMPLE 99A 4-(4-amino-3-ethylphenyl)-1-isoindolinone

The desired product was prepared by substituting Example 54A and 2-ethyl-4-bromoaniline for 4-(4,4,5,5-tetramethyl-1,3,2-dioxaborolan-2-yl)aniline and Example 1C, respectively, in Example 1D. MS (ESI(+) m/e 253 (M+H)$^+$.

EXAMPLE 99B

N-[2-ethyl-4-(1-oxo-2,3-dihydro-1H-isoindol-4-yl)phenyl]-N'-(3-methylphenyl)urea The desired product was prepared by substituting Example 99A for Example 1D in Example 1E. $^1$H NMR (300 MHz, DMSO-$d_6$) δ 1.23 (t, J=7.5 Hz, 3H); 2.29 (s, 3H); 2.69 (q, J=7.5 Hz, 2H); 4.53 (s, 2H); 6.80 (d, J=7.1 Hz, 1H); 7.17 (t, J=7.8 Hz, 1H); 7.25 (d, J=8.1 Hz, 1H); 7.33 (s, 1H); 7.40–7.44 (m, 2H); 7.55–7.60 (m, 1H); 7.65–7.67 (m, 2H); 7.97–8.00 (m, 2H); 8.65 (s, 1H); 9.02 (s, 1H); MS (ESI(+)) m/e 386.1 (M+H)$^+$.

EXAMPLE 100

N-(3-chlorophenyl)-N'-[2-ethyl-4-(1-oxo-2,3-dihydro-1H-isoindol-4-yl)phenyl]urea The desired product was prepared by substituting Example 99A for Example 1D and 3-chlorophenyl isocyanate for 3-methylphenyl isocyanate in Example 1E. $^1$H NMR (300 MHz, DMSO-$d_6$) δ 1.23 (t, J=7.5 Hz, 3H); 2.69 (q, J=7.5 Hz, 2H); 4.53 (s, 2H); 7.03 (ddd, J=7.5, 2.1, 1.2 Hz, 1H); 7.25 (dt, J=8.5, 1.5 Hz, 1H); 7.32 (t, J=8.1 Hz, 1H); 7.42–7.45 (m, 2H); 7.58 (dd, J=8.3, 6.3 Hz, 1H); 7.65–7.68 (m, 2H); 7.77 (t, J=2.0 Hz, 1H); 7.94 (d, J=8.5 Hz, 1H); 8.09 (s, 1H); 8.65 (s, 1H); 9.28 (s, 1H); MS (ESI(−)) m/e 404.1 (M−H)$^-$.

EXAMPLE 101

N-[2-ethyl-4-(1-oxo-2,3-dihydro-1H-isoindol-4-yl)phenyl]-N'-[4-fluoro-3-(trifluoromethyl)phenyl]urea The desired product was prepared by substituting Example 99A for Example 1D and 4-fluoro-3-trifluoromethylphenyl isocyanate for 3-methylphenyl isocyanate in Example 1E. $^1$H NMR (300 MHz, DMSO-$d_6$) δ 1.23 (t, J=7.6 Hz, 3H); 2.69 (q, J=7.6 Hz, 2H); 4.53 (s, 2H); 7.42–7.48 (m, 3H); 7.56–7.68 (m, 4H); 7.91 (d, J=8.1 Hz, 1H); 8.03 (dd, J=6.6, 2.6 Hz, 1H); 8.12 (s, 1H); 8.66 (s, 1H); 9.41 (s, 1H); MS (ESI(+)) m/e 458.1 (M+H)$^+$.

EXAMPLE 102

N-(3,5-dimethylphenyl)-N'-[2-ethyl-4-(1-oxo-2,3-dihydro-1H-isoindol-4-yl)phenyl]urea The desired product was prepared by substituting Example 99A for Example 1D and 3,5-dimethylphenyl isocyanate for 3-methylphenyl isocyanate in Example 1E. $^1$H NMR (300 MHz, DMSO-$d_6$) δ 1.23 (t, J=7.5 Hz, 3H); 2.24 (s, 6H); 2.69 (q, J=7.5 Hz, 2H); 4.53 (s, 2H); 6.62 (s, 1H); 7.10 (s, 2H); 7.40–7.43 (m, 2H); 7.55–7.60 (m, 1H); 7.64–7.67 (m, 2H); 7.97–7.99 (m, 2H); 8.65 (s, 1H); 8.95 (s, 1H); MS (ESI(+)) m/e 400.1 (M+H)$^+$.

EXAMPLE 103

4-(2-anilino-1H-benzimidazol-5-yl)-1-isoindolinone

EXAMPLE 103A 5-bromo-N-phenyl-1H-benzimidazol-2-amine

Aniline (0.49 mL, 5.4 mmol) was added dropwise to a 0° C. solution of thiocarbonyldiimidazole(1.02 g, 5.7 mmol) in pyridine (20 mL). The resulting mixture was stirred at 0° C. for 1.5 hours, treated with 2-amino-4-bromoaniline (1 g, 5.3 mmol), stirred overnight at room temperature, then treated with EDCI (1.23 g, 6.4 mmol) and heated to 50° C. for 24 hours. The reaction was concentrated and the residue was purified by silica gel chromatography eluting with 20–75% ethyl acetate/hexanes to give 375 mg (25%) of the desired product. MS (ESI(+)) m/e 288 (M+H)$^+$.

EXAMPLE 103B 4-(2-anilino-1H-benzimidazol-5-yl)-1-isoindolinone

The desired product was prepared by substituting Example 54A and Example 103A for 4-(4,4,5,5-tetramethyl-1,3,2-dioxaborolan-2-yl)aniline and Example 1C, respectively, in Example 1D. $^1$H NMR (300 MHz, DMSO-$d_6$) δ 4.52 (d, J=3.4 Hz, 2H); 6.91–6.96 (m, 1H); 7.19–7.49 (m, 5H); 7.59 (dd, J=7.1, 2.4 Hz, 1H); 7.63–7.68 (m, 2H); 7.77 (d, J=8.5 Hz, 2H); 8.62 (d, J=6.4 Hz, 1H); 9.48 (d, J=2.4 Hz, 1H); 10.97 (app d, J=20.0 Hz, 1H); MS (ESI(−)) m/e 341.1 (M−H)$^−$.

EXAMPLE 104

N-{4-[6-(2-methoxyethoxy)-1-oxo-2,3-dihydro-1H-isoindol-4-yl]phenyl}-N'-(3-methylphenyl)urea

EXAMPLE 104A 4-bromo-6-methoxy-1-isoindolinone

The desired product was prepared by substituting methyl 3-bromo-5-methoxy-2-methylbenzoate (prepared according to the procedure described in *J. Am. Chem. Soc.* 1967, 1695–1704) for methyl 3-bromo-2-methylbenzoate in Examples 1B-C. MS (ESI(+)) m/e 242, 244 (M+H)$^+$.

EXAMPLE 104B 4-bromo-6-hydroxy-1-isoindolinone

A −78° C. suspension of Example 104A (100 mg, 0.41 mmol) in dichloromethane (13 mL) was treated dropwise with 1M BBr$_3$ in dichloromethane (1.2 mL, 1.2 mmol), stirred at −78° C. for 1 hour, and stirred at room temperature for 2 hours. The mixture was treated with additional 1M BBr$_3$ in dichloromethnae (0.8 mL), heated to reflux overnight, then cooled to room temperature, and partitioned between water and ethyl acetate. The organic phase was dried (Na$_2$SO$_4$), filtered, and concentrated to give 91 mg (97%) of the desired product. MS (ESI(−)) m/226, 228 (M−H)$^−$.

EXAMPLE 104C 4-bromo-6-(2-methoxyethoxy)-1-isoindolinone

A mixture of Example 104B (100 mg, 0.44 mmol), Cs$_2$CO$_3$ (163 mg, 0.5 mmol) and 2-bromoethyl methyl ether (0.045 mL, 0.46 mmol) in DMF (2.2 mL) was warmed to 60° C. for 4 hours, stirred at room temperature overnight, and partitioned between water and ethyl acetate. The organic phase was dried (Na$_2$SO$_4$), filtered, and concentrated to give 128 mg of the desired product. MS (ESI(+)) m/e 286,288 (M+H)$^+$.

EXAMPLE 104D

N-{4-[6-(2-methoxyethoxy)-1-oxo-2,3-dihydro-1H-isoindol-4-yl]phenyl}-N'-(3-methylphenyl)urea The desired product was prepared by substituting Example 104C for Example 1C and N-(3-methylphenyl)-N'-[4-(4,4,5,5-tetramethyl-1,3,2-dioxaborolan-2-yl)phenyl]urea for 4-(4,4,5,5-tetramethyl-1,3,2-dioxaborolan-2-yl)aniline in Example 1D. $^1$H NMR (300 MHz, DMSO-$d_6$) δ 2.29 (s, 3H); 3.33 (s, 3H); 3.68–3.71 (m, 2H); 4.21–4.24 (m, 2H); 4.44 (s, 2H); 6.80 (d, J=7.8 Hz, 1H); 7.14–7.16 (m, 2H); 7.19 (d, J=2.4 Hz, 1H); 7.25 (d, J=8.5 Hz, 1H); 7.31 (s, 1H); 7.56 (s, 4H); 8.65 (s, 2H); 8.82 (s, 1H); MS (ESI(+)) m/e 432.1 (M+H)$^+$.

EXAMPLE 105

({7-[4-({[(3-methylphenyl)amino]carbonyl}amino) phenyl]-3-oxo-2,3-dihydro-1H-isoindol-5-yl}oxy) acetic acid

EXAMPLE 105A

Tert-butyl [(7-bromo-3-oxo-2,3-dihydro-1H-isoindol-5-yl)oxy]acetate

A mixture of Example 104B (103 mg, 0.45 mmol), Cs$_2$CO$_3$ (164 mg, 0.5 mmol) and t-butyl bromoacetate (0.075 mL, 0.5 mmol) in DMF (2.2 mL) was stirred overnight at room temperature, diluted with water, and filtered. The filter cake was dried to give 154 mg (45%) of the desired product. MS (ESI(+)) m/e 342,344 (M+H)$^+$.

EXAMPLE 105B

Tert-butyl ({7-[4-({[(3-methylphenyl)amino] carbonyl}amino)phenyl]-3-oxo-2,3-dihydro-1H-isoindol-5-yl}oxy)acetate The desired product was prepared by substituting Example 105A for Example 1C and N-(3-methylphenyl)-N'-[4-(4,4,5,5-tetramethyl-1,3,2-dioxaborolan-2-yl)phenyl] urea for 4-(4,4,5,5-tetramethyl-1,3,2-dioxaborolan-2-yl) aniline in Example 1D. MS (ESI(+)) m/e 486 (M+H)$^+$.

EXAMPLE 105C ({7-[4-({[(3-methylphenyl)amino]carbonyl}amino) phenyl]-3-oxo-2,3-dihydro-1H-isoindol-5-yl}oxy) acetic acid A solution of Example 105B (70 mg, 0.14 mmol) in TFA (4 mL) was stirred at room temperature for 4 hours, then concentrated to give the desired product. $^1$H NMR (500 MHz, DMSO-$d_6$) δ 2.29 (s, 3H); 4.44 (s, 2H); 4.83 (s, 2H); 6.80 (d, J=7.7 Hz, 1H); 7.08 (d, J=2.4 Hz, 1H); 7.17 (t, J=7.7 Hz, 1H); 7.20 (d, J=2.4 Hz, 1H); 7.25 (d, J=8.7 Hz, 1H); 7.31 (s, 1H); 7.56 (m, 4H); 8.65 (s, 1H); 8.64 (s, 1H); 8.82 (s, 1H), 12.45–13.70 (br. s, 1H); MS (ESI(−)) m/e 430.1 (M−H)$^−$.

EXAMPLE 106

N-[4-(7-hydroxy-1-oxo-2,3-dihydro-1H-isoindol-4-yl)phenyl]-N'-(3-methylphenyl)urea

EXAMPLE 106A

Methyl 6-amino-3-bromo-2-methylbenzoate

A −20° C. solution of methyl 3-bromo-2-methylbenzoate (10 g, 43.7 mmol) in concentrated H$_2$SO$_4$ (100 mL) was treated dropwise with a solution of concentrated HNO$_3$ (2.75 μL) in concentrated H$_2$SO$_4$ (50 mL) at a rate that maintained the temperature below −15° C. The reaction was then stirred at 0° C. for 30 minutes, poured into ice, and extracted with diethyl ether. The extract was washed with aqueous NaHCO$_3$ and brine, dried (Na$_2$SO$_4$), filtered, and concentrated to give 9.32 g of the nitrated product. The crude product was added to a solution of SnCl$_2$ (32.2 g, 170 mmol) in concentrated HCl (34 mL) and methanol (52 mL) and the resulting suspension was stirred at room temperature for 4 hours. The resulting solution was concentrated, adjusted to pH 7 with aqueous NaOH, and filtered through diatomaceous earth (Celite®). The pad was washed with diethyl ether and dichloromethane and the combined filtrates were concentrated. The concentrate was purified by silica gel chromatography with 10–20% ethyl acetate/hexanes to give 3.59 g of the desired product. MS (ESI(−)) m/e 243 (M−H)$^-$.

EXAMPLE 106B

Methyl 3-bromo-6-hydroxy-2-methylbenzoate

A 0° C. suspension of Example 106A (1 g, 4.1 mmol) in water (6 mL) was treated dropwise with a solution of NaNO$_2$ (285 mg) in water (1.25 mL), stirred at 0° C. for 15 minutes, then added slowly to a 90° C. solution of concentrated H$_2$SO$_4$ (4 mL) in water (4 mL). The reaction was stirred at 90° C. for 45 minutes, cooled to room temperature, and extracted three times with diethyl ether. The combined extracts were washed with aqueous NaHCO$_3$ and brine, dried (MgSO$_4$), filtered, and concentrated to give 0.87 g of the desired product. MS (ESI(−)) m/e 226 (M−H)$^-$.

EXAMPLE 106C

Methyl 6-(acetyloxy)-3-bromo-2-methylbenzoate

A solution of Example 106B (1.05 g, 4.3 mmol) in pyridine (3 mL) was treated with acetic anhydride (0.82 mL, 8.6 mmol), stirred at room temperature for 2 hours, and partitioned between ethyl acetate and 2N HCl. The organic phase was washed sequentially with aqueous NaHCO$_3$, water, and brine, dried (MgSO$_4$), filtered, and concentrated to give 1.19 g (97% yield) of the desired product. MS (ESI(+)) m/e 304, 306 (M+H)$^+$.

EXAMPLE 106D 4-bromo-7-hydroxy-1-isoindolinone

The desired product was prepared by substituting Example 106C for Example 1A in Examples 1B and 1C. MS (ESI(+)) m/e 226,228 (M+H)$^+$.

EXAMPLE 106E

N-[4-(7-hydroxy-1-oxo-2,3-dihydro-1H-isoindol-4-yl)phenyl]-N'-(3-methylphenyl)urea The desired product was prepared by substituting Example 106D for Example 1C and N-(3-methylphenyl)-N'-[4-(4,4,5,5-tetramethyl-1,3,2-dioxaborolan-2-yl)phenyl] urea for 4-(4,4,5,5-tetramethyl-1,3,2-dioxaborolan-2-yl) aniline in Example 1D. $^1$H NMR (300 MHz, DMSO-d$_6$) δ 2.28 (s, 3H); 4.49 (s, 2H); 6.80 (d, J=7.7 Hz, 1H); 6.90 (d, J=8.5 Hz, 1H); 7.16 (t, J=7.7 Hz, 1H); 7.24 (d, J=8.8 Hz, 1H); 7.30 (s, 1H); 7.44–7.55 (m, 6H); 8.59 (d, J=7.1 Hz, 1H); 8.74 (s, 1H); 9.47 (s, 1H); MS (ESI(+)) m/e 374.1 (M+H)$^+$.

EXAMPLE 107

N-[4-(7-methoxy-1-oxo-2,3-dihydro-1H-isoindol-4-yl)phenyl]-N'-(3-methylphenyl)urea

EXAMPLE 107A 4-bromo-7-methoxy-1-isoindolinone

A solution of Example 106D (103 mg, 0.45 mmol) in DMF (4 mL) was treated with Cs$_2$CO$_3$ (162 mg, 0.5 mmol) and methyl iodide (0.03 mL, 0.48 mmol), stirred at room temperature for 3 hours, then poured into water. The resulting precipitate was filtered to give 76 mg (70%) of the desired product. MS (ESI(+)) m/e 242,244 (M+H)$^+$.

EXAMPLE 107B

N-[4-(7-methoxy-1-oxo-2,3-dihydro-1H-isoindol-4-yl)phenyl]-N'-(3-methylphenyl)urea The desired product was prepared by substituting Example 107A for Example 1C and N-(3-methylphenyl)-N'-[4-(4,4,5,5-tetramethyl-1,3,2-dioxaborolan-2-yl)phenyl] urea for 4-(4,4,5,5-tetramethyl-1,3,2-dioxaborolan-2-yl) aniline in Example 1D. $^1$H NMR (300 MHz, DMSO-d$_6$) δ 2.28 (s, 3H); 3.87 (s, 3H); 4.39 (s, 2H); 6.79 (d, J=7.5 Hz, 1H); 7.11 (d, J=8.5 Hz, 1H); 7.16 (t, J=7.8 Hz, 1H); 7.24 (d, J=8.5 Hz, 1H); 7.31 (s, 1H); 7.45 (d, J=8.8 Hz, 2H); 7.54 (app. dd, J=8.8, 2.4 Hz, 3H); 8.29 (s, 1H); 8.63 (s, 1H); 8.77 (s, 1H); MS (DCI) m/e 388.2 (M+H)$^+$.

EXAMPLE 108

Sodium ({7-[4-({[(3-methylphenyl)amino] carbonyl}amino)phenyl]-3-oxo-2,3-dihydro-1H-isoindol-4-yl}oxy)acetate

EXAMPLE 108A

Tert-butyl [(7-bromo-3-oxo-2,3-dihydro-1H-isoindol-4-yl)oxy]acetate

The desired product was prepared by substituting Example 106D for Example 104B in Example 105A. MS (DCI) m/e 342, 344 (M+H)$^+$.

EXAMPLE 108B

Sodium ({7-[4-({[(3-methylphenyl)amino] carbonyl}amino)phenyl]-3-oxo-2,3-dihydro-1H-isoindol-4-yl}oxy)acetate The desired product was prepared by substituting Example 108A for Example 1C and N-(3-methylphenyl)-N'-[4-(4,4,5,5-tetramethyl-1,3,2-dioxaborolan-2-yl)phenyl] urea for 4-(4,4,5,5-tetramethyl-1,3,2-dioxaborolan-2-yl) aniline and substituting toluene for methanol in Example 1D. $^1$H NMR (300 MHz, DMSO-d$_6$) δ 2.27 (s, 3H); 4.39 (s, 2H); 4.44 (s, 2H); 6.74 (d, J=7.7 Hz, 1H); 6.97 (d, J=8.8 Hz, 1H); 7.12 (t, J=7.7 Hz, 1H); 7.29 (d, J=8.8 Hz, 2H); 7.34 (d, J=9.2 Hz, 2H); 7.36 (d, J=8.5 Hz, 1H); 7.43 (d, J=8.8 Hz, 2H); 8.35 (s, 1H); 10.23 (s, 1H); 10.35 (s, 1H); MS (ESI(+)) m/e 432.1 (M+H)$^+$.

EXAMPLE 109

N-{4-[7-(2-methoxyethoxy)-1-oxo-2,3-dihydro-1H-isoindol-4-yl]phenyl}-N'-(3-methylphenyl)urea The desired product was prepared by substituting Example 106D for Example 104B in Examples 104C and 104D. $^1$H NMR (300 MHz, DMSO-d$_6$) δ 2.28 (s, 3H); 3.36 (s, 3H); 3.69–3.72 (m, 2H); 4.25 (dd, J=5.6, 3.9 Hz, 2H); 4.39 (s, 2H); 6.79 (d, J=7.1 Hz, 1H); 7.11 (d, J=8.5 Hz, 1H); 7.16 (t, J=7.8 Hz, 1H); 7.24 (d, J=8.5 Hz, 1H); 7.31 (s, 1H); 7.45 (d, J=8.8 Hz, 2H); 7.52 (d, J=8.5 Hz, 1H); 7.53 (d, J=8.8 Hz, 2H); 8.32 (s, 1H); 8.63 (s, 1H); 8.77 (s, 1H); MS (ESI(+)) m/e 432.1 (M+H)$^+$.

EXAMPLE 110

N-[4-(2-methyl-1-oxo-2,3-dihydro-1H-isoindol-4-yl)phenyl]-N'-(3-methylphenyl)urea

EXAMPLE 110A 4-bromo-2-methyl-1-isoindolinone

A solution of Example 1B (1 g, 3.25 mmol), methylamine hydrochloride (1.1 g, 16.2 mL) and triethylamine (2.2 mL, 16.2 mmol) in methanol (16 mL) was refluxed for 10 hours, cooled to room temperature, concentrated to ¼ volume, and partitioned between saturated NH$_4$Cl and ethyl acetate. The aqueous phase was extracted with ethyl acetate and the combined organic phases were washed with brine, dried (MgSO$_4$), filtered, and concentrated to give 707 mg of the desired product. MS (ESI(+)) m/e 226 (M+H)$^+$.

EXAMPLE 110B

N-[4-(2-methyl-1-oxo-2,3-dihydro-1H-isoindol-4-yl)phenyl]-N'-(3-methylphenyl)urea The desired product was prepared by substituting Example 110A for Example 1C and N-(3-methylphenyl)-N'-[4-(4,4,5,5-tetramethyl-1,3,2-dioxaborolan-2-yl)phenyl]urea for 4-(4,4,5,5-tetramethyl-1,3,2-dioxaborolan-2-yl)aniline and substituting toluene for methanol in Example 1D. $^1$H NMR (300 MHz, DMSO-d$_6$) δ 2.29 (s, 3H); 3.09 (s, 3H); 4.62 (s, 2H); 6.80 (d, J=7.5 Hz, 1H); 7.17 (t, J=7.5 Hz, 1H); 7.25 (d, J=8.5 Hz, 1H); 7.31 (s, 1H); 7.52–7.66 (m, 7H); 8.64 (s, 1H); 8.82 (s, 1H); MS (ESI(+)) m/e 358.1 (M+H)$^+$.

EXAMPLE 111

Benzyl 7-[4-({[(3-methylphenyl)amino]carbonyl}amino)phenyl]-3-oxo-2,3-dihydro-1H-isoindol-5-ylcarbamate

EXAMPLE 111A

Methyl 5-{[(benzyloxy)carbonyl]amino}-2-methyl-3-nitrobenzoate

A 0° C. solution of methyl 5-amino-2-methyl-3-nitrobenzoate (1 g, 4.76 mmol, prepared according to the procedure described in J.Med.Chem. 1984, 27, 386) and diisopropylethylamine (0.91 mL, 5.24 mmol) in THF (24 mL) was treated with benzyl chloroformate (0.65 mL, 5.34 mmol), stirred at 0° C. for 30 minutes, warmed to room temperature for 2 hours, poured into water, and extracted twice with ethyl acetate. The combined extracts were washed with brine, dried (MgSO$_4$), filtered, and concentrated to give 1.7 g of the desired product. MS (ESI(−)) m/e 343 (M−H)$^-$.

EXAMPLE 111B

Methyl 5-{[(benzyloxy)carbonyl]amino}-3-iodo-2-methylbenzoate

A suspension of iron powder (0.83 g, 14.8 mmol) and ammonium chloride (1.33 g, 24.7 mmol) in water was treated dropwise with a suspension of Example 111A (1.7 g, 4.94 mmol) in ethanol, stirred at 80° C. for 6 hours, cooled to room temperature, and filtered through diatomaceous earth (Celite®). The pad was washed with warm methanol and the filtrate was concentrated. The concentrate was partitioned between ethyl acetate and water. The extract was washed with brine, dried (MgSO$_4$), filtered, and concentrated to give 1.49 g of the intermediate amine. The crude product was dissolved in DMF (10 mL), cooled to 0° C., and treated dropwise with 6M HCl (2.4 mL) followed by a solution of NaNO$_2$ (0.327 g, 4.75 mmol) in water (5 mL). The solution was stirred at 0° C. for 30 minutes, treated portionwise with KI (788 mg, 4.75 mmol), diluted with DMF (10 µL), stirred at 0° C. for 2 hours, warmed to room temperature for 30 minutes, and extracted with diethyl ether. The extract was washed with aqueous 10% sodium thiosulfate, water, and brine, dried (MgSO$_4$), filtered, and concentrated. The residue was purified by silica gel chromatography with dichloromethane to give 0.86 g of the desired product. MS (ESI(+)) m/e 443 (M+NH$_4$)$^+$.

EXAMPLE 111C

Benzyl 7-iodo-3-oxo-2,3-dihydro-1H-isoindol-5-ylcarbamate

The desired product was prepared by substituting Example 111B for Example 1A in Examples 1B and 1C. MS (ESI(+)) m/e 426 (M+NH$_4$)$^+$.

EXAMPLE 111D

Benzyl 7-[4-({[(3-methylphenyl)amino]carbonyl}amino)phenyl]-3-oxo-2,3-dihydro-1H-isoindol-5-ylcarbamate The desired product was prepared by substituting Example 111C for Example 1C and N-(3-methylphenyl)-N'-[4-(4,4,5,5-tetramethyl-1,3,2-dioxaborolan-2-yl)phenyl]urea for 4-(4,4,5,5-tetramethyl-1,3,2-dioxaborolan-2-yl)aniline in Example 1D. $^1$H NMR (300 MHz, DMSO-d$_6$) d 2.28 (s, 3H); 4.44 (s, 2H); 5.19 (s, 2H); 6.80 (d, J=6.8 Hz, 1H); 7.16 (dd, J=8.1, 7.5 Hz, 1H); 7.23–7.26 (m, 1H); 7.31 (s, 1H); 7.35–7.50 (m, 7H); 7.57 (d, J=8.5 Hz, 2H); 7.72 (d, J=1.7 Hz, 1H); 7.81 (s, 1H); 8.64 (s, 2H); 8.81 (s, 1H); 10.05 (s, 1H); MS (ESI(−)) m/e 505.0 (M−H)$^-$.

EXAMPLE 112

N-(3-methylphenyl)-N'-[3-(1-oxo-2,3-dihydro-1H-isoindol-4-yl)phenyl]urea

The desired product was prepared by substituting 3-aminophenylboronic acid for 4-(4,4,5,5-tetramethyl-1,3,2-dioxa-borolan-2-yl)aniline in Examples ID and 1E. $^1$H NMR (300 MHz, DMSO-d$_6$) δ 2.28 (s, 3H); 4.51 (s, 2H); 6.79 (d, J=7.5 Hz, 1H); 7.16 (t, J=7.6 Hz, 1H); 7.21–7.26 (m, 2H); 7.31 (s, 1H); 7.40–7.42 (m, 2H); 7.61 (t, J=7.5 Hz, 1H); 7.67 (dd, J=7.5, 1.7 Hz, 1H); 7.70 (dd, J=7.1, 1.4 Hz, 1H); 7.78 (s, 1H); 8.67 (s, 1H); 8.70 (s, 1H); 8.80 (s, 1H); MS (ESI(+)) m/e 358.1 (M+H)$^+$.

EXAMPLE 113

N-[4-(6-methoxy-1-oxo-2,3-dihydro-1H-isoindol-4-yl)phenyl]-N'-(3-methylphenyl)urea The desired product was prepared by substituting Example 104A for Example 1C and N-(3-methylphenyl)-N'-[4-(4,4,5,5-tetramethyl-1,3,2-dioxaborolan-2-yl)phenyl]urea for 4-(4,4,5,5-tetramethyl-1,3,2-dioxaborolan-2-yl)aniline in Example 1D. $^1$H NMR (300 MHz, DMSO-d$_6$) δ 2.28 (s, 3H); 3.87 (s, 3H); 4.43 (s, 2H); 6.80 (d, J=7.5 Hz, 1H); 7.14–7.16 (m, 2H); 7.19 (d, J=2.4 Hz, 1H); 7.25 (d, J=9.2 Hz, 1H); 7.31 (s, 1H); 7.56 (app. s, 4H); 8.64 (app. s, 2H); 8.81 (s, 1H); MS (ESI(+)) m/e 388.1 (M+H)$^+$.

EXAMPLE 114

N-(3-methylphenyl)-N'-(4-{7-[3-(4-morpholinyl)propoxy]-1-oxo-2,3-dihydro-1H-isoindol-4-yl}phenyl)urea

EXAMPLE 114A 4-bromo-7-(3-chloropropoxy)-1-isoindolinone

A suspension of Example 106D (250 mg, 1.1 mmol), 3-chloropropanol (0.095 mL, 1.1 mmol), and triphenylphosphine (350 mg, 1.3 mmol) in dichloromethane (5 mL) at 0° C., was treated dropwise with DEAD (0.21 mL, 1.3 mmol) over 10 minutes. The resulting mixture was stirred at 0° C. for 1 hour, warmed to room temperature overnight, and concentrated. The residue was purified by silica gel chromatography with 50 to 60% ethyl acetate/hexanes to give 227 mg of the desired product which was contaminated with triphenylphosphine oxide. MS (ESI(+)) m/e 304,306 (M+H)$^+$.

EXAMPLE 114B 4-bromo-7-[3-(4-morpholinyl)propoxy]-1-isoindolinone

A solution of Example 114A (227 mg, 0.75 mmol), morpholine (0.33 mL, 3.8 mmol), and potassium iodide (70 mg, 0.42 mmol) in DMF (3 mL) was heated to 100° C. overnight in a sealed reaction vessel, poured into water, and filtered. The filtrate was extracted with ethyl acetate and the extract was washed with brine, dried (Na$_2$SO$_4$), filtered, and concentrated. The concentrate was purified by silica gel chromatography with 5 to 7% methanol/dichloromethane containing 1% triethylamine to give 130 mg of the desired product. MS (ESI(+)) m/e 355,357 (M+H)$^+$.

EXAMPLE 114C

N-(3-methylphenyl)-N'-(4-{7-[3-(4-morpholinyl)propoxy]-1-oxo-2,3-dihydro-1H-isoindol-4-yl}phenyl)urea The desired product was prepared by substituting Example 114B for Example 1C and N-(3-methylphenyl)-N'-[4-(4,4,5,5-tetramethyl-1,3,2-dioxaborolan-2-yl)phenyl]urea for 4-(4,4,5,5-tetramethyl-1,3,2-dioxaborolan-2-yl)aniline in Example 1D. $^1$H NMR (300 MHz, DMSO-d$_6$) δ 1.90 (m, 2H); 2.28 (s, 3H); 2.37 (m, 4H); 2.48 (t, J=7.5 Hz, 2H); 3.57 (m, 4H); 4.15 (t, J=6.1 Hz, 2H); 4.38 (s, 2H); 6.79 (d, J=7.5 Hz, 1H); 7.10 (d, J=8.8 Hz, 1H); 7.16 (t, J=7.5 Hz, 1H); 7.24 (d, J=8.1 Hz, 1H); 7.31 (s, 1H); 7.45 (d, J=8.8 Hz, 2H); 7.52 (m, 3H); 8.28 (s, 1H); 8.65 (s, 1H); 8.79 (s, 1H). MS (ESI(+)) m/e 501.2 (M+H)$^+$.

EXAMPLE 115

N-(3-methylphenyl)-2-[4-(1-oxo-2,3-dihydro-1H-isoindol-4-yl)phenyl]acetamide

EXAMPLE 115A 2-(4-bromophenyl)-N-(3-methylphenyl)acetamide

A solution of 4-bromophenylacetic acid (502 mg, 2.33 mmol), m-toluidine (0.25 mL, 2.33 mmol), HOBT (350 mg, 2.59 mmol), and N-methylmorpholine (0.51 mL, 4.64 mmol) in DMF (10 mL) was treated with EDCI (496 mg, 2.59 mmol), stirred overnight at room temperature, and poured into ice water. The resulting white precipitate was collected by filtration to give 672 mg of the desired product. MS (ESI(+)) m/e 304, 306 (M+H)$^+$.

EXAMPLE 115B

N-(3-methylphenyl)-2-[4-(1-oxo-2,3-dihydro-1H-isoindol-4-yl)phenyl]acetamide

The desired product was prepared by substituting Example 115A for N-(6-bromo-3-pyridinyl)-N-(3-methylphenyl)urea in Example 54B. $^1$H NMR (300 MHz, DMSO-d$_6$) δ 2.27 (s, 3H); 3.69 (s, 2H); 4.51 (s, 2H); 6.86 (d,J=7.6 Hz, 1H); 7.18 (t,J=7.6 Hz, 1H); 7.40 (d, J=8.5 Hz, 1H); 7.44–7.47 (m, 3H); 7.56–7.61 (m, 3H); 7.63–7.69 (m, 2H); 8.67 (s, 1H); 10.13 (s, 1H); MS (ESI(+)) m/e 357.1 (M+H)$^+$.

EXAMPLE 116

N-methyl-N-(3-methylphenyl)-N'-[4-(1-oxo-2,3-dihydro-1H-isoindol-4-yl)phenyl]urea A suspension of Example 1D (0.25 g, 1.1 mmol) in dioxane (3 mL) was sequentially treated with triethylamine (0.17 mL, 1.2 mmol) and triphosgene (0.11 g, 0.37 mmol), heated to 70° C. for 2 hours, and concentrated. The concentrate was resuspended in THF (3 mL), treated with N-methyltoluidine, stirred at room temperature for 18 hours, and partitioned between water and ethyl acetate. The aqueous phase was extracted with ethyl acetate and the combined extracts were washed with brine, dried (Na$_2$SO$_4$), filtered, and concentrated. The residue was purified by silica gel chromatography with 2% methanol/dichloromethane to give 76 mg (20% yield) of the desired product. $^1$H NMR (300 MHz, DMSO-d$_6$) δ 2.34 (s, 3H); 3.27 (s, 3H); 4.50 (s, 2H); 7.08 (d, J=7.46 Hz, 1H); 7.12 (d, J=8.48 Hz, 1H); 7.17 (s, 1H); 7.31 (t, J=7.80 Hz, 1H); 7.48 (d, J=8.82 Hz, 1H); 7.57 (d, J=8.82 Hz, 3H); 7.62 (d, J=3.39 Hz, 1H); 7.65 (d, J=5.76 Hz, 1H); 8.24 (s, 1H); 8.64 (s, 1H). MS (ESI(+)) m/e 372 (M+H)$^+$.

EXAMPLE 117

N-(3-chlorophenyl)-N-methyl-N'-[4-(1-oxo-2,3-dihydro-1H-isoindol-4-yl)phenyl]urea The desired product was prepared by substituting 3-chloro-N-methylaniline for N-methyltoluidine in Example 116. $^1$H NMR (300 MHz, DMSO-d$_6$) δ 3.34 (s, 3H); 4.51 (s, 2H); 7.28–7.30 (m, 1H); 7.31–7.33 (m, 1H); 7.41 (d, J=8.14 Hz, 1H); 7.46 (d, J=6.78 Hz, 1H); 7.51 (d, J=8.81 Hz, 2H); 7.57 (s, 1H); 7.59 (d, J=2.71 Hz, 2H); 7.63 (d, J=2.37 Hz, 1H); 7.65 (d, J=4.41 Hz, 1H); 8.60 (s, 1H); 8.67 (s, 1H). MS (ESI(–)) m/e 390 (M–H)$^-$.

EXAMPLE 118

N-{7-[4-({[(3-methylphenyl)amino]carbonyl}amino) phenyl]-3-oxo-2,3-dihydro-1H-isoindol-4-yl}benzamide The desired product was prepared by substituting benzoyl chloride for acetyl chloride in Example 4. $^1$H NMR (300 MHz, DMSO-d$_6$) δ 2.29 (s, 3H); 4.62 (s, 2H); 6.80 (d, J=7.12 Hz, 1H); 7.17 (t, J=7.63 Hz, 1H); 7.25 (d, J=8.48 Hz, 1H); 7.31 (s, 1H); 7.56 (s, 4H); 7.61 (d, J=8.81 Hz, 1H); 7.67 (d, J=9.49 Hz, 2H); 7.71 (d, J=8.48 Hz, 1H); 7.99 (dd, J=7.97, 1.53 Hz, 2H); 8.57 (d, J=8.48 Hz, 1H); 8.63 (s, 1H); 8.80 (s, 1H); 9.09 (s, 1H); 11.74 (s, 1H); MS (ESI(–)) m/e 475 (M–H)$^-$.

EXAMPLE 119

3-(dimethylamino)-N-{7-[4-({[(3-methylphenyl) amino]carbonyl}amino)phenyl]-3-oxo-2,3-dihydro-1H-isoindol-4-yl}benzamide The desired product was prepared by substituting 3-dimethylaminobenzoyl chloride for acetyl chloride in Example 4. $^1$H NMR (300 MHz, DMSO-d$_6$) δ 2.29 (s, 3H); 3.00 (s, 6H); 4.61 (s, 2H); 6.80 (d, J=7.12 Hz, 1H); 7.00 (dd, J=8.14, 2.37 Hz, 1H); 7.17 (t, J=7.63 Hz, 1H); 7.24 (d, J=6.78 Hz, 2H); 7.31 (s, 2H); 7.40 (t, J=7.97 Hz, 1H); 7.56 (s, 4H); 7.70 (d, J=8.48 Hz, 1H); 8.56 (d, J=8.14 Hz, 1H); 8.62 (s, 1H); 8.79 (s, 1H); 9.07 (s, 1H); 11.71 (s, 1H); MS (ESI(–)) m/e 518 (M–H)$^-$.

EXAMPLE 120

N-[4-(1-oxo-2,3-dihydro-1H-isoindol-4-yl)phenyl]-1,3-thiazole-2-carboxamide

The desired product was prepared by substituting 1,3-thiazole-2-carboxylic acid and Example 1D for 4-bromophenylacetic acid and m-toluidine respectively, in Example 115A. $^1$H NMR (500 MHz, DMSO-d$_6$) δ 4.52 (s, 2H); 7.58 (t, J=7.49 Hz, 1H); 7.62 (d, J=8.42 Hz, 2H); 7.67 (d, J=8.42 Hz, 2H); 7.99 (d, J=8.42 Hz, 2H); 8.12 (d, J=3.12 Hz, 1H); 8.14 (d, J=3.12 Hz, 1H); 8.64 (s, 1H); 10.90 (s, 1H); MS (ESI(–)) m/e 334 (M–H)$^-$.

EXAMPLE 121

N-(3-methylphenyl)-N'-[4-(1-oxo-2,3-dihydro-1H-isoindol-4-yl)phenyl]thiourea

A solution of Example 1D (0.1 g, 0.44 mmol) in DMF (3 mL) was treated with m-tolylisothiocyanate (0.06 mL, 0.45 mmol), stirred at room temperature overnight, then cooled to 0° C., treated with water, and extracted twice with ethyl acetate. The combined extracts were washed with brine, dried (Na$_2$SO$_4$), filtered, and concentrated. The residue was purified by silica gel chromatography eluting with 3% methanol/dichloromethane to give 72 mg of the desired product. $^1$H NMR (300 MHz, DMSO-d$_6$) δ 2.30 (s, 3H); 4.53 (s, 2H); 6.96 (d, J=7.12 Hz, 1H); 7.23 (t, J=7.80 Hz, 1H); 7.29 (d, J=7.80 Hz, 2H); 7.57–7.69 (m, 7H); 8.68 (s, 1H); 9.84 (s, 1H); 9.88 (s, 1H); MS (ESI(–)) m/e 372 (M–H)$^-$.

EXAMPLE 122

N-methyl-N'-(3-methylphenyl)-N-[4-(1-oxo-2,3-dihydro-1H-isoindol-4-yl)phenyl]urea

EXAMPLE 122A

4-[4-(methylamino)phenyl]-1-isoindolinone

The desired product was prepared by substituting 4-bromo-N-methylaniline (*Tetrahedron. Lett.* 1993, 34, 2115) for N-(6-bromo-3-pyridinyl)-N'-(3-methylphenyl) urea in Example 54B. MS (ESI(+)) m/e 239 (M+H)$^+$.

EXAMPLE 122B

N-methyl-N'-(3-methylphenyl)-N-[4-(1-oxo-2,3-dihydro-1H-isoindol-4-yl)phenyl]urea The desired product was prepared by substituting Example 122A for Example 1D in Example 1E. $^1$H NMR (300 MHz, DMSO-d$_6$) δ 2.25 (s, 3H); 3.33 (s, 3H); 4.55 (s, 2H); 6.78 (d, J=7.46 Hz, 1H); 7.12 (t, J=7.80 Hz, 1H); 7.27 (d, J=7.80 Hz, 2H); 7.43 (d, J=8.48 Hz, 2H); 7.58–7.70 (m, 5H); 8.26 (s, 1H); 8.68 (s, 1H); MS (ESI(+)) m/e 372 (M+H)$^+$.

EXAMPLE 123

4-(2,5-dimethoxyphenyl)-N-[4-(1-oxo-2,3-dihydro-1H-isoindol-4-yl)phenyl]-1,3-thiazole-2-carboxamide The desired product was prepared by substituting 4-(2,5-dimethoxyphenyl)-1,3-thiazole-2-carboxylic acid and Example 1D for 4-bromophenylacetic acid and m-toluidine, respectively, in Example 1115A. $^1$H NMR (300 MHz, DMSO-d$_6$) δ 3.83 (s, 3H); 3.91 (s, 3H); 4.56 (s, 2H); 7.00 (dd, J=8.99, 3.22 Hz, 1H); 7.13 (d, J=9.16 Hz, 1H); 7.62 (d, J=7.46 Hz, 1H); 7.65–7.73 (m, 4H); 8.02 (d, J=8.48 Hz, 2H); 8.09 (d, J=3.05 Hz, 1H); 8.47 (s, 1H); 8.68 (s, 1H); 10.78 (s, 1H); MS (ESI(–)) m/e 470 (M–H)$^-$.

EXAMPLE 124

4-(3-bromophenyl)-N-[4-(1-oxo-2,3-dihydro-1H-isoindol-4-yl)phenyl]-1,3-thiazole-2-carboxamide The desired product was prepared by substituting 4-(3-bromophenyl)-1,3-thiazole-2-carboxylic acid and Example 1D for 4-bromophenylacetic acid and m-toluidine, respectively, in Example 115A. $^1$H NMR (300 MHz, DMSO-d$_6$) δ 4.56 (s, 2H); 7.49 (t, J=7.80 Hz, 1H); 7.58–7.64 (m, 2H); 7.67–7.72 (m, 4H); 8.02 (d, J=8.82 Hz, 2H); 8.18 (d, J=7.80 Hz, 1H); 8.45 (s, 1H); 8.67 (d, J=7.46 Hz, 2H); 10.80 (s, 1H); MS (ESI(–)) m/e 488 (M–H)$^-$.

EXAMPLE 125

4-(4-{[4-(4-methoxyphenyl)-1,3-thiazol-2-yl]amino}phenyl)-1-isoindolinone

EXAMPLE 125A

[4-(1-oxo-2,3-dihydro-1H-isoindol-4-yl)-phenyl]-thiourea

A solution of ammonium thioisocyanate (78 mg, 1.07 mmol) in acetone (5 mL) was treated with benzoyl chloride (0.118 mL, 1.07 mmol), heated to reflux for 20 minutes, removed from heat, treated with Example 1D (200 mg, 0.89 mmol) and stirred at reflux for 1 hour. The resulting mixture was poured into ice water and the precipitate filtered, washed with water, and dried to give 295 mg of an off white solid which was added to 5% aqueous NaOH solution (5 mL). The suspension was heated to 80° C. for 30 minutes, cooled to room temperature, and poured onto cold 1N HCl. The pH of the solution was adjusted to pH 8 with saturated aqueous $Na_2CO_3$, and the turbid mixture was filtered. The filter cake was washed with water and dried to give 194 mg (77% yield) of the desired product. MS (ESI(−)) m/e 282 (M−H)⁻.

EXAMPLE 125B 4-(4-{[4-(4-methoxyphenyl)-1,3-thiazol-2-yl]amino}phenyl)-1-isoindolinone A suspension of Example 125A (90 mg, 0.32 mmol) and 2-bromo-1-(4-methoxy-phenyl)ethanone (73 mg, 0.32 mmol) in ethanol (3 mL) was stirred at reflux for 2 hours, cooled to room temperature, and filtered. The filter cake was washed with ethanol and dichloromethane and dried to give 118 mg (90% yield) of the desired product as the hydrobromide salt. $^1$H NMR (300 MHz, DMSO-$d_6$) δ 3.80 (s, 3H); 4.55 (s, 2H); 7.01 (d, J=8.81 Hz, 2H); 7.21 (s, 1H); 7.58–7.64 (m, 3H); 7.66–7.69 (m, 2H); 7.86 (dd, J=8.81, 7.12 Hz, 4H); 8.67 (s, 1H); 10.43 (s, 1H); MS (ESI(+)) m/e 414 (M+H)⁺.

EXAMPLE 126

4-[4-(1H-benzimidazol-2-ylamino)phenyl]-1-isoindolinone trifluoroacetate

A 0° C. solution of thiocarbonyldiimidazole (442 mg, 2.23 mmol) in pyridine (8 mL) was treated dropwise with a solution of Example 1D (500 mg, 2.23 mmol) in pyridine (8 nmL), stirred at 0° C. for 1.5 hours, warmed to room temperature, treated with 1,2-diaminobenzene (241 mg, 2.68 mmol), stirred at room temperature overnight, treated with EDCI (513 mg, 2.68 mmol), heated to 50° C. overnight, and concentrated. The residue was partitioned between ethyl acetate/THF and water. The organic extract was dried ($MgSO_4$), filtered, and concentrated. The concentrate was purified by silica gel chromatography with 5% methanol/dichloromethane, then further purified by preparative HPLC on a Waters Symmetry C8 column (25 mm×100 mm, 7 μm particle size) using a gradient of 10% to 100% acetonitrile: 0.1% aqueous TFA over 8 minutes (10 minute run time) at a flow rate of 40 mL/min to give to give 17 mg of the desired product. $^1$H NMR (300 MHz, DMSO-$d_6$) δ 4.56 (s, 2H); 7.25 (d, J=3.39 Hz, 1H); 7.27 (d, J=3.05 Hz, 1H); 7.43 (d, J=3.05 Hz, 1H); 7.45 (d, J=3.39 Hz, 1H); 7.62–7.26 (m, 7H); 8.71 (s, 1H); 10.95 (s, 1H); 12.94 (s, 1H); MS (ESI(−)) m/e 339 (M−H)⁻.

EXAMPLE 127

N-(3-methylphenyl)-N'-[5-(1-oxo-2,3-dihydro-1H-isoindol-4-yl)-2-thienyl]urea

EXAMPLE 127A

Methyl 5-(1-oxo-2,3-dihydro-1H-isoindol-4-yl)-2-thiophenecarboxylate

The desired product was prepared by substituting methyl 5-bromo-2-thiophenecarboxylate for N-(6-bromo-3-pyridinyl)-N'-(3-methylphenyl)urea in Example 54B. $R_f$=0.45 (10% $CH_3OH/CH_2Cl_2$).

EXAMPLE 127B 5-(1-oxo-2,3-dihydro-1H-isoindol-4-yl)-2-thiophenecarboxylic acid A suspension of Example 127A (0.34 g, 1.24 mmol) in THF (30 mL) and methanol (30 mL) was treated with 1N LiOH (10 mL), stirred at room temperature for 5 hours, then acidified with 1N HCl and diluted with diethyl ether. The resulting suspension was filtered and the filter cake was washed with water and dried to give 288 mg of the desired product. MS (ESI(−)) m/e 258 (M−H)⁻.

EXAMPLE 127C

N-(3-methylphenyl)-N'-[5-(1-oxo-2,3-dihydro-1H-isoindol-4-yl)-2-thienyl]urea

A solution of Example 127B (70 mg, 0.27 mmol) and triethylamine (0.046 mL, 0.32 mmol) in DMF (8 mL) was treated with diphenylphosphorylazide (0.072 mL, 0.32 mmol), heated to 80° C. for 2 hours, cooled to room temperature, and treated with 3-methylaniline (0.03 mL, 0.27 mL). The resulting mixture was heated to 80° C. for 2 hours, cooled to room temperature, diluted with water, and extracted with dichloromethane and ethyl acetate. The combined extracts were dried ($MgSO_4$), filtered, and concentrated. The concentrate was purified by silica gel chromatography, with 3% methanol/dichloromethane to give the desired product (13% yield). $^1$H NMR (300 MHz, DMSO-$d_6$) δ 2.29 (s, 3H), 4.58 (s, 2H), 6.63 (d, 1H, J =4.2 Hz), 6.82 (d, 1H, J=6.9 Hz), 7.14–7.27 (m, 3H), 7.34 (s, 1H), 7.48–7.58 (m, 2H), 7.75–7.79 (m, 1H), 8.73 (s, 1H), 8.77 (s, 1H), 9.86 (s, 1H); MS (ESI(+)) m/e 364.0 (M+H)⁺.

EXAMPLE 128

N-(3-methylphenyl)-N'-[4-(6-nitro-1-oxo-2,3-dihydro-1H-isoindol-4-yl)phenyl]urea

EXAMPLE 128A

Methyl 4'-amino-2-methyl-5-nitro-1,1'-biphenyl-3-carboxylate

Example 1A (20 g, 87.3 mmol) was cooled to −5° C. and treated dropwise with $H_2SO_4$ (100 mL) at such a rate as to maintain the internal temperature below 10° C. The reaction mixture was cooled to −30° C. and treated dropwise with nitric acid (5.7 mL, 91.7 mmol) at such a rate as to maintain the internal temperature below −12° C. After the addition was complete the reaction flask was placed in an ice bath for 30 minutes and poured onto crushed ice. The resulting suspension was extracted twice with diethyl ether and the combined extracts were washed with aqueous NaHCO$_3$ and brine, dried (MgSO$_4$), filtered, and concentrated to give 23 g of a mixture of methyl 3-bromo-2-methyl-5-nitrobenzoate and methyl 3-bromo-2-methyl-6-nitrobenzoate. Substitution of this mixture for Example 1C in Example 1D followed by purification by silica gel chromatography with 10 to 40% ethyl acetate/hexanes provided the desired product. $^1$H NMR (300 MHz, DMSO-d$_6$) δ 2.46 (s, 3H), 3.91 (s, 3H), 5.36 (s, 2H), 6.67 (d, J=8.5 Hz, 2H), 7.07 (d, J=8.1 Hz, 2H), 8.06 (d, J=2.7 Hz, 1H), 8.41 (d, J=2.7 Hz, 1H).

EXAMPLE 128B

Methyl 4'-[(tert-butoxycarbonyl)amino]-2-methyl-5-nitro-1,1'-biphenyl-3-carboxylate A suspension of Example 128A (1.606 g, 5.6 mmol) in THF (10 mL) was treated with triethylamine(0.78 mL, 5.6 mmol) and di-tert-butyldicarbonate (1.34 g, 6.17 mmol), and stirred at room temperature for 18 hours. The resulting precipitate was removed by filtration and the filtrate was concentrated. The concentrate was purified by silica gel chromatography with 20 to 30% ethyl acetate/hexanes to give 1.36 g of the desired product. m.p. 131–132° C.

EXAMPLE 128C 4-(4-aminophenyl)-6-nitro-1-isoindolinone

A solution of tert-butyl 4-(6-nitro-1-oxo-2,3-dihydro-1H-isoindol-4-yl)phenylcarbamate (0.276 g, prepared by substituting Example 128B for Example 1A in Examples 1B and 1C) in TFA (3 mL) and CH$_2$Cl$_2$ (3 mL) was stirred at room temperature for 1 hour, then concentrated to give 0.085 g of the desired product. $^1$H NMR (300 MHz, DMSO-d$_6$) δ 4.66 (s, 2H), 5.50 (s, 2H), 6.70 (d, J=8.5 Hz, 1H), 7.40 (d, J=8.8 Hz, 2H), 8.20 (d, J=2.0 Hz, 1H), 8.30 (d, J=2.0 Hz, 1H), 9.03 (s, 1H).

EXAMPLE 128D

N-(3-methylphenyl)-N'-[4-(6-nitro-1-oxo-2,3-dihydro-1H-isoindol-4-yl)phenyl]urea The desired product was prepared by substituting Example 128C for Example 1D in Example 1E. MS (ESI(−)) m/e 401 (M−H)$^-$; $^1$H NMR (300 MHz, DMSO-d$_6$) δ 2.29 (s, 3H), 4.70 (s, 2H), 6.81 (d, J=7.12 Hz, 1H), 7.17 (t, J=7.80 Hz, 1H), 7.25 (m, J=8.14 Hz, 1H), 7.32 (s, 1H), 7.65 (m, 4H), 8.30 (d, J=2.03 Hz, 1H), 8.40 (d, J=2.03 Hz, 1H), 8.66 (s, 1H), 8.89 (s, 1H), 9.09 (s, 1H).

EXAMPLE 129

N-[4-(6-amino-1-oxo-2,3-dihydro-1H-isoindol-4-yl)phenyl]-N'-(3-methylphenyl)urea The desired product was prepared by substituting Example 128D for Example 2 in Example 3. $^1$H NMR (500 MHz, DMSO-d$_6$) δ 2.28 (s, 3H), 4.31 (s, 2H), 5.36 (s, 2H), 6.80 (d, J=7.32 Hz, 1H), 6.82 (d, J=1.83 Hz, 1H), 6.86 (d, J=2.14 Hz, 1H), 7.16 (t, J=7.78 Hz, 1H), 7.25 (d, J=8.24 Hz, 1H), 7.31 (s, 1H), 7.45 (d, J=8.85 Hz, 2H), 7.54 (d, J=8.54 Hz, 2H), 8.40 (s, 1H), 8.69 (s, 1H), 8.84 (s, 1H); MS (ESI(+)) m/e 373 (M+H)$^+$.

EXAMPLE 130

N-{7-[4-({[(3-methylphenyl)amino]carbonyl}amino)phenyl]-3-oxo-2,3-dihydro-1H-isoindol-5-yl}acetamide The desired product was prepared by substituting Example 129 for Example 3 in Example 4. MS (ESI(−)) m/e 413 (M−H)$^-$; $^1$H NMR (300 MHz, DMSO-d$_6$) δ 2.09 (s, 3H), 2.29 (s, 3H), 4.45 (s, 2H), 6.80 (d, J=7.5 Hz, 1H), 7.16 (t, J=7.8 Hz, 1H), 7.25 (d, J=8.5 Hz, 1H), 7.32 (s, 1H), 7.50 (d, J=8.5 Hz, 1H), 7.58 (d, J=8.8 Hz, 1H), 7.77 (d, J=2.0 Hz, 1H), 7.98 (d, J=2.0 Hz, 1H), 8.65 (d, J=4.8 Hz, 2H), 8.84 (s, 1H), 10.19 (s, 1H).

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

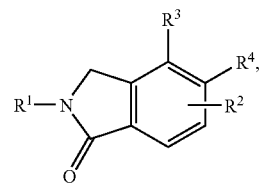

or a therapeutically acceptable salt thereof, wherein
$R^1$ is selected from the group consisting of hydrogen and alkyl;
$R^2$ is selected from the group consisting of hydrogen, alkoxy, alkoxyalkoxy, alkyl, carboxyalkoxy, carboxyalkyl, halo, haloalkyl, heterocyclylalkoxy, hydroxy, nitro, and —NR$^c$R$^d$; and
one of $R^3$ and $R^4$ A-X-R$^5$ and the other is hydrogen; wherein A-X-R$^5$ is drawn with its left end attached to the parent molecular moiety;
$R^5$ is phenyl;
A is phenyl which is optionally substituted with one or two substituents independently selected from the group consisting of alkyl, halo, haloalkoxy, and haloalkyl; and
X is (CH$_2$)$_m$N(R$^a$)C(O)N(R$^b$)(CH$_2$)$_n$, wherein R$^a$ and R$^b$ are hydrogen, m and n are and wherein each group is drawn with its left end attached to A and its right end attached to R$^5$.

2. The compound of claim 1 wherein R$^2$ is other than hydrogen.

3. The compound of claim 2 selected from the group consisting of
N-(3-methylphenyl)-N'-[4-(7-nitro-1-oxo-2,3-dihydro-1H-isoindol-4-yl)phenyl]urea;

N-[4-(7-amino-1-oxo-2,3-dihydro-1H-isoindol-4-yl)phenyl]-N'-(3-methylphenyl)urea;
N-{7-[4-({[(3-methylphenyl)amino]carbonyl}amino)phenyl]-3-oxo-2,3-dihydro-1H-isoindol-4-yl}acetamide;
$N^2,N^2$-dimethyl-$N^1$-{7-[4-({[(3-methylphenyl)amino]carbonyl}amino)phenyl]-3-oxo-2,3-dihydro-1H-isoindol-4-yl}glycinamide;
N-{7-[4-({[(3-methylphenyl)amino]carbonyl}amino)phenyl]-3-oxo-2,3-dihydro-1H-isoindol-4-yl}nicotinamide;
N-{7-[4-({[(3-methylphenyl)amino]carbonyl}amino)phenyl]-3-oxo-2,3-dihydro-1H-isoindol-4-yl}-2-phenylacetamide;
2-(2-methoxyethoxy)-N-{7-[4-({[(3-methylphenyl)amino]carbonyl}amino)phenyl]-3-oxo-2,3-dihydro-1H-isoindol-4-yl}acetamide;
N-{4-[6-(2-methoxyethoxy)-1-oxo-2,3-dihydro-1H-isoindol-4-yl]phenyl}-N'-(3-methylphenyl)urea;
({7-[4-({[(3-methylphenyl)amino]carbonyl}amino)phenyl]-3-oxo-2,3-dihydro-1H-isoindol-5-yl}oxy)acetic acid;
N-[4-(7-hydroxy-1-oxo-2,3-dihydro-1H-isoindol-4-yl)phenyl]-N'-(3-methylphenyl)urea;
N-[4-(7-methoxy-1-oxo-2,3-dihydro-1H-isoindol-4-yl)phenyl]-N'-(3-methylphenyl)urea;
({7-[4-({[(3-methylphenyl)amino]carbonyl}amino)phenyl]-3-oxo-2,3-dihydro-1H-isoindol-4-yl}oxy)acetic acid;
N-{4-[7-(2-methoxyethoxy)-1-oxo-2,3-dihydro-1H-isoindol-4-yl]phenyl}-N'-(3-methylphenyl)urea;
benzyl 7-[4-({[(3-methylphenyl)amino]carbonyl}amino)phenyl]-3-oxo-2,3-dihydro-1H-isoindol-5-ylcarbamate;
N-[4-(6-methoxy-1-oxo-2,3-dihydro-1H-isoindol-4-yl)phenyl]-N'-(3-methylphenyl)urea;
N-(3-methylphenyl)-N'-(4-{7-[3-(4-morpholinyl)propoxy]-1-oxo-2,3-dihydro-1H-isoindol-4-yl}phenyl)urea;
N-{7-[4-({[(3-methylphenyl)amino]carbonyl}amino)phenyl]-3-oxo-2,3-dihydro-1H-isoindol-4-yl}benzamide;
3-(dimethylamino)-N-{7-[4-({[(3-methylphenyl)amino]carbonyl}amino)phenyl]-3-oxo-2,3-dihydro-1H-isoindol-4-yl}benzamide;
N-(3-methylphenyl)-N'-[4-(6-nitro-1-oxo-2,3-dihydro-1H-isoindol-4-yl)phenyl]urea;
N-[4-(6-amino-1-oxo-2,3-dihydro-1H-isoindol-4-yl)phenyl]-N'-(3-methylphenyl)urea; and
N-{7-[4-({[(3-methylphenyl)amino]carbonyl}amino)phenyl]-3-oxo-2,3-dihydro-1H-isoindol-5-yl}acetamide.

4. The compound of claim 1 wherein $R^2$ is hydrogen.

5. The compound of claim 4 selected from the group consisting of
N-[4-(1-oxo-2,3-dihydro-1H-isoindol-4-yl)phenyl]-N'-phenylurea and
N-[2-chloro-4-(1-oxo-2,3-dihydro-1H-isoindol-4-yl)phenyl]-N'-phenylurea.

6. The compound of claim 4 wherein $R^5$ is monosubstituted.

7. The compound of claim 6 wherein A is unsubstituted.

8. The compound of claim 7 selected from the group consisting of
N-(3-methylphenyl)-N'-[4-(1-oxo-2,3-dihydro-1H-isoindol-4-yl)phenyl]urea;
N-(2-methylphenyl)-N'-[4-(1-oxo-2,3-dihydro-1H-isoindol-4-yl)phenyl]urea;
N-(4-methylphenyl)-N'-[4-(1-oxo-2,3-dihydro-1H-isoindol-4-yl)phenyl]urea;
N-(2-methoxyphenyl)-N'-[4-(1-oxo-2,3-dihydro-1H-isoindol-4-yl)phenyl]urea;
N-(3-methoxyphenyl)-N'-[4-(1-oxo-2,3-dihydro-1H-isoindol-4-yl)phenyl]urea;
N-(4-methoxyphenyl)-N'-[4-(1-oxo-2,3-dihydro-1H-isoindol-4-yl)phenyl]urea;
N-(2-fluorophenyl)-N'-[4-(1-oxo-2,3-dihydro-1H-isoindol-4-yl)phenyl]urea;
N-(3-fluorophenyl)-N'-[4-(1-oxo-2,3-dihydro-1H-isoindol-4-yl)phenyl]urea;
N-(4-fluorophenyl)-N'-[4-(1-oxo-2,3-dihydro-1H-isoindol-4-yl)phenyl]urea;
N-(2-chlorophenyl)-N'-[4-(1-oxo-2,3-dihydro-1H-isoindol-4-yl)phenyl]urea;
N-(3-chlorophenyl)-N'-[4-(1-oxo-2,3-dihydro-1H-isoindol-4-yl)phenyl]urea;
N-(4-chlorophenyl)-N'-[4-(1-oxo-2,3-dihydro-1H-isoindol-4-yl)phenyl]urea;
N-(2-bromophenyl)-N'-[4-(1-oxo-2,3-dihydro-1H-isoindol-4-yl)phenyl]urea;
N-(3-bromophenyl)-N'-[4-(1-oxo-2,3-dihydro-1H-isoindol-4-yl)phenyl]urea;
N-(4-bromophenyl)-N'-[4-(1-oxo-2,3-dihydro-1H-isoindol-4-yl)phenyl]urea;
N-[4-(1-oxo-2,3-dihydro-1H-isoindol-4-yl)phenyl]-N'-[4-(trifluoromethoxy)phenyl]urea;
N-[4-(1-oxo-2,3-dihydro-1H-isoindol-4-yl)phenyl]-N'-(3-phenoxyphenyl)urea;
N-[4-(1-oxo-2,3-dihydro-1H-isoindol-4-yl)phenyl]-N'-[4-(trifluoromethyl)phenyl]urea;
N-[4-(1-oxo-2,3-dihydro-1H-isoindol-4-yl)phenyl]-N'-(4-phenoxyphenyl)urea;
N-[3-(benzyloxy)phenyl]-N'-[4-(1-oxo-2,3-dihydro-1H-isoindol-4-yl)phenyl]urea;
N-[4-(1-oxo-2,3-dihydro-1H-isoindol-4-yl)phenyl]-N'-[3-(trifluoromethyl)phenyl]urea;
N-(3-ethylphenyl)-N'-[4-(1-oxo-2,3-dihydro-1H-isoindol-4-yl)phenyl]urea;
N-(3-cyanophenyl)-N'-[4-(1-oxo-2,3-dihydro-1H-isoindol-4-yl)phenyl]urea;
methyl 3-[({[4-(1-oxo-2,3-dihydro-1H-isoindol-4-yl)phenyl]amino}carbonyl)amino]benzoate;
N-(3-acetylphenyl)-N'-[4-(1-oxo-2,3-dihydro-1H-isoindol-4-yl)phenyl]urea;
N-(3-methylphenyl)-N'-[6-(1-oxo-2,3-dihydro-1H-isoindol-4-yl)-3-pyridinyl]urea;
N-[4-(2-methyl-1-oxo-2,3-dihydro-1H-isoindol-4-yl)phenyl]-N'-(3-methylphenyl)urea;
N-(3-methylphenyl)-N'-[3-(1-oxo-2,3-dihydro-1H-isoindol-4-yl)phenyl]urea;
N-methyl-N-(3-methylphenyl)-N'-[4-(1-oxo-2,3-dihydro-1H-isoindol-4-yl)phenyl]urea;
N-(3-chlorophenyl)-N-methyl-N'-[4-(1-oxo-2,3-dihydro-1H-isoindol-4-yl)phenyl]urea;
N-methyl-N'-(3-methylphenyl)-N-[4-(1-oxo-2,3-dihydro-1H-isoindol-4-yl)phenyl]urea; and
N-(3-methylphenyl)-N'-[5-(1-oxo-2,3-dihydro-1H-isoindol-4-yl)-2-thienyl]urea.

9. The compound of claim 6 wherein A is monosubstituted.

10. The compound of claim 9 selected from the group consisting of
N-[2-fluoro-4-(1-oxo-2,3-dihydro-1H-isoindol-4-yl)phenyl]-N'-(3-methylphenyl)urea;
N-(3-chlorophenyl)-N'-[2-fluoro-4-(1-oxo-2,3-dihydro-1H-isoindol-4-yl)phenyl]urea;
N-[2-fluoro-4-(1-oxo-2,3-dihydro-1H-isoindol-4-yl)phenyl]-N'-[4-fluoro-3-(trifluoromethyl)phenyl]urea;
N-(4-chlorophenyl)-N'-[2-fluoro-4-(1-oxo-2,3-dihydro-1H-isoindol-4-yl)phenyl]urea;

N-(3-bromophenyl)-N'-[2-fluoro-4-(1-oxo-2,3-dihydro-1H-isoindol-4-yl)phenyl]urea;
N-(3-methylphenyl)-N'-[4-(1-oxo-2,3-dihydro-1H-isoindol-4-yl)-2-(trifluoromethoxy)phenyl]urea;
N-(3-chlorophenyl)-N'-[4-(1-oxo-2,3-dihydro-1H-isoindol-4-yl)-2-(trifluoromethoxy)phenyl]urea;
N-[2-methyl-4-(1-oxo-2,3-dihydro-1H-isoindol-4-yl)phenyl]-N'-(3-methylphenyl)urea;
N-(3-chlorophenyl)-N'-[2-methyl-4-(1-oxo-2,3-dihydro-1H-isoindol-4-yl)phenyl]urea;
N-[3-methyl-4-(1-oxo-2,3-dihydro-1H-isoindol-4-yl)phenyl]-N'-(3-methylphenyl)urea;
N-(3-chlorophenyl)-N'-[3-methyl-4-(1-oxo-2,3-dihydro-1H-isoindol-4-yl)phenyl]urea;
N-[3-methyl-4-(1-oxo-2,3-dihydro-1H-isoindol-4-yl)phenyl]-N'-[3-(trifluoromethyl)phenyl]urea;
N-[2-chloro-4-(1-oxo-2,3-dihydro-1H-isoindol-4-yl)phenyl]-N'-(3-methylphenyl)urea;
N-[2-chloro-4-(1-oxo-2,3-dihydro-1H-isoindol-4-yl)phenyl]-N'-(3-chlorophenyl)urea;
N-[3-chloro-4-(1-oxo-2,3-dihydro-1H-isoindol-4-yl)phenyl]-N'-(3-methylphenyl)urea;
N-[3-chloro-4-(1-oxo-2,3-dihydro-1H-isoindol-4-yl)phenyl]-N'-(3-chlorophenyl)urea;
N-[3-chloro-4-(1-oxo-2,3-dihydro-1H-isoindol-4-yl)phenyl]-N'-[3-(trifluoromethyl)phenyl]urea;
N-(3-chlorophenyl)-N'-[3-fluoro-4-(1-oxo-2,3-dihydro-1H-isoindol-4-yl)phenyl]urea;
N-[3-fluoro-4-(1-oxo-2,3-dihydro-1H-isoindol-4-yl)phenyl]-N'-(3-methylphenyl)urea;
N-(3-methylphenyl)-N'-[4-(1-oxo-2,3-dihydro-1H-isoindol-4-yl)-2-(trifluoromethyl)phenyl]urea;
N-(3-chlorophenyl)-N'-[4-(1-oxo-2,3-dihydro-1H-isoindol-4-yl)-2-(trifluoromethyl)phenyl]urea;
N-(3-chlorophenyl)-N'-[4-(1-oxo-2,3-dihydro-1H-isoindol-4-yl)-3-(trifluoromethyl)phenyl]urea;
N-(3-methylphenyl)-N'-[4-(1-oxo-2,3-dihydro-1H-isoindol-4-yl)-3-(trifluoromethyl)phenyl]urea;
N-[2-ethyl-4-(1-oxo-2,3-dihydro-1H-isoindol-4-yl)phenyl]-N'-(3-methylphenyl)urea; and
N-(3-chlorophenyl)-N'-[2-ethyl-4-(1-oxo-2,3-dihydro-1H-isoindol-4-yl)phenyl]urea.

11. The compound of claim 1 wherein A is unsubstituted.

12. The compound of claim 11 selected from the group consisting of
N-(2,3-dimethylphenyl)-N'-[4-(1-oxo-2,3-dihydro-1H-isoindol-4-yl)phenyl]urea;
N-(2,4-dimethylphenyl)-N'-[4-(1-oxo-2,3-dihydro-1H-isoindol-4-yl)phenyl]urea;
N-(2,5-dimethylphenyl)-N'-[4-(1-oxo-2,3-dihydro-1H-isoindol-4-yl)phenyl]urea;
N-(3,4-dimethylphenyl)-N'-[4-(1-oxo-2,3-dihydro-1H-isoindol-4-yl)phenyl]urea;
N-(2,3-dimethoxyphenyl)-N'-[4-(1-oxo-2,3-dihydro-1H-isoindol-4-yl)phenyl]urea;
N-(2,4-dimethoxyphenyl)-N'-[4-(1-oxo-2,3-dihydro-1H-isoindol-4-yl)phenyl]urea;
N-(2,5-dimethoxyphenyl)-N'-[4-(1-oxo-2,3-dihydro-1H-isoindol-4-yl)phenyl]urea;
N-(3,4-dimethoxyphenyl)-N'-[4-(1-oxo-2,3-dihydro-1H-isoindol-4-yl)phenyl]urea;
N-(3,5-dimethoxyphenyl)-N'-[4-(1-oxo-2,3-dihydro-1H-isoindol-4-yl)phenyl]urea;
N-(2,3-dichlorophenyl)-N'-[4-(1-oxo-2,3-dihydro-1H-isoindol-4-yl)phenyl]urea;
N-(2,5-dichlorophenyl)-N'-[4-(1-oxo-2,3-dihydro-1H-isoindol-4-yl)phenyl]urea;
N-(3,4-dichlorophenyl)-N'-[4-(1-oxo-2,3-dihydro-1H-isoindol-4-yl)phenyl]urea;
N-(3,5-dichlorophenyl)-N'-[4-(1-oxo-2,3-dihydro-1H-isoindol-4-yl)phenyl]urea;
N-[4-chloro-3-(trifluoromethyl)phenyl]-N'-[4-(1-oxo-2,3-dihydro-1H-isoindol-4-yl)phenyl]urea;
N-(3-chloro-4-methoxyphenyl)-N'-[4-(1-oxo-2,3-dihydro-1H-isoindol-4-yl)phenyl]urea;
N-(4-bromo-3-methylphenyl)-N'-[4-(1-oxo-2,3-dihydro-1H-isoindol-4-yl)phenyl]urea;
N-(3-chloro-4-fluorophenyl)-N'-[4-(1-oxo-2,3-dihydro-1H-isoindol-4-yl)phenyl]urea;
N-(3-chloro-4-methylphenyl)-N'-[4-(1-oxo-2,3-dihydro-1H-isoindol-4-yl)phenyl]urea;
N-[2-fluoro-5-(trifluoromethyl)phenyl]-N'-[4-(1-oxo-2,3-dihydro-1H-isoindol-4-yl)phenyl]urea;
N-(3,5-dimethylphenyl)-N'-[4-(1-oxo-2,3-dihydro-1H-isoindol-4-yl)phenyl]urea; and
N-[4-fluoro-3-(trifluoromethyl)phenyl]-N'-[4-(1-oxo-2,3-dihydro-1H-isoindol-4-yl)phenyl]urea.

13. The compound of claim 1 wherein A is monosubstituted.

14. The compound of claim 13 selected from the group consisting of
N-(3,4-dimethylphenyl)-N'-[2-fluoro-4-(1-oxo-2,3-dihydro-1H-isoindol-4-yl)phenyl]urea;
N-(3,4-dimethylphenyl)-N'-[2-methyl-4-(1-oxo-2,3-dihydro-1H-isoindol-4-yl)phenyl]urea;
N-[4-fluoro-3-(trifluoromethyl)phenyl]-N'-[2-methyl-4-(1-oxo-2,3-dihydro-1H-isoindol-4-yl)phenyl]urea;
N-(3,4-dimethylphenyl)-N'-[3-methyl-4-(1-oxo-2,3-dihydro-1H-isoindol-4-yl)phenyl]urea;
N-(3,5-dimethylphenyl)-N'-[3-methyl-4-(1-oxo-2,3-dihydro-1H-isoindol-4-yl)phenyl]urea;
N-[4-fluoro-3-(trifluoromethyl)phenyl]-N'-[3-methyl-4-(1-oxo-2,3-dihydro-1H-isoindol-4-yl)phenyl]urea;
N-[2-chloro-4-(1-oxo-2,3-dihydro-1H-isoindol-4-yl)phenyl]-N'-(3,5-dimethylphenyl)urea;
N-[3-chloro-4-(1-oxo-2,3-dihydro-1H-isoindol-4-yl)phenyl]-N'-[4-fluoro-3-(trifluoromethyl)phenyl]urea;
N-[3-chloro-4-(1-oxo-2,3-dihydro-1H-isoindol-4-yl)phenyl]-N'-(3,5-dimethylphenyl)urea;
N-(3,5-dimethylphenyl)-N'-[3-fluoro-4-(1-oxo-2,3-dihydro-1H-isoindol-4-yl)phenyl]urea;
N-[4-fluoro-3-(trifluoromethyl)phenyl]-N'-[4-(1-oxo-2,3-dihydro-1H-isoindol-4-yl)-3-(trifluoromethyl)phenyl]urea;
N-(3,5-dimethylphenyl)-N'-[4-(1-oxo-2,3-dihydro-1H-isoindol-4-yl)-2-(trifluoromethyl)phenyl]urea;
N-(3,4-dimethylphenyl)-N'-[4-(1-oxo-2,3-dihydro-1H-isoindol-4-yl)-3-(trifluoromethyl)phenyl]urea;
N-(3,5-dimethylphenyl)-N'-[4-(1-oxo-2,3-dihydro-1H-isoindol-4-yl)-3-(trifluoromethyl)phenyl]urea;
N-[2-ethyl-4-(1-oxo-2,3-dihydro-1H-isoindol-4-yl)phenyl]-N'-[4-fluoro-3-(trifluoromethyl)phenyl]urea; and
N-(3,5-dimethylphenyl)-N'-[2-ethyl-4-(1-oxo-2,3-dihydro-1H-isoindol-4-yl)phenyl]urea.

15. A pharmaceutical composition comprising a compound of claim 1 or a therapeutically acceptable salt thereof, in combination with a therapeutically acceptable carrier.

* * * * *